United States Patent
Russell et al.

(10) Patent No.: US 12,077,525 B2
(45) Date of Patent: *Sep. 3, 2024

(54) HERBICIDAL COMPOUNDS

(71) Applicant: SYNGENTA CROP PROTECTION AG, Basel (CH)

(72) Inventors: Sally Elizabeth Russell, Bracknell (GB); Sean Ng, Bracknell (GB); James Alan Morris, Bracknell (GB)

(73) Assignee: SYNGENTA CROP PROTECTION AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/945,221

(22) Filed: Sep. 15, 2022

(65) Prior Publication Data

US 2023/0286952 A1  Sep. 14, 2023

Related U.S. Application Data

(63) Continuation of application No. 16/782,530, filed on Feb. 5, 2020, now Pat. No. 11,472,792.

(30) Foreign Application Priority Data

Feb. 5, 2019 (GB) .................................. 1901559

(51) Int. Cl.
| | | |
|---|---|---|
| C07D 403/04 | (2006.01) | |
| A01N 43/54 | (2006.01) | |
| A01N 43/56 | (2006.01) | |
| A01N 43/58 | (2006.01) | |
| A01N 43/80 | (2006.01) | |
| A01N 43/90 | (2006.01) | |
| C07D 207/325 | (2006.01) | |
| C07D 207/337 | (2006.01) | |
| C07D 207/34 | (2006.01) | |
| C07D 401/04 | (2006.01) | |
| C07D 401/14 | (2006.01) | |
| C07D 409/14 | (2006.01) | |
| C07D 413/04 | (2006.01) | |
| C07D 471/04 | (2006.01) | |
| C07D 487/04 | (2006.01) | |

(52) U.S. Cl.
CPC ........... *C07D 403/04* (2013.01); *A01N 43/54* (2013.01); *A01N 43/56* (2013.01); *A01N 43/58* (2013.01); *A01N 43/80* (2013.01); *A01N 43/90* (2013.01); *C07D 207/325* (2013.01); *C07D 207/337* (2013.01); *C07D 207/34* (2013.01); *C07D 401/04* (2013.01); *C07D 401/14* (2013.01); *C07D 409/14* (2013.01); *C07D 413/04* (2013.01); *C07D 471/04* (2013.01); *C07D 487/04* (2013.01)

(58) Field of Classification Search
CPC .............. C07D 403/04; C07D 207/325; C07D 207/337; C07D 207/34; C07D 401/04; C07D 401/14; C07D 409/14; C07D 413/04; C07D 471/04; C07D 487/04; A01N 43/54; A01N 43/56; A01N 43/58; A01N 43/80; A01N 43/90
See application file for complete search history.

(56) References Cited

U.S. PATENT DOCUMENTS

| | | |
|---|---|---|
| 5,763,470 A | 6/1998 | Tang et al. |
| 10,294,202 B2 | 5/2019 | Satterfield et al. |
| 10,851,085 B2 | 12/2020 | Morris et al. |
| 10,865,197 B2 | 12/2020 | Morris et al. |
| 10,882,846 B2 | 1/2021 | Morris et al. |
| 10,947,219 B2 | 3/2021 | Morris et al. |
| 11,059,806 B2 | 7/2021 | Morris et al. |
| 2006/0127396 A1 | 6/2006 | Ito et al. |
| 2007/0123508 A1 | 5/2007 | Olsson et al. |
| 2019/0169153 A1 | 6/2019 | Dugar et al. |

FOREIGN PATENT DOCUMENTS

| | | | |
|---|---|---|---|
| WO | 2015/052076 A1 | 4/2015 | |
| WO | 2015084796 A1 | 6/2015 | |
| WO | WO-2015084796 A1 * | 6/2015 | ............. A01N 43/08 |
| WO | 2018/065311 A1 | 4/2018 | |

OTHER PUBLICATIONS

PGR2020-00028 Judgment: Final Written Decision Determining Some Challenged Claims Unpatentable, Denying Petitioner's Motions to Exclude; *Syngenta Crop Protection AG v. FMC Corporation*, dated Aug. 31, 2021.

(Continued)

*Primary Examiner* — Jianfeng Song
(74) *Attorney, Agent, or Firm* — BakerHostetler; Toni-Junell Herbert

(57) ABSTRACT

The present disclosure provides compounds of formula (II)

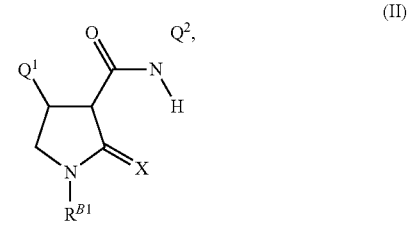

and compositions/methods of use thereof.

9 Claims, No Drawings

(56) References Cited

OTHER PUBLICATIONS

*Syngenta Crop Protection AG* v. *FMC Corporation*, Petition for Post-Grant Review, PGR2020-00028, U.S. Pat. No. 10,294,202, dated Feb. 21, 2020.
*Syngenta Crop Protection AG* v. *FMC Corporation*, Declaration of David Allen Hunt in Support of Syngenta Crop Protection AG's Petition for Post-Grant Review of U.S. Pat. No. 10,294,202, PGR2020-00028, dated Feb. 21, 2020.
*Syngenta Crop Protection AG* v. *FMC Corporation*, Patent Owner FMC's Preliminary Response, PGR2020-00028, U.S. Pat. No. 10,294,202, dated Jun. 18, 2020.
*Syngenta Crop Protection AG* v. *FMC Corporation*, Patent Owner FMC's Response, PGR2020-00028, U.S. Pat. No. 10,294,202, dated Dec. 9, 2020.
*Syngenta Crop Protection AG* v. *FMC Corporation*, Declaration of Franck E. Dayan, Ph.D., PGR2020-00028, U.S. Pat. No. 10,294,202, executed Dec. 8, 2020.
*Syngenta Crop Protection AG* v. *FMC Corporation*, Petitioner's Reply to Patent Owners Response, PGR2020-00028, U.S. Pat. No. 10,294,202, dated Mar. 10, 2021.
*Syngenta Crop Protection AG* v. *FMC Corporation*, Declaration of David Allen Hunt in Support of Petitioner's Reply to the Patent Owner's Response, PGR2020-00028, U.S. Pat. No. 10,294,202, dated Mar. 10, 2021.
PGR2020-00028 Decision Granting Institution of Post-Grant Review; *Syngenta Crop Protection AG* v. *FMC Corporation*, dated Sep. 15, 2020.
Barnes, David M et al., "Development of a Catalytic Enantioselective Conjugate Addition of 1,3-Dicarbonyl Compounds to Nitroalkenes for the Synthesis of Endothelin-A Antagonist ABT-546. Scope, Mechanism, and Further Application to the Synthesis of the Antidepressant Rolipram", J_ Am. Chem. Soc., Oct. 15, 2002, vol. 124, pp. 3097-13105.
Evans, David A. et al., "Ni(II)-Bis[{R,R)-N, N-dibenzylcyclohexane-1,2-diamine]Br2 Catalyzed Enantioselective Michael Additions of 1,3-Dicarbonyl Compounds to Conjugated Nitroalkenes", J_ Am. Chem. Soc., Jun. 23, 2005 (online), vol. 127, pp. 9958-9959.
International Search Report and Written Opinion for International Application No. PCT/EP2020/052780 mailed Mar. 30, 2020.

\* cited by examiner

HERBICIDAL COMPOUNDS

CROSS-REFERENCE TO RELATED APPLICATIONS

This application is a continuation of U.S. patent application Ser. No. 16/782,530 filed Feb. 5, 2020, which claims priority to Patent Application No. GB1901559.3 filed in the United Kingdom on Feb. 5, 2019, the entire contents of which are each incorporated by reference herein.

The present invention relates novel herbicidal compounds and their use in controlling plants or inhibiting plant growth.

Herbicidal dihydro-hydantoins of the formula

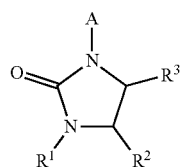

wherein A is a pyridine ring are taught in U.S. Pat. No. 4,600,430. Further hydantoins wherein A is an isoxazole ring are taught in e.g. U.S. Pat. No. 4,302,239 and Canadian Patent No. 1205077.

WO 2015/052076 discloses the compounds 1.1,

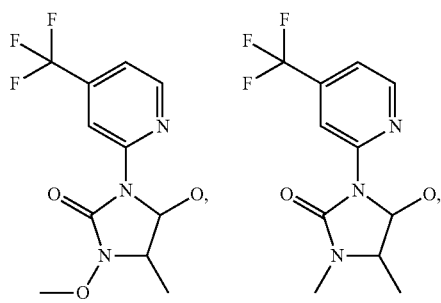

and 1.3

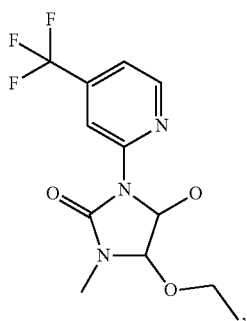

and their use as herbicides, whilst compound 1.4

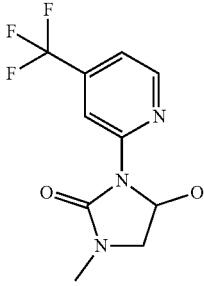 [SMILES: CN1CC(O)N(c2cc(C(F)(F)F)ccn2)C1=O]

is described in WO2015/059262, compound 1.5

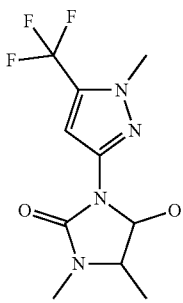 [SMILES: CC1C(O)N(c2cc(C(F)(F)F)n(C)n2)C(=O)N1C]

is described in WO 2015/097043 and compound 1.6

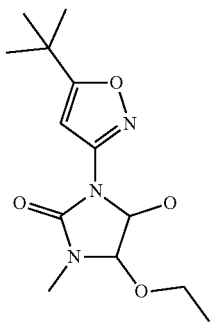 [SMILES: CCOC1C(O)N(c2cc(C(C)(C)C)on2)C(=O)N1C]

is described in WO 2015/193202. WO 2018/065311 describes mixtures of these compounds with certain herbicidal pyrrolidonone derivatives.

An object of the present invention is to provide herbicidal mixtures which are highly effective against various weed species at low dose and/or have increased crop tolerance.

The present invention is based on the finding that novel pyrazole-pyrrolidine carboxamides of formula (II) as defined herein are particularly efficacious as herbicides. They are thus particularly suitable as mixture partners for herbicidal dihydro-hydantoins. This in one aspect, the present invention provides a composition comprising (A) a compound of formula (I):

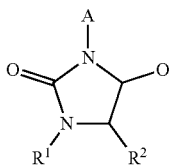
(I)

wherein R¹ is methyl or methoxy, R² is hydrogen, methyl or ethoxy and A is a substituted heteroaryl group and wherein said compound is selected from the group consisting of:

1.1
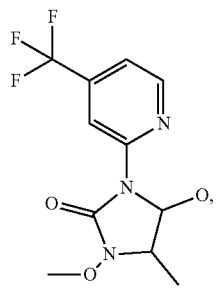

1.2
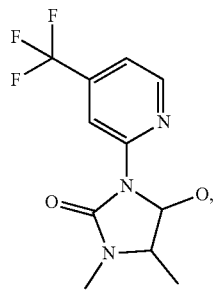

1.3
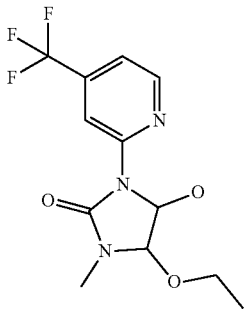

1.4
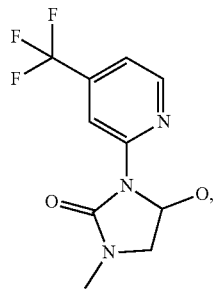

1.5
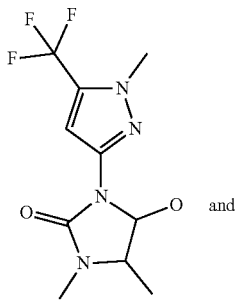
and 1.6
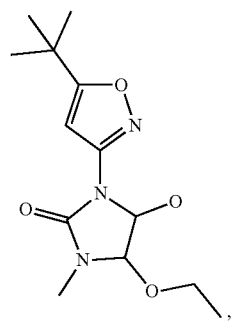, or an N-oxide or salt form thereof, and,
(B) one or more compounds of formula (II)

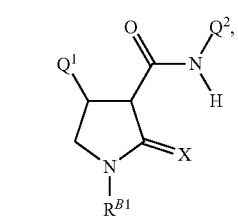
(II)

wherein; $R^{B1}$ is H, methyl, or methoxy; X is O or S; $Q^1$ is a di- or tri-substituted pyrazole, substituted on one ring nitrogen by $R^{B2}$ and substituted on at least one ring carbon by $R^{B3}$ wherein $R^{B2}$ is $C_1$-$C_3$ alkyl or $C_1$-$C_3$fluoroalkyl and each $R^{B3}$ is independently halogen, $C_1$-$C_3$fluoroalkyl, $C_1$-$C_3$haloalkoxy, $C_1$-$C_3$alkoxy, or $C_1$-$C_3$haloalkyl, $C_1$-$C_3$fluoroalkyl, $C_1$-$C_3$haloalkoxy, $C_1$-$C_3$alkoxy, or $C_1$-$C_3$alkyl; or $Q^1$ is a di-substituted pyrazole, substituted on one ring nitrogen by $R^{B2}$ and on an adjacent ring carbon by $R^{B3}$, wherein $R^{B2}$ is $C_1$-$C_3$ alkyl and $R^{B3}$ is $C_1$-$C_3$fluoroalkyl or $C_1$-$C_3$alkyl and $R^{B2}$ and $R^{B3}$ together with the atoms to which they are joined and $Q^1$ form an eight or nine-membered fused heterocyclic bicyclic ring system; $Q^2$ is a phenyl, pyridinyl, or thienyl ring system, optionally substituted by 1, 2, or 3 $R^{B5}$ substituents; and each $R^{B5}$ is independently halogen, $C_1$-$C_6$alkyl, $C_1$-$C_6$haloalkyl, $C_1$-$C_6$alkoxy, $C_1$-$C_6$haloalkoxy, cyano, nitro, $C_1$-$C_6$alkylthio, $C_1$-$C_6$alkylsulphinyl, or $C_1$-$C_6$alkylsulphonyl; or an N-oxide, or a salt form thereof.

In a second aspect, the invention provides the use of a composition of the invention as a herbicide.

In a third aspect, the invention provides a method of controlling plants, comprising applying to the plants or to the locus of the plants, a herbicidally effective amount of a composition of the invention.

In a fourth aspect, the invention provides a method of inhibiting plant growth, comprising applying to the plants or to the locus thereof, a herbicidally effective amount of a composition of the invention.

In a fifth aspect, the invention provides a method of controlling weeds in crops of useful plants, comprising applying to the weeds or to the locus of the weeds, or to the useful plants or to the locus of the useful plants, a herbicidally effective amount of a composition of the invention.

In a sixth aspect, the invention provides a method of selectively controlling grasses and/or weeds in crops of useful plants which comprises applying to the useful plants or locus thereof or to the area of cultivation a herbicidally effective amount of a composition of the invention.

When active ingredients are combined, the activity to be expected (E) for any given active ingredient combination obeys the so-called Colby Formula and can be calculated as follows (Colby, S. R., Calculating synergistic and antagonistic responses of herbicide combination, Weeds, Vol. 15, pages 20-22; 1967):

ppm=milligrams of active ingredient (a.i.) per liter
X=% action by first active ingredient using p ppm of the active ingredient
Y=% action by second active ingredient sing q ppm of the active ingredient.

According to Colby, the expected action of active ingredients A+B using p+q ppm of active ingredient is represented by the following formula:

$$E = X + Y - \frac{X \cdot Y}{100}$$

If the action actually observed (O) is greater than the expected action E then the action of the combination is super-additive, i.e. there is a synergistic effect. In mathematical terms, synergism corresponds to a positive value for the difference of (O-E). In the case of purely complementary addition of activities (expected activity), said difference (O-E) is zero. A negative value of said difference (O-E) signals a loss of activity compared to the expected activity.

Compounds of formula (I) and formula (II) are both effective herbicidal compounds, as shown in WO 2015/052076, WO2015/059262 WO 2015/097043 and WO 2015/193202 with respect to compounds of formula (I) and as shown herein with respect to compounds of formula (II). Accordingly, the combination of the present invention takes advantage of their additive activity, and certain embodiments may exhibit a synergistic effect. This occurs whenever the action of an active ingredient combination is greater than the sum of the actions of the individual components.

Furthermore, besides any actual synergistic action with respect to herbicidal activity, the composition according to the invention may also exhibit further surprising advantageous properties. Examples of such advantageous properties include improved characteristics of the useful plants including: emergence, crop yields, more developed root system, tillering increase, increase in plant height, bigger leaf blade, less dead basal leaves, stronger tillers, greener leaf colour, less fertilizers needed, less seeds needed, more productive tillers, earlier flowering, early grain maturity, less plant verse (lodging), increased shoot growth, improved plant vigor, and early germination.

In addition, it is also possible that the composition of the invention may show increased crop tolerance, when compared with the effect of the compound A (or B) alone. This occurs when the action of an active ingredient combination is less damaging to a useful crop than the action of one of the active ingredients alone.

As used herein, the term "halogen" or "halo" refers to fluorine (fluoro), chlorine (chloro), bromine (bromo) or iodine (iodo), preferably fluorine, chlorine or bromine.

As used herein, cyano means a —CN group.

As used herein, hydroxy means an —OH group.

As used herein, nitro means an —NO$_2$ group.

Each alkyl moiety either alone or as part of a larger group (such as alkoxy, alkylthio, haloalkyl, haloalkoxy et al.) may be straight-chained or branched, and as used herein the term specifically also includes cyclopropyl. Typically, the alkyl is, for example, methyl, ethyl, n-propyl, cylcopropyl, isopropyl, n-butyl, sec-butyl, isobutyl, tert-butyl, n-pentyl, neopentyl, or n-hexyl. The alkyl groups are generally $C_1$-$C_6$alkyl groups (except where already defined more narrowly), but are preferably $C_1$-$C_4$alkyl or $C_1$-$C_3$alkyl groups, and, more preferably, are $C_1$ or $C_2$alkyl groups (i.e. methyl or ethyl).

As used herein, the term "$C_1$-$C_3$alkoxy" refers to a radical of the formula —OR$_a$ where R$_a$ is a $C_1$-$C_3$alkyl radical as generally defined above. Examples of $C_1$-$C_3$alkoxy thus include methoxy, ethoxy, propoxy, and iso-propoxy.

As used herein, the term "$C_1$-$C_3$haloalkyl" refers to a $C_1$-$C_3$alkyl radical as generally defined above substituted by one or more of the same or different halogen atoms. Examples of $C_1$-$C_3$haloalkyl thus include, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl.

As used herein, the term "$C_1$-$C_3$haloalkoxy" refers to a $C_1$-$C_3$alkoxy group as defined above substituted by one or more of the same or different halogen atoms. Examples of $C_1$-$C_3$haloalkoxy thus include, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy.

The term "$C_1$-$C_6$alkylthio" refers to the group $C_1$-$C_6$alkyl-S—, and is, for example, methylthio, ethylthio, propylthio, isopropylthio, n-butylthio, isobutylthio, sec-butylthio or tert-butylthio, preferably methylthio or ethylthio.

The term "$C_1$-$C_6$alkylsulfinyl" refers to the group $C_1$-$C_6$alkyl-S(O)—, and is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

The term "$C_1$-$C_6$alkylsulfonyl" refers to the group $C_1$-$C_6$alkyl-S(O)$_2$—, and is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

The compounds of formula (I) may exist as different geometric isomers, or in different tautomeric forms. This invention covers the use of all such isomers and tautomers, and mixtures thereof in all proportions, as well as isotopic forms such as deuterated compounds. They may contain one or more asymmetric centers and may thus give rise to optical isomers and diastereomers. While shown for formula (I) without respect to stereochemistry, the present invention includes the use of all such optical isomers and diastereomers as well as the racemic and resolved, enantiomerically pure R and S stereoisomers and other mixtures of the R and S stereoisomers and agrochemically acceptable salts thereof.

It is recognized certain optical isomers or diastereomers may have favorable properties over the other. Thus when disclosing and claiming the invention, when a racemic mixture is disclosed, it is clearly contemplated that both optical isomers, including diastereomers, substantially free of the other, are disclosed and claimed as well.

In particular, the present invention covers the following forms of compounds 1.1 to 1.6:

1.1(a)
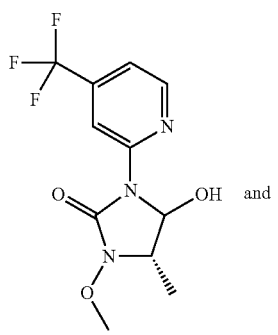
and 1.1(b)
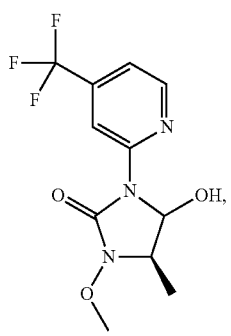

1.2(a)
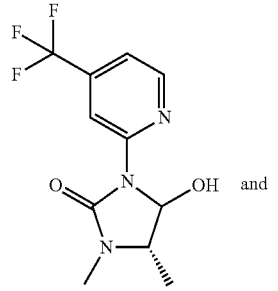
and 1.2(b)
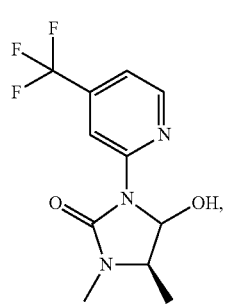

-continued 1.3(a)
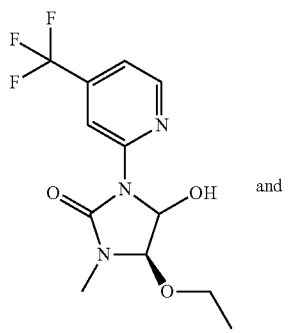
and 1.3(b)
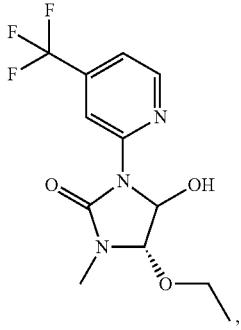
, 1.5(a)
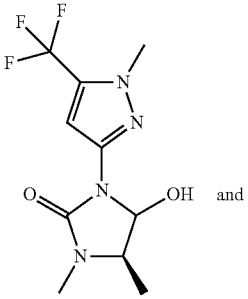
and 1.5(b)
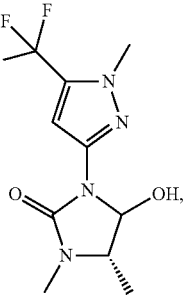
, 1.6(a)
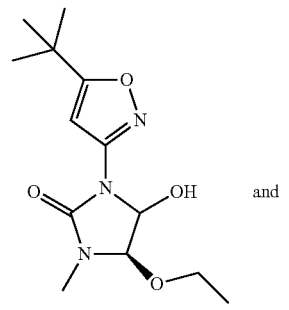
and

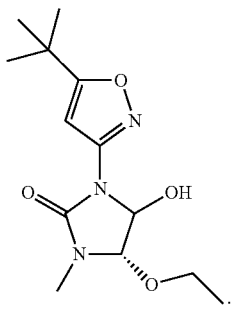

1.6(b)

Similarly, presence of one or more possible asymmetric carbon atoms in a compound of formula (II) means that the compounds may occur in chiral isomeric forms, i.e., enantiomeric or diastereomeric forms. Also atropisomers may occur as a result of restricted rotation about a single bond. Formula (II) is intended to include all those possible isomeric forms and mixtures thereof. The present invention includes the use of all those possible isomeric forms and mixtures thereof for a compound of formula (II). Likewise, formula (II) is intended to include all possible tautomers (including lactam-lactim tautomerism and keto-enol tautomerism) where present. The present invention thus includes the use of all possible tautomeric forms for a compound of formula (II).

Suitable salts include those derived from alkali or alkaline earth metals and those derived from ammonia and amines. Preferred cations include sodium, potassium, magnesium, and ammonium cations of the formula $N^+(R^{19}R^{20}R^{21}R^{22})$ wherein $R^{19}$, $R^{20}$, $R^{21}$ and $R^{22}$ are independently selected from hydrogen, $C_1$-$C_6$ alkyl and $C_1$-$C_6$ hydroxyalkyl. Salts of the compounds of formula (I) can be prepared by treatment of compounds of formula (I) with a metal hydroxide, such as sodium hydroxide, or an amine, such as ammonia, trimethylamine, diethanolamine, 2-methylthiopropylamine, bisallylamine, 2-butoxyethylamine, morpholine, cyclodecylamine, or benzylamine. Amine salts are often preferred forms of the compounds of formula (I) because they are water-soluble and lend themselves to the preparation of desirable aqueous based herbicidal compositions.

Acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic moiety.

Throughout this document the expression "composition" stands for the various mixtures or combinations of components (A) and (B), for example in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the components (A) and (B) is not essential for working the present invention.

The term "herbicide" as used herein means a compound that controls or modifies the growth of plants. The term "herbicidally effective amount" means the quantity of such a compound or combination of such compounds that is capable of producing a controlling or modifying effect on the growth of plants. Controlling or modifying effects include all deviation from natural development, for example killing, retardation, leaf burn, albinism, dwarfing and the like.

The term "locus" as used herein means fields in or on which plants are growing, or where seeds of cultivated plants are sown, or where seed will be placed into the soil. It includes soil, seeds, and seedlings, as well as established vegetation.

The term "plants" refers to all physical parts of a plant, including seeds, seedlings, saplings, roots, tubers, stems, stalks, foliage, and fruits.

The term "plant propagation material" denotes all generative parts of a plant, for example seeds or vegetative parts of plants such as cuttings and tubers. It includes seeds in the strict sense, as well as roots, fruits, tubers, bulbs, rhizomes, and parts of plants.

The term "safener" as used herein means a chemical that when used in combination with a herbicide reduces the undesirable effects of the herbicide on non-target organisms, for example, a safener protects crops from injury by herbicides but does not prevent the herbicide from killing the weeds.

Preferred embodiments of the invention are as set out below.

In one embodiment, (A) is compound 1.1.
In one embodiment (A) is compound 1.2.
In one embodiment (A) is compound 1.3.
In one embodiment (A) is compound 1.4.
In one embodiment (A) is compound 1.5.
In one embodiment (A) is compound 1.6.

Compounds of formula (I) as described herein may be prepared by techniques known to the person skilled in the art of organic chemistry. Methods for the production of compounds of formula (I) are described in WO2015/052076, WO2015/059262, WO2015/097043 and WO2015/193202.

With respect to compounds of formula (II), the preferred substituents are as follows, and the skilled man will appreciate that for any one of these substituents and/or integers, any of the definitions given below may be combined with that of any other substituent and/or integer given below or elsewhere in this document with respect to a compound of formula (II).

$R^{B1}$ is preferably hydrogen or methyl.

Where X is S, compounds of formula (II) may be procidal, although they may also retain a degree of intrinsic herbicidal activity and thus find utility in mixtures of the invention. However, it is particularly preferred that compounds of formula (II) will have oxygen as substituent X.

As stated above, $Q^2$ is a phenyl, pyridinyl, or thienyl ring system, optionally substituted by 1, 2, or 3 $R^{B5}$ substituents, and thus may be represented by the following generic structure

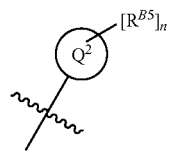

wherein ring $Q^2$ is a phenyl, pyridinyl, or thienyl ring, n is an integer or 0, 1, 2, or 3, and the jagged line represents the point of attachment of the ring to the rest of the molecule, in this case via the amide nitrogen. Preferably $Q^2$ is selected from the group consisting of Q²-1, Q²-2, Q²-3, Q²-4, Q²-5, and Q²-6 wherein $R^{B5}$, n and the jagged line are as described previously.

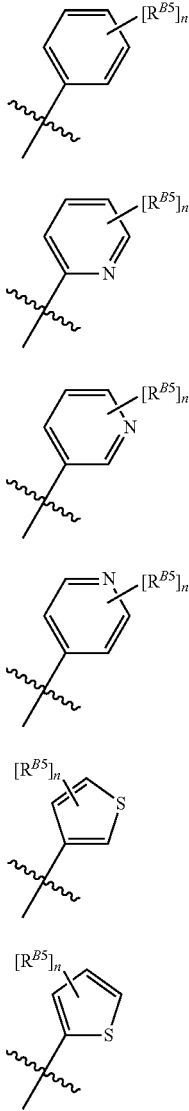

Also as defined herein, each $R^{B5}$ is independently halogen, $C_1$-$C_6$alkyl, $C_1$-$C_6$haloalkyl, $C_1$-$C_6$alkoxy, $C_1$-$C_6$haloalkoxy, cyano, nitro, $C_1$-$C_6$alkylthio, $C_1$-$C_6$alkylsulphinyl, or $C_1$-$C_6$alkylsulphonyl. Preferably n is 0, 1, or 2 and each $R^{B5}$ is borne by a ring carbon atom. More preferably each $R^{B5}$ is independently halogen, $C_1$-$C_4$ alkyl, $C_1$-$C_3$ haloalkyl, $C_1$-$C_3$alkoxy, or $C_1$-$C_3$haloalkoxy; more preferably chloro, fluoro, bromo, $C_1$-$C_2$haloalkyl, $C_1$-$C_2$haloalkoxy, or $C_1$-$C_2$alkoxy; more preferably still fluoro, ethyl, trifluoromethyl, difluoroethyl, methoxy, difluoromethoxy, or trifluoromethoxy. More preferably still, the value of n is 1, 2 or 3. Particularly preferred are compounds of formula (II) wherein n is 2 and at least one $R^{B5}$ is fluoro.

One of the key features of the compounds of formula (II) is that $Q^1$ is a pyrazole moiety carrying at least two substituents, wherein one of said substituents ($R^{B2}$) is borne by a ring nitrogen, and a second substituent ($R^{B3}$) is borne on a ring carbon atom. Clearly with such a configuration, $Q^1$ is carbon linked to the rest of the molecule.

When $Q^1$ is di-substituted and $R^{B3}$ is borne on the ring carbon atom adjacent the substituted ring nitrogen atom said $R^{B3}$ substitutent may be defined as $R^{B3SN}$. For the avoidance of doubt $R^{B3SN}$ is a sub-definition of $R^{B3}$ used purely to denote positional placement within the pyrazole moiety, and therefore $R^{B3SN}$ is also selected from the group consisting of halogen, $C_1$-$C_3$fluoroalkyl, $C_1$-$C_3$haloalkoxy, $C_1$-$C_3$alkoxy, and $C_1$-$C_3$alkyl. Thus when $Q^1$ is disubstituted, it may be represented by groups $Q^1$-2a, $Q^1$-2b, $Q^1$-2c, $Q^1$-2d, or Q1-e, as shown below, wherein $R^{B2}$, $R^{B3}$ and $R^{B3SN}$ are as defined above and the jagged line denotes the point of attachment to the rest of the molecule, in this case through the carbon atom at the 4-position of the pyrroldine ring,

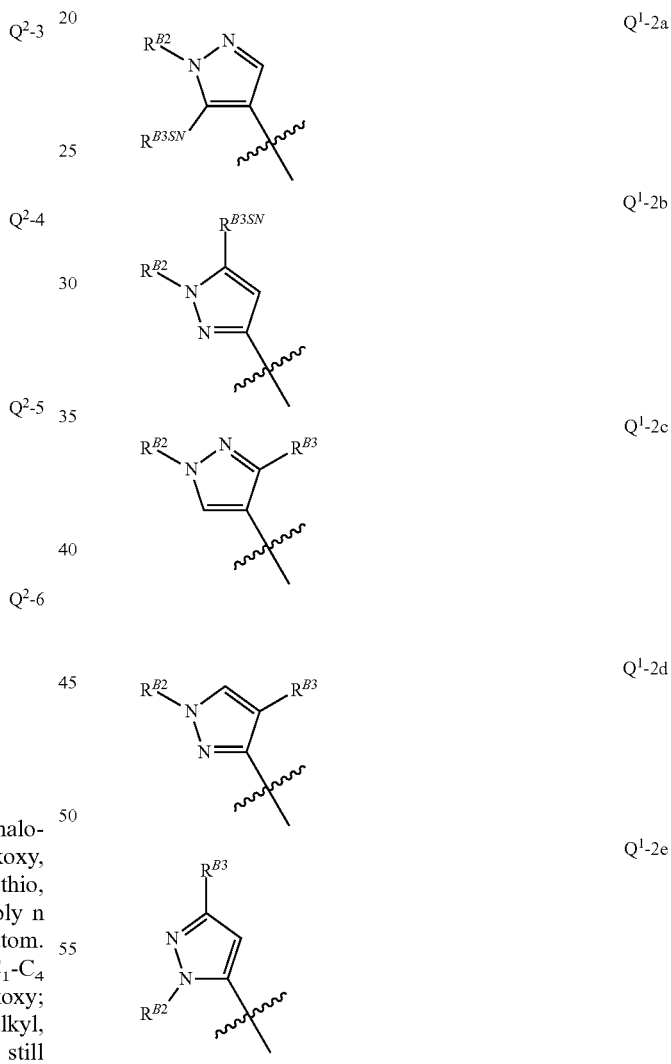

with groups $Q^1$-2a and $Q^1$-2b being particularly preferred, and $Q^1$-2b being the most preferred of the di-substituted pyrazoles.

Where $Q^1$ is tri-substituted it may be represented by groups $Q^1$-3a or $Q^1$-3b, wherein the third substituent ($R^{B3}$) is also borne on a ring carbon atom:

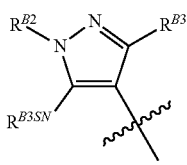

Q¹-3a

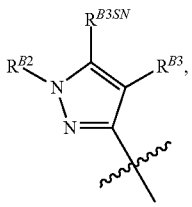

Q¹-3b, wherein $R^{B2}$, $R^{B3}$ and $R^{B3SN}$ and the jagged line are as defined above.

Preferably $R^{B2}$ is selected from the group consisting of methyl, ethyl, n-propyl, trifluoromethyl and difluoroethyl. More preferably $R^{B2}$ is selected from the group consisting of methyl, ethyl, and difluoroethyl.

Preferably $R^{B3}$ and/or $R^{B3SN}$ are each independently selected from chloro, fluoro, bromo, methyl, ethyl, diluoromethyl, trifluoromethyl $C_1$-$C_3$haloalkoxy, $C_1$-$C_3$alkoxy, or $C_1$-$C_3$alkyl. The skilled man will appreciate that where $Q^1$ is trisubstituted, $R^{B3}$ and $R^{B3SN}$ may be the same or different.

In a third set of embodiments $Q^1$ is a di-substituted pyrazole ring system, and $R^{B2}$ and $R^{B3}$ together with the atoms to which they are joined and $Q^1$ form an eight or nine-membered fused hetero-bicyclic ring system. In such embodiments $R^{B2}$ is $C_1$-$C_3$ alkyl and $R^{B3}$ is selected from $C_1$-$C_3$alkyl, $C_1$-$C_3$fluoroalkyl, and $C_1$-$C_3$haloalkoxy. Examples of such fused ring systems are shown below as groups $Q^1$-F1 to $Q^1$-F12 respectively:

Q¹-F1

Q¹-F2

Q¹-F3

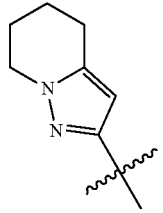

Q¹-F4

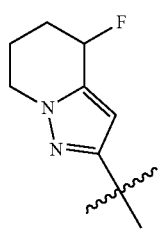

Q¹-F5

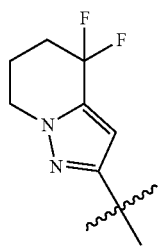

Q¹-F6

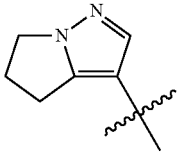

Q¹-F7

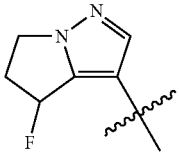

Q¹-F8

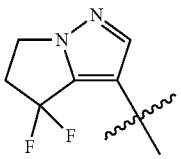

Q¹-F9

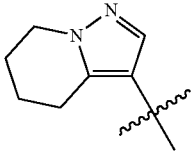

Q¹-F10

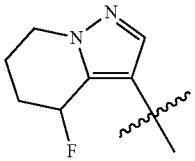

Q¹-F11

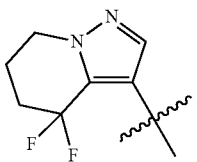

Q¹-F12

Particularly preferred compounds of formula (II) for use as component B in compositions of the invention are shown below in Table 1. The skilled man will appreciate that Table 1 specifies stereochemistry for compounds of formula (II). Whilst these are the most preferred stereoisomers for compounds of formula (II), racemic mixtures of stereoisomers are also herbicidal and as such may equally be employed as component B in mixtures of the invention.

TABLE 1

Compounds of formula (II) for use in compositions described herein.

| Compound No. | Name | Structure |
|---|---|---|
| 2.1 | (3S,4R)-N-(2,3-difluorophenyl)-1-methyl-4-[1-methyl-5-(trifluoromethyl)pyrazol-3-yl]-2-oxo-pyrrolidine-3-carboxamide | 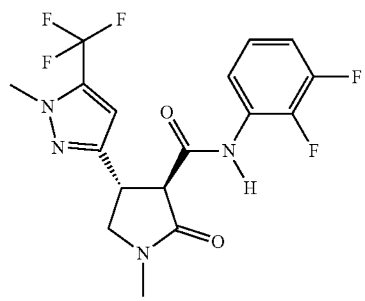 [SMILES: CN1C[C@H](c2cc(C(F)(F)F)n(C)n2)[C@@H](C(=O)Nc2cccc(F)c2F)C1=O] |
| 2.2 | (3S,4R)-N-(2-fluorophenyl)-1-methyl-4-[1-methyl-5-(trifluoromethyl)pyrazol-3-yl]-2-oxo-pyrrolidine-3-carboxamide | 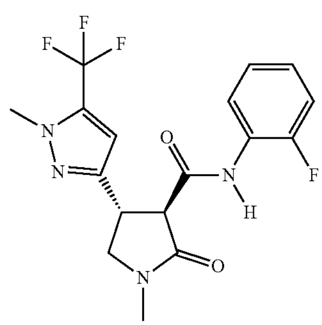 [SMILES: CN1C[C@H](c2cc(C(F)(F)F)n(C)n2)[C@@H](C(=O)Nc2ccccc2F)C1=O] |
| 2.3 | (3S,4R)-N-(2,4-difluorophenyl)-1-methyl-4-[1-methyl-5-(trifluoromethyl)pyrazol-3-yl]-2-oxo-pyrrolidine-3-carboxamide | 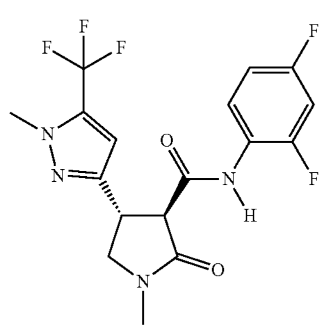 [SMILES: CN1C[C@H](c2cc(C(F)(F)F)n(C)n2)[C@@H](C(=O)Nc2ccc(F)cc2F)C1=O] |

TABLE 1-continued

Compounds of formula (II) for use in compositions described herein.

| Compound No. | Name | Structure |
|---|---|---|
| 2.4 | (3S,4R)-N-[3-fluoro-2-(trifluoromethoxy)phenyl]-1-methyl-4-[1-methyl-5-(trifluoromethyl)pyrazol-3-yl]-2-oxo-pyrrolidine-3-carboxamide | 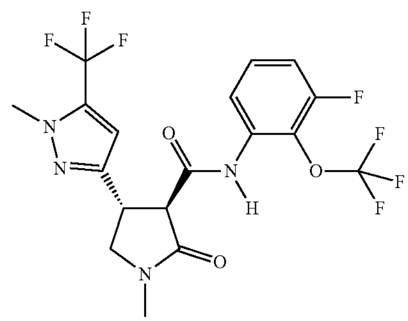 [SMILES: CN1C[C@H](c2cc(C(F)(F)F)n(C)n2)[C@@H](C(=O)Nc2cccc(F)c2OC(F)(F)F)C1=O] |
| 2.5 | (3S,4R)-N-[3-fluoro-2-(trifluoromethyl)phenyl]-1-methyl-4-[1-methyl-5-(trifluoromethyl)pyrazol-3-yl]-2-oxo-pyrrolidine-3-carboxamide | 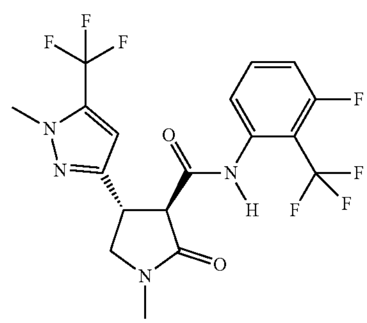 [SMILES: CN1C[C@H](c2cc(C(F)(F)F)n(C)n2)[C@@H](C(=O)Nc2cccc(F)c2C(F)(F)F)C1=O] |
| 2.6 | (3S,4R)-N-(3-fluoro-2-methoxy-phenyl)-1-methyl-4-[1-methyl-5-(trifluoromethyl)pyrazol-3-yl]-2-oxo-pyrrolidine-3-carboxamide | 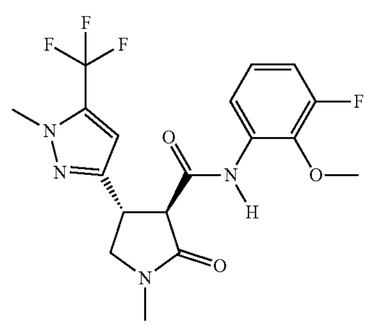 |
| 2.7 | (3S,4R)-1-methyl-4-[1-methyl-5-(trifluoromethyl)pyrazol-3-yl]-2-oxo-N-(2,3,4-trifluorophenyl)pyrrolidine-3-carboxamide | 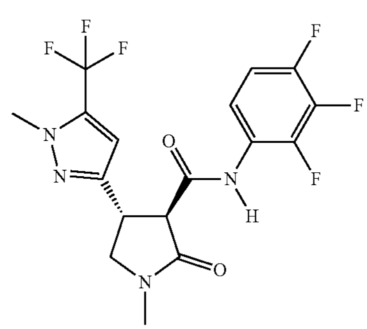 [SMILES: CN1C[C@H](c2cc(C(F)(F)F)n(C)n2)[C@@H](C(=O)Nc2ccc(F)c(F)c2F)C1=O] |

TABLE 1-continued

Compounds of formula (II) for use in compositions described herein.

| Compound No. | Name | Structure |
|---|---|---|
| 2.8 | (3S,4R)-N-(2,6-difluoro-3-pyridyl)-1-methyl-4-[1-methyl-5-(trifluoromethyl)pyrazol-3-yl]-2-oxo-pyrrolidine-3-carboxamide | 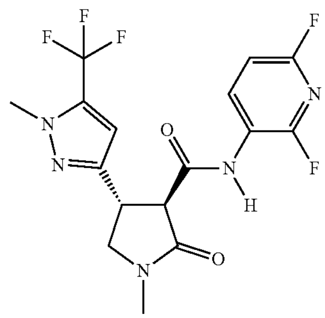 [SMILES: CN1C[C@H](c2cc(C(F)(F)F)n(C)n2)[C@@H](C(=O)Nc2ccc(F)nc2F)C1=O] |
| 2.9 | (3S,4R)-N-(6-fluoro-2-pyridyl)-1-methyl-4-[1-methyl-5-(trifluoromethyl)pyrazol-3-yl]-2-oxo-pyrrolidine-3-carboxamide | 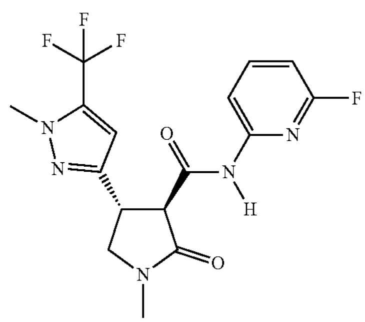 [SMILES: CN1C[C@H](c2cc(C(F)(F)F)n(C)n2)[C@@H](C(=O)Nc2cccc(F)n2)C1=O] |
| 2.10 | (3S,4R)-N-[2-(difluoromethoxy)-3-fluoro-phenyl]-1-methyl-4-[1-methyl-5-(trifluoromethyl)pyrazol-3-yl]-2-oxo-pyrrolidine-3-carboxamide | 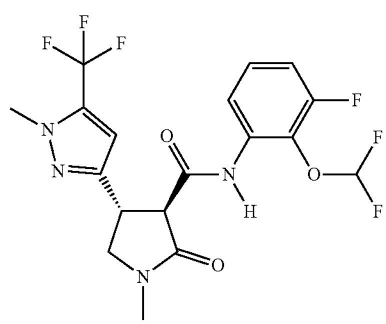 [SMILES: CN1C[C@H](c2cc(C(F)(F)F)n(C)n2)[C@@H](C(=O)Nc2cccc(F)c2OC(F)F)C1=O] |
| 2.11 | (3S,4R)-N-(2-ethylphenyl)-1-methyl-4-[1-methyl-5-(trifluoromethyl)pyrazol-3-yl]-2-oxo-pyrrolidine-3-carboxamide | 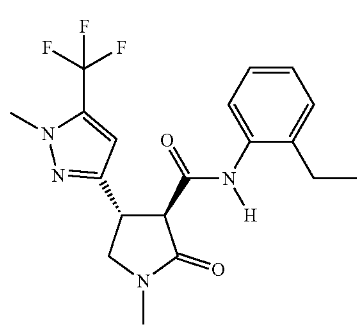 [SMILES: CCc1ccccc1NC(=O)[C@H]1C(=O)N(C)C[C@@H]1c1cc(C(F)(F)F)n(C)n1] |

TABLE 1-continued

Compounds of formula (II) for use in compositions described herein.

| Compound No. | Name | Structure |
|---|---|---|
| 2.12 | (3S,4R)-N-[2-(1,1-difluoroethyl)-3-fluoro-phenyl]-1-methyl-4-[1-methyl-5-(trifluoromethyl)pyrazol-3-yl]-2-oxo-pyrrolidine-3-carboxamide | 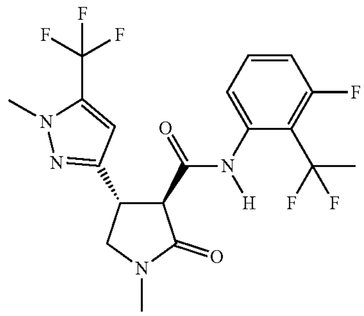 [SMILES: CN1C[C@H](c2cc(C(F)(F)F)n(C)n2)[C@@H](C(=O)Nc2cccc(F)c2C(C)(F)F)C1=O] |
| 2.13 | (3S,4R)-N-(2-chloro-3-thienyl)-1-methyl-4-[1-methyl-5-(trifluoromethyl)pyrazol-3-yl]-2-oxo-pyrrolidine-3-carboxamide | 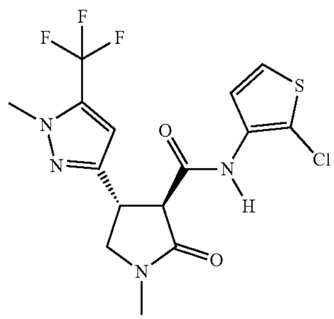 [SMILES: CN1C[C@H](c2cc(C(F)(F)F)n(C)n2)[C@@H](C(=O)Nc2ccsc2Cl)C1=O] |
| 2.14 | (3S,4R)-N-(2-fluoro-3-thienyl)-1-methyl-4-[1-methyl-5-(trifluoromethyl)pyrazol-3-yl]-2-oxo-pyrrolidine-3-carboxamide | 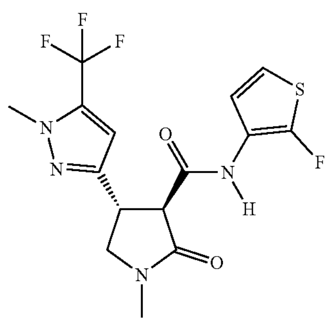 [SMILES: CN1C[C@H](c2cc(C(F)(F)F)n(C)n2)[C@@H](C(=O)Nc2ccsc2F)C1=O] |
| 2.15 | (3S,4S)-N-(2,3-difluorophenyl)-1-methyl-4-[1-methyl-5-(trifluoromethyl)pyrazol-4-yl]-2-oxo-pyrrolidine-3-carboxamide | 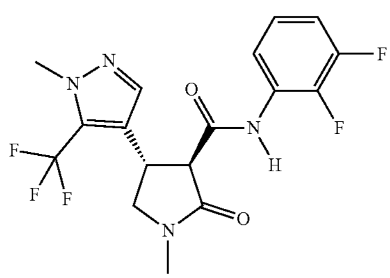 [SMILES: CN1C[C@H](c2cnn(C)c2C(F)(F)F)[C@@H](C(=O)Nc2cccc(F)c2F)C1=O] |
| 2.16 | (3S,4S)-N-(2-fluorophenyl)-1-methyl-4-[1-methyl-5-(trifluoromethyl)pyrazol-4-yl]-2-oxo-pyrrolidine-3-carboxamide | 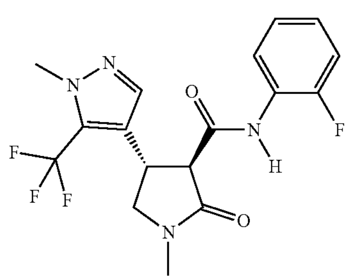 [SMILES: CN1C[C@H](c2cnn(C)c2C(F)(F)F)[C@@H](C(=O)Nc2ccccc2F)C1=O] |

TABLE 1-continued

Compounds of formula (II) for use in compositions described herein.

| Compound No. | Name | Structure |
|---|---|---|
| 2.17 | (3S,4S)-N-(2,4-difluorophenyl)-1-methyl-4-[1-methyl-5-(trifluoromethyl)pyrazol-4-yl]-2-oxo-pyrrolidine-3-carboxamide | 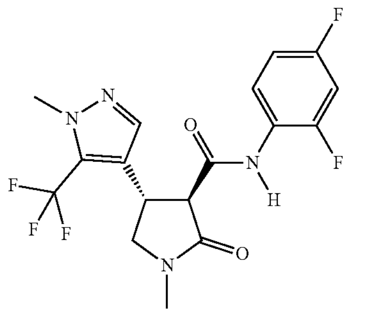 [SMILES: CN1C[C@H](c2cnn(C)c2C(F)(F)F)[C@@H](C(=O)Nc2ccc(F)cc2F)C1=O] |
| 2.18 | (3S,4S)-N-[3-fluoro-2-(trifluoromethyl)phenyl]-1-methyl-4-[1-methyl-5-(trifluoromethyl)pyrazol-4-yl]-2-oxo-pyrrolidine-3-carboxamide | 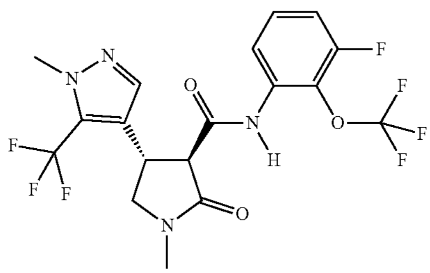 [SMILES: CN1C[C@H](c2cnn(C)c2C(F)(F)F)[C@@H](C(=O)Nc2cccc(F)c2OC(F)(F)F)C1=O] |
| 2.19 | (3S,4S)-N-[3-fluoro-2-(trifluoromethyl)phenyl]-1-methyl-4-[1-methyl-5-(trifluoromethyl)pyrazol-4-yl]-2-oxo-pyrrolidine-3-carboxamide | 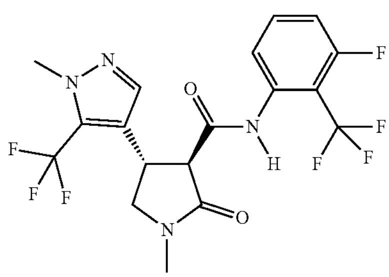 [SMILES: CN1C[C@H](c2cnn(C)c2C(F)(F)F)[C@@H](C(=O)Nc2cccc(F)c2C(F)(F)F)C1=O] |
| 2.20 | (3S,4S)-N-(3-fluoro-2-methoxy-phenyl)-1-methyl-4-[1-methyl-5-(trifluoromethyl)pyrazol-4-yl]-2-oxo-pyrrolidine-3-carboxamide | 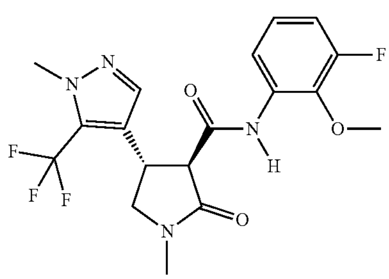 [SMILES: COc1c(F)cccc1NC(=O)[C@H]1C(=O)N(C)C[C@@H]1c1cnn(C)c1C(F)(F)F] |
| 2.21 | (3S,4S)-1-methyl-4-[1-methyl-5-(trifluoromethyl)pyrazol-4-yl]-2-oxo-N-(2,3,4-trifluorophenyl)pyrrolidine-3-carboxamide | 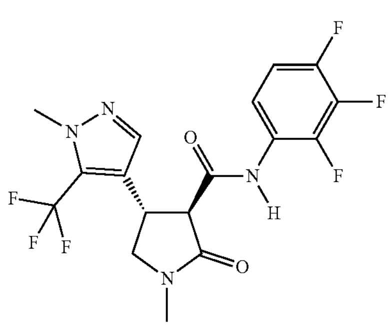 [SMILES: CN1C[C@H](c2cnn(C)c2C(F)(F)F)[C@@H](C(=O)Nc2ccc(F)c(F)c2F)C1=O] |

TABLE 1-continued

Compounds of formula (II) for use in compositions described herein.

| Compound No. | Name | Structure |
|---|---|---|
| 2.22 | (3S,4S)-N-(2,6-difluoro-3-pyridyl)-1-methyl-4-[1-methyl-5-(trifluoromethyl)pyrazol-4-yl]-2-oxo-pyrrolidine-3-carboxamide | 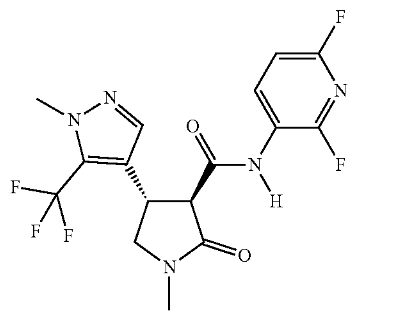 [SMILES: CN1C[C@H](c2cnn(C)c2C(F)(F)F)[C@@H](C(=O)Nc2ccc(F)nc2F)C1=O] |
| 2.23 | (3S,4S)-N-[2-(1,1-difluoroethyl)-3-fluoro-phenyl]-1-methyl-4-[1-methyl-5-(trifluoromethyl)pyrazol-4-yl]-2-oxo-pyrrolidine-3-carboxamide | 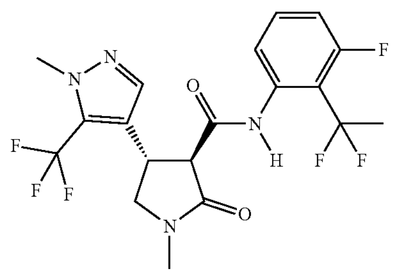 [SMILES: CN1C[C@H](c2cnn(C)c2C(F)(F)F)[C@@H](C(=O)Nc2cccc(F)c2C(C)(F)F)C1=O] |
| 2.24 | (3S,4S)-N-[2-(difluoromethoxy)-3-fluoro-phenyl]-1-methyl-4-[1-methyl-5-(trifluoromethyl)pyrazol-4-yl]-2-oxo-pyrrolidine-3-carboxamide | 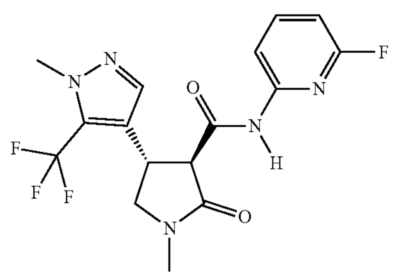 [SMILES: CN1C[C@H](c2cnn(C)c2C(F)(F)F)[C@@H](C(=O)Nc2cccc(F)n2)C1=O] |
| 2.25 | (3S,4S)-N-[2-(difluoromethoxy)-3-fluoro-phenyl]-1-methyl-4-[1-methyl-5-(trifluoromethyl)pyrazol-4-yl]-2-oxo-pyrrolidine-3-carboxamide | 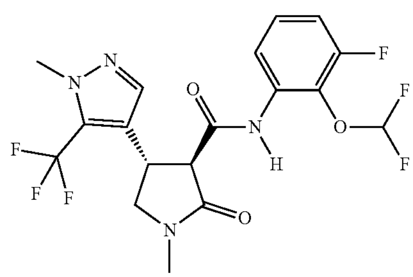 [SMILES: CN1C[C@H](c2cnn(C)c2C(F)(F)F)[C@@H](C(=O)Nc2cccc(F)c2OC(F)F)C1=O] |
| 2.26 | (3S,4S)-N-(2-ethylphenyl)-1-methyl-4-[1-methyl-5-(trifluoromethyl)pyrazol-4-yl]-2-oxo-pyrrolidine-3-carboxamide | 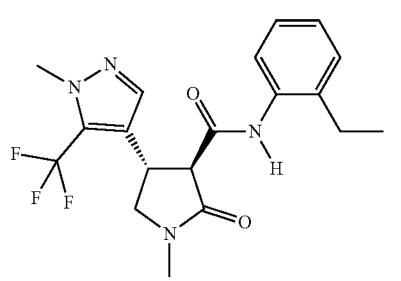 [SMILES: CCc1ccccc1NC(=O)[C@H]1C(=O)N(C)C[C@@H]1c1cnn(C)c1C(F)(F)F] |

TABLE 1-continued

Compounds of formula (II) for use in compositions described herein.

| Compound No. | Name | Structure |
|---|---|---|
| 2.27 | (3S,4R)-N-(2-chloro-3-thienyl)-1-methyl-4-[1-methyl-5-(trifluoromethyl)pyrazol-3-yl]-2-oxo-pyrrolidine-3-carboxamide | 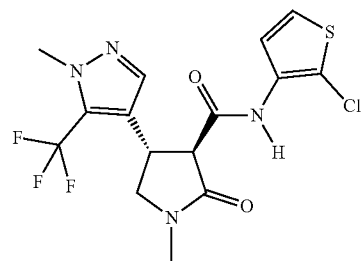 [SMILES: CN1C[C@H](c2cnn(C)c2C(F)(F)F)[C@@H](C(=O)Nc2ccsc2Cl)C1=O] |
| 2.28 | (3S,4S)-N-(2-fluoro-3-thienyl)-1-methyl-4-[1-methyl-5-(trifluoromethyl)pyrazol-4-yl]-2-oxo-pyrrolidine-3-carboxamide | 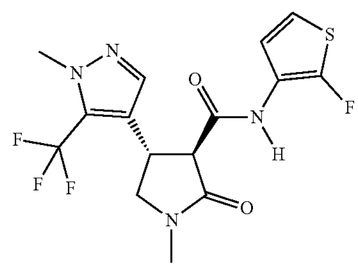 [SMILES: CN1C[C@H](c2cnn(C)c2C(F)(F)F)[C@@H](C(=O)Nc2ccsc2F)C1=O] |
| 2.29 | (3S,4R)-N-(2,3-difluorophenyl)-1-methyl-4-[2-methyl-5-(trifluoromethyl)pyrazol-3-yl]-2-oxo-pyrrolidine-3-carboxamide | 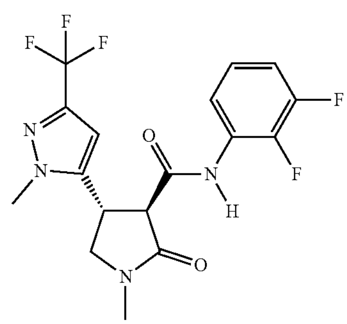 [SMILES: CN1C[C@H](c2cc(C(F)(F)F)nn2C)[C@@H](C(=O)Nc2cccc(F)c2F)C1=O] |
| 2.30 | (3S)-N-(2-fluorophenyl)-1-methyl-4-[2-methyl-5-(trifluoromethyl)pyrazol-3-yl]-2-oxo-pyrrolidine-3-carboxamide | 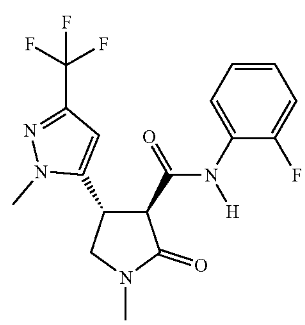 [SMILES: CN1C[C@H](c2cc(C(F)(F)F)nn2C)[C@@H](C(=O)Nc2ccccc2F)C1=O] |
| 2.31 | (3S,4R)-N-(2,4-difluorophenyl)-1-methyl-4-[2-methyl-5-(trifluoromethyl)pyrazol-3-yl]-2-oxo-pyrrolidine-3-carboxamide | 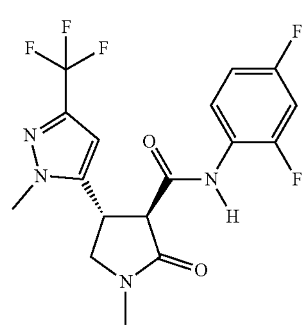 [SMILES: CN1C[C@H](c2cc(C(F)(F)F)nn2C)[C@@H](C(=O)Nc2ccc(F)cc2F)C1=O] |

TABLE 1-continued

Compounds of formula (II) for use in compositions described herein.

| Compound No. | Name | Structure |
|---|---|---|
| 2.32 | (3S,4R)-N-[3-fluoro-2-(trifluoromethoxy)phenyl]-1-methyl-4-[2-methyl-5-(trifluoromethyl)pyrazol-3-yl]-2-oxo-pyrrolidine-3-carboxamide | 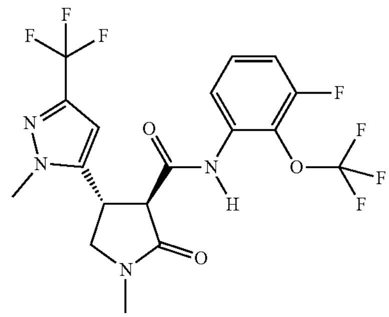 [SMILES: CN1C[C@H](c2cc(C(F)(F)F)nn2C)[C@@H](C(=O)Nc2cccc(F)c2OC(F)(F)F)C1=O] |
| 2.33 | (3S,4R)-N-[3-fluoro-2-(trifluoromethyl)phenyl]-1-methyl-4-[2-methyl-5-(trifluoromethyl)pyrazol-3-yl]-2-oxo-pyrrolidine-3-carboxamide | 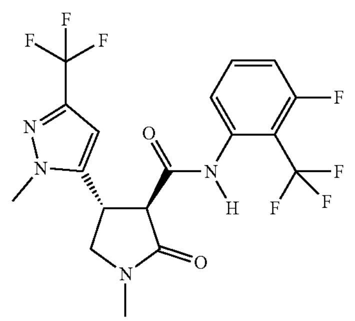 [SMILES: CN1C[C@H](c2cc(C(F)(F)F)nn2C)[C@@H](C(=O)Nc2cccc(F)c2C(F)(F)F)C1=O] |
| 2.34 | (3S,4R)-N-(3-fluoro-2-methoxy-phenyl)-1-methyl-4-[2-methyl-5-(trifluoromethyl)pyrazol-3-yl]-2-oxo-pyrrolidine-3-carboxamide | 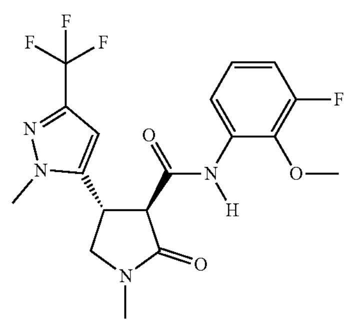 |
| 2.35 | (3S,4R)-1-methyl-4-[2-methyl-5-(trifluoromethyl)pyrazol-3-yl]-2-oxo-N-(2,3,4-trifluorophenyl)pyrrolidine-3-carboxamide | 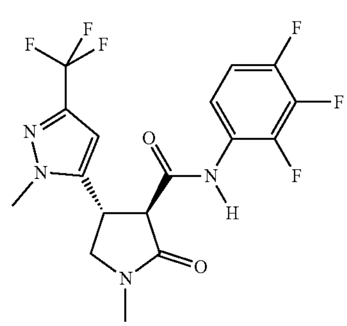 [SMILES: CN1C[C@H](c2cc(C(F)(F)F)nn2C)[C@@H](C(=O)Nc2ccc(F)c(F)c2F)C1=O] |

TABLE 1-continued

Compounds of formula (II) for use in compositions described herein.

| Compound No. | Name | Structure |
|---|---|---|
| 2.36 | (3S,4R)-N-(2,6-difluoro-3-pyridyl)-1-methyl-4-[1-methyl-3-(trifluoromethyl)-3H-pyrazol-5-yl]-2-oxo-pyrrolidine-3-carboxamide | 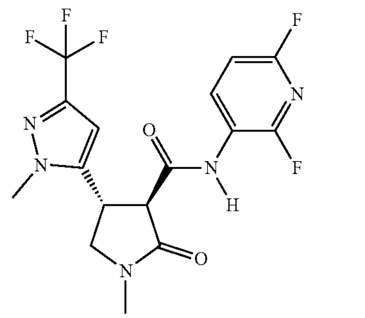 [SMILES: CN1C[C@H](c2cc(C(F)(F)F)nn2C)[C@@H](C(=O)Nc2ccc(F)nc2F)C1=O] |
| 2.37 | (3S,4R)-N-(6-fluoro-2-pyridyl)-1-methyl-4-[1-methyl-3-(trifluoromethyl)-3H-pyrazol-5-yl]-2-oxo-pyrrolidine-3-carboxamide | 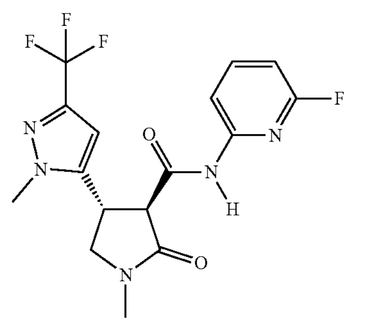 [SMILES: CN1C[C@H](c2cc(C(F)(F)F)nn2C)[C@@H](C(=O)Nc2cccc(F)n2)C1=O] |
| 2.38 | (3S,4R)-N-[2-(difluoromethoxy)-3-fluoro-phenyl]-1-methyl-4-[1-methyl-3-(trifluoromethyl)-3H-pyrazol-5-yl]-2-oxo-pyrrolidine-3-carboxamide | 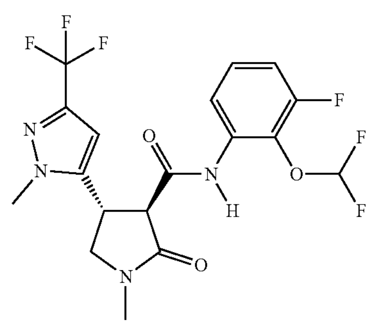 [SMILES: CN1C[C@H](c2cc(C(F)(F)F)nn2C)[C@@H](C(=O)Nc2cccc(F)c2OC(F)F)C1=O] |
| 2.39 | (3S,4R)-N-(2-ethylphenyl)-1-methyl-4-[1-methyl-3-(trifluoromethyl)-3H-pyrazol-5-yl]-2-oxo-pyrrolidine-3-carboxamide | 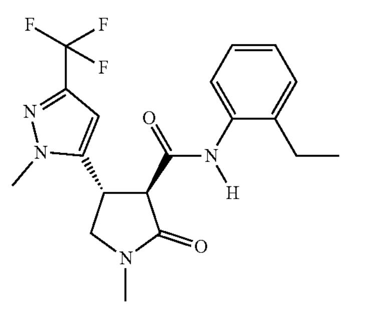 [SMILES: CCc1ccccc1NC(=O)[C@H]1C(=O)N(C)C[C@@H]1c1cc(C(F)(F)F)nn1C] |

TABLE 1-continued

Compounds of formula (II) for use in compositions described herein.

| Compound No. | Name | Structure |
|---|---|---|
| 2.40 | (3S,4R)-N-[2-(1,1-difluoroethyl)-3-fluoro-phenyl]-1-methyl-4-[1-methyl-3-(trifluoromethyl)-3H-pyrazol-5-yl]-2-oxo-pyrrolidine-3-carboxamide | 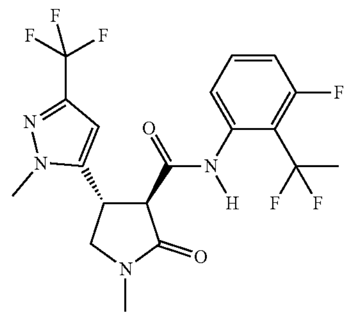 [SMILES: CN1C[C@H](c2cc(C(F)(F)F)nn2C)[C@@H](C(=O)Nc2cccc(F)c2C(C)(F)F)C1=O] |
| 2.41 | (3S,4R)-N-(2-chloro-3-thienyl)-1-methyl-4-[1-methyl-3-(trifluoromethyl)-3H-pyrazol-5-yl]-2-oxo-pyrrolidine-3-carboxamide | 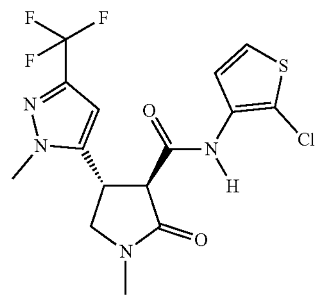 [SMILES: CN1C[C@H](c2cc(C(F)(F)F)nn2C)[C@@H](C(=O)Nc2ccsc2Cl)C1=O] |
| 2.42 | (3S,4R)-N-(2-fluoro-3-thienyl)-1-methyl-4-[1-methyl-3-(trifluoromethyl)-3H-pyrazol-5-yl]-2-oxo-pyrrolidine-3-carboxamide | 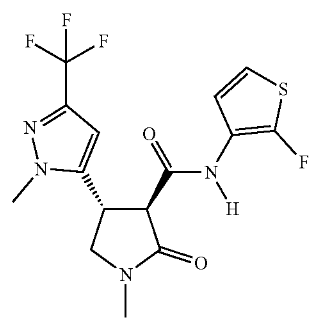 [SMILES: CN1C[C@H](c2cc(C(F)(F)F)nn2C)[C@@H](C(=O)Nc2ccsc2F)C1=O] |
| 2.43 | (3S,4R)-4-(5-chloro-1-methyl-pyrazol-3-yl)-N-(2,3-difluorophenyl)-1-methyl-2-oxo-pyrrolidine-3-carboxamide | 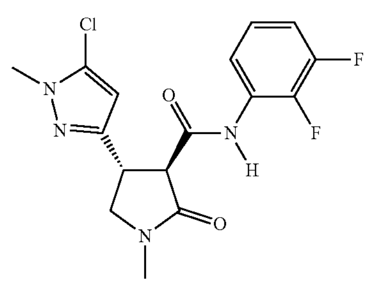 [SMILES: CN1C[C@H](c2cc(Cl)n(C)n2)[C@@H](C(=O)Nc2cccc(F)c2F)C1=O] |
| 2.44 | (3S,4R)-4-(5-chloro-1-methyl-pyrazol-3-yl)-N-(2-fluorophenyl)-1-methyl-2-oxo-pyrrolidine-3-carboxamide | 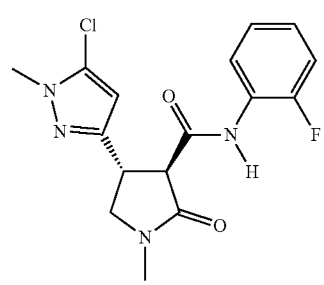 [SMILES: CN1C[C@H](c2cc(Cl)n(C)n2)[C@@H](C(=O)Nc2ccccc2F)C1=O] |

TABLE 1-continued

Compounds of formula (II) for use in compositions described herein.

| Compound No. | Name | Structure |
| --- | --- | --- |
| 2.45 | (3S,4R)-4-(5-chloro-1-methyl-pyrazol-3-yl)-N-(2,4-difluorophenyl)-1-methyl-2-oxo-pyrrolidine-3-carboxamide | 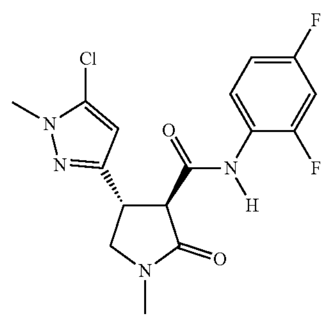 [SMILES: CN1C[C@H](c2cc(Cl)n(C)n2)[C@@H](C(=O)Nc2ccc(F)cc2F)C1=O] |
| 2.46 | (3S,4R)-4-(5-chloro-1-methyl-pyrazol-3-yl)-N-[3-fluoro-2-(trifluoromethoxy)phenyl]-1-methyl-2-oxo-pyrrolidine-3-carboxamide | 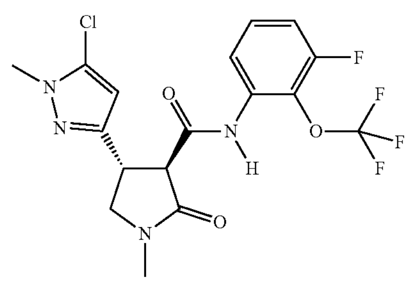 [SMILES: CN1C[C@H](c2cc(Cl)n(C)n2)[C@@H](C(=O)Nc2cccc(F)c2OC(F)(F)F)C1=O] |
| 2.47 | (3S,4R)-4-(5-chloro-1-methyl-pyrazol-3-yl)-N-[3-fluoro-2-(trifluoromethyl)phenyl]-1-methyl-2-oxo-pyrrolidine-3-carboxamide | 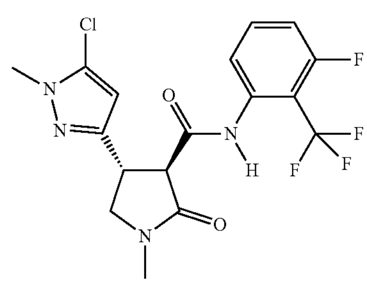 [SMILES: CN1C[C@H](c2cc(Cl)n(C)n2)[C@@H](C(=O)Nc2cccc(F)c2C(F)(F)F)C1=O] |
| 2.48 | (3S,4R)-4-(5-chloro-1-methyl-pyrazol-3-yl)-N-(3-fluoro-2-methoxy-phenyl)-1-methyl-2-oxo-pyrrolidine-3-carboxamide | 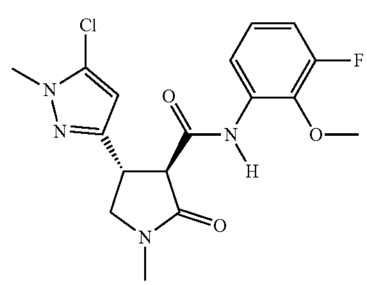 |
| 2.49 | (3S,4R)-4-(5-chloro-1-methyl-pyrazol-3-yl)-1-methyl-2-oxo-N-(2,3,4-trifluorophenyl)pyrrolidine-3-carboxamide | 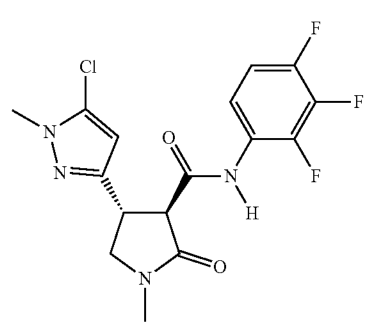 [SMILES: CN1C[C@H](c2cc(Cl)n(C)n2)[C@@H](C(=O)Nc2ccc(F)c(F)c2F)C1=O] |

TABLE 1-continued

Compounds of formula (II) for use in compositions described herein.

| Compound No. | Name | Structure |
|---|---|---|
| 2.50 | (3S,4R)-4-(5-chloro-1-methyl-pyrazol-3-yl)-N-(2,6-difluoro-3-pyridyl)-1-methyl-2-oxo-pyrrolidine-3-carboxamide | 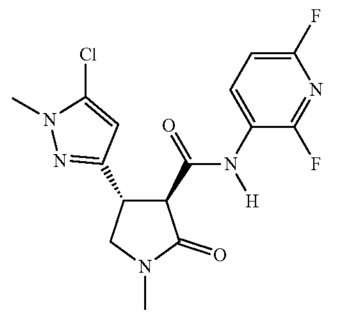 [SMILES: CN1C[C@H](c2cc(Cl)n(C)n2)[C@@H](C(=O)Nc2ccc(F)nc2F)C1=O] |
| 2.51 | (3S,4R)-4-(5-chloro-1-methyl-pyrazol-3-yl)-N-(6-fluoro-2-pyridyl)-1-methyl-2-oxo-pyrrolidine-3-carboxamide | 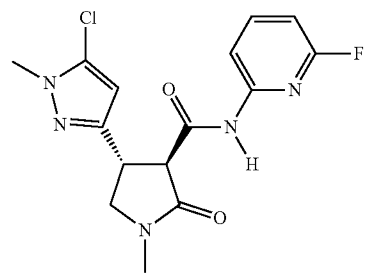 [SMILES: CN1C[C@H](c2cc(Cl)n(C)n2)[C@@H](C(=O)Nc2cccc(F)n2)C1=O] |
| 2.52 | (3S,4R)-4-(5-chloro-1-methyl-pyrazol-3-yl)-N-[2-(difluoromethoxy)-3-fluoro-phenyl]-1-methyl-2-oxo-pyrrolidine-3-carboxamide | 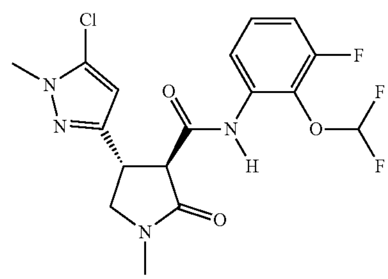 [SMILES: CN1C[C@H](c2cc(Cl)n(C)n2)[C@@H](C(=O)Nc2cccc(F)c2OC(F)F)C1=O] |
| 2.53 | (3S,4R)-4-(5-chloro-1-methyl-pyrazol-3-yl)-N-(2-ethylphenyl)-1-methyl-2-oxo-pyrrolidine-3-carboxamide | 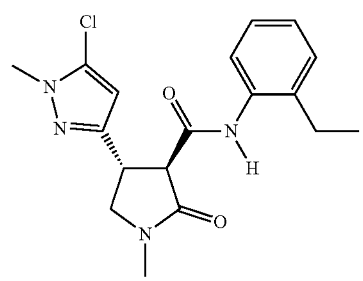 [SMILES: CCc1ccccc1NC(=O)[C@H]1C(=O)N(C)C[C@@H]1c1cc(Cl)n(C)n1] |
| 2.54 | (3S,4R)-4-(4-bromo-5-chloro-1-methyl-pyrazol-3-yl)-N-[2-(1,1-difluoroethyl)-3-fluoro-phenyl]-1-methyl-2-oxo-pyrrolidine-3-carboxamide | 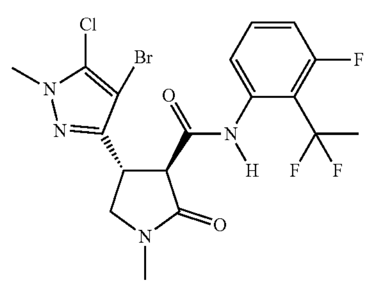 [SMILES: CN1C[C@H](c2nn(C)c(Cl)c2Br)[C@@H](C(=O)Nc2cccc(F)c2C(C)(F)F)C1=O] |

TABLE 1-continued

Compounds of formula (II) for use in compositions described herein.

| Compound No. | Name | Structure |
|---|---|---|
| 2.55 | (3S,4R)-4-(5-chloro-1-methyl-pyrazol-3-yl)-N-(2-chloro-3-thienyl)-1-methyl-2-oxo-pyrrolidine-3-carboxamide | 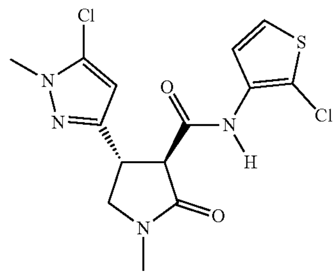 [SMILES: CN1C[C@H](c2cc(Cl)n(C)n2)[C@@H](C(=O)Nc2ccsc2Cl)C1=O] |
| 2.56 | (3S,4R)-4-(5-chloro-1-methyl-pyrazol-3-yl)-N-(2-fluoro-3-thienyl)-1-methyl-2-oxo-pyrrolidine-3-carboxamide | 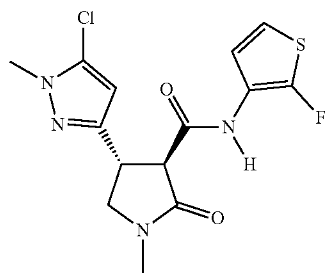 [SMILES: CN1C[C@H](c2cc(Cl)n(C)n2)[C@@H](C(=O)Nc2ccsc2F)C1=O] |
| 2.57 | (3S,4S)-4-(5-chloro-1-methyl-pyrazol-4-yl)-N-(2,3-difluorophenyl)-1-methyl-2-oxo-pyrrolidine-3-carboxamide | 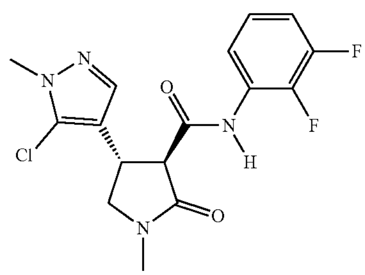 [SMILES: CN1C[C@H](c2cnn(C)c2Cl)[C@@H](C(=O)Nc2cccc(F)c2F)C1=O] |
| 2.58 | (3S,4S)-4-(5-chloro-1-methyl-pyrazol-4-yl)-N-(2-fluorophenyl)-1-methyl-2-oxo-pyrrolidine-3-carboxamide | 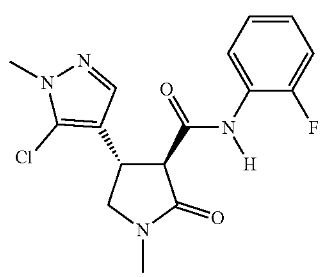 [SMILES: CN1C[C@H](c2cnn(C)c2Cl)[C@@H](C(=O)Nc2ccccc2F)C1=O] |
| 2.59 | (3S,4S)-4-(5-chloro-1-methyl-pyrazol-4-yl)-N-(2,4-difluorophenyl)-1-methyl-2-oxo-pyrrolidine-3-carboxamide | 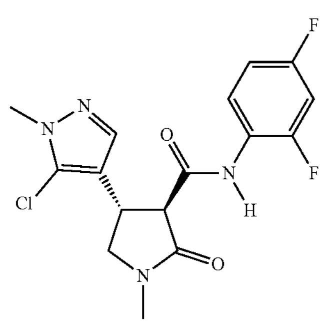 [SMILES: CN1C[C@H](c2cnn(C)c2Cl)[C@@H](C(=O)Nc2ccc(F)cc2F)C1=O] |

TABLE 1-continued

Compounds of formula (II) for use in compositions described herein.

| Compound No. | Name | Structure |
|---|---|---|
| 2.60 | (3S,4S)-4-(5-chloro-1-methyl-pyrazol-4-yl)-N-[3-fluoro-2-(trifluoromethoxy)phenyl]-1-methyl-2-oxo-pyrrolidine-3-carboxamide | 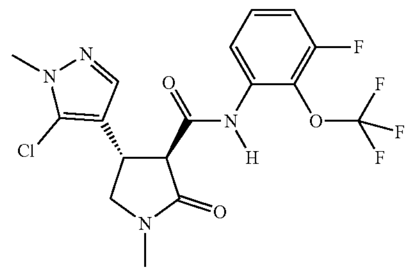 [SMILES: CN1C[C@H](c2cnn(C)c2Cl)[C@@H](C(=O)Nc2cccc(F)c2OC(F)(F)F)C1=O] |
| 2.61 | (3S,4S)-4-(5-chloro-1-methyl-pyrazol-4-yl)-N-[3-fluoro-2-(trifluoromethyl)phenyl]-1-methyl-2-oxo-pyrrolidine-3-carboxamide | 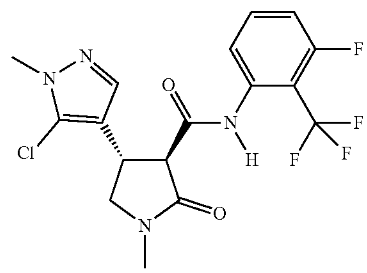 [SMILES: CN1C[C@H](c2cnn(C)c2Cl)[C@@H](C(=O)Nc2cccc(F)c2C(F)(F)F)C1=O] |
| 2.62 | (3S,4S)-4-(5-chloro-1-methyl-pyrazol-4-yl)-N-(3-fluoro-2-methoxy-phenyl)-1-methyl-2-oxo-pyrrolidine-3-carboxamide | 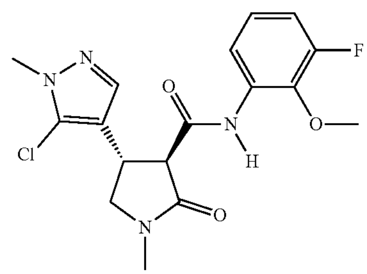 |
| 2.63 | (3S,4S)-4-(5-chloro-1-methyl-pyrazol-4-yl)-1-methyl-2-oxo-N-(2,3,4-trifluorophenyl)pyrrolidine-3-carboxamide | 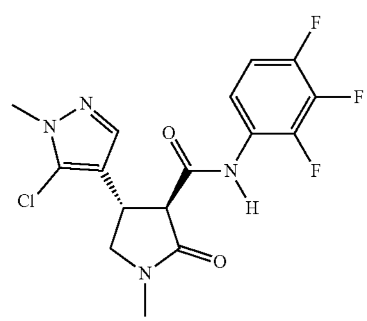 [SMILES: CN1C[C@H](c2cnn(C)c2Cl)[C@@H](C(=O)Nc2ccc(F)c(F)c2F)C1=O] |
| 2.64 | (3S,4S)-4-(3-bromo-5-chloro-1-methyl-pyrazol-4-yl)-N-(2,6-difluoro-3-pyridyl)-1-methyl-2-oxo-pyrrolidine-3-carboxamide | 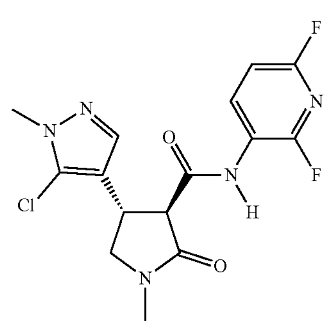 [SMILES: CN1C[C@H](c2cnn(C)c2Cl)[C@@H](C(=O)Nc2ccc(F)nc2F)C1=O] |

TABLE 1-continued

Compounds of formula (II) for use in compositions described herein.

| Compound No. | Name | Structure |
|---|---|---|
| 2.65 | (3S,4S)-4-(5-chloro-1-methyl-pyrazol-4-yl)-N-(6-fluoro-2-pyridyl)-1-methyl-2-oxo-pyrrolidine-3-carboxamide | 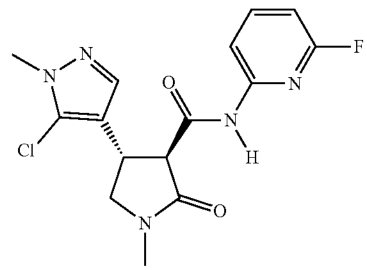 [SMILES: CN1C[C@H](c2cnn(C)c2Cl)[C@@H](C(=O)Nc2cccc(F)n2)C1=O] |
| 2.66 | (3S,4S)-4-(5-chloro-1-methyl-pyrazol-4-yl)-N-[2-(difluoromethoxy)-3-fluoro-phenyl]-1-methyl-2-oxo-pyrrolidine-3-carboxamide | 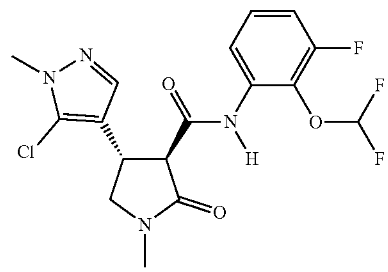 [SMILES: CN1C[C@H](c2cnn(C)c2Cl)[C@@H](C(=O)Nc2cccc(F)c2OC(F)F)C1=O] |
| 2.67 | (3S,4S)-4-(5-chloro-1-methyl-pyrazol-4-yl)-N-(2-ethylphenyl)-1-methyl-2-oxo-pyrrolidine-3-carboxamide | 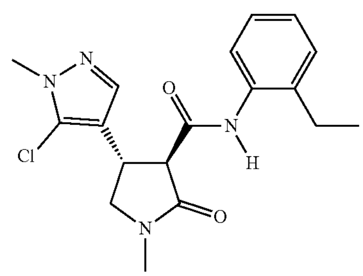 [SMILES: CCc1ccccc1NC(=O)[C@H]1C(=O)N(C)C[C@@H]1c1cnn(C)c1Cl] |
| 2.68 | (3S,4S)-4-(5-chloro-1-methyl-pyrazol-4-yl)-N-[2-(1,1-difluoroethyl)-3-fluoro-phenyl]-1-methyl-2-oxo-pyrrolidine-3-carboxamide | 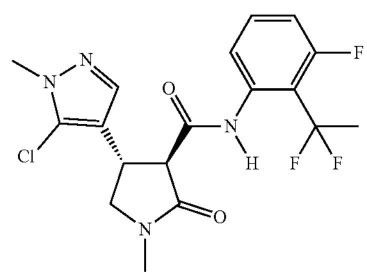 [SMILES: CN1C[C@H](c2cnn(C)c2Cl)[C@@H](C(=O)Nc2cccc(F)c2C(C)(F)F)C1=O] |
| 2.69 | (3S,4S)-4-(5-chloro-1-methyl-pyrazol-4-yl)-N-(2-chloro-3-thienyl)-1-methyl-2-oxo-pyrrolidine-3-carboxamide | 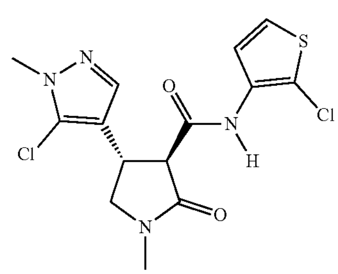 [SMILES: CN1C[C@H](c2cnn(C)c2Cl)[C@@H](C(=O)Nc2ccsc2Cl)C1=O] |

TABLE 1-continued

Compounds of formula (II) for use in compositions described herein.

| Compound No. | Name | Structure |
|---|---|---|
| 2.70 | (3S,4S)-4-(5-chloro-1-methyl-pyrazol-4-yl)-N-(2-fluoro-3-thienyl)-1-methyl-2-oxo-pyrrolidine-3-carboxamide | 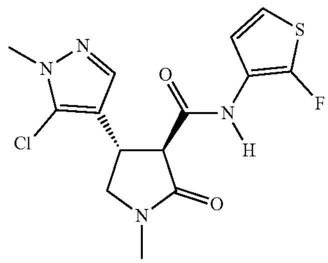 [SMILES: CN1C[C@H](c2cnn(C)c2Cl)[C@@H](C(=O)Nc2ccsc2F)C1=O] |
| 2.71 | (3S,4R)-4-(5-chloro-2-methyl-pyrazol-3-yl)-N-(2,3-difluorophenyl)-1-methyl-2-oxo-pyrrolidine-3-carboxamide | 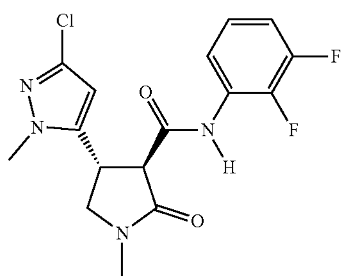 [SMILES: CN1C[C@H](c2cc(Cl)nn2C)[C@@H](C(=O)Nc2cccc(F)c2F)C1=O] |
| 2.72 | (3S)-4-(5-chloro-2-methyl-pyrazol-3-yl)-N-(2-fluorophenyl)-1-methyl-2-oxo-pyrrolidine-3-carboxamide | 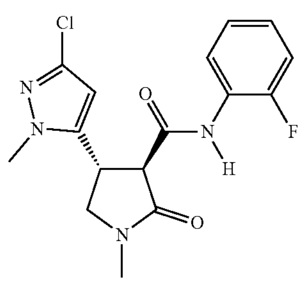 [SMILES: CN1C[C@H](c2cc(Cl)nn2C)[C@@H](C(=O)Nc2ccccc2F)C1=O] |
| 2.73 | (3S,4R)-4-(5-chloro-2-methyl-pyrazol-3-yl)-N-(2,4-difluorophenyl)-1-methyl-2-oxo-pyrrolidine-3-carboxamide | 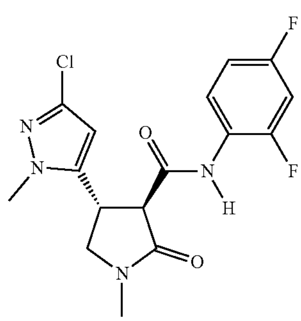 [SMILES: CN1C[C@H](c2cc(Cl)nn2C)[C@@H](C(=O)Nc2ccc(F)cc2F)C1=O] |
| 2.74 | (3S,4R)-4-(5-chloro-2-methyl-pyrazol-3-yl)-N-[3-fluoro-2-(trifluoromethoxy)phenyl]-1-methyl-2-oxo-pyrrolidine-3-carboxamide | 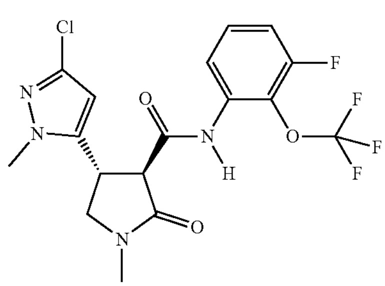 [SMILES: CN1C[C@H](c2cc(Cl)nn2C)[C@@H](C(=O)Nc2cccc(F)c2OC(F)(F)F)C1=O] |

TABLE 1-continued

Compounds of formula (II) for use in compositions described herein.

| Compound No. | Name | Structure |
|---|---|---|
| 2.75 | (3S,4R)-4-(5-chloro-2-methyl-pyrazol-3-yl)-N-[3-fluoro-2-(trifluoromethyl)phenyl]-1-methyl-2-oxo-pyrrolidine-3-carboxamide | 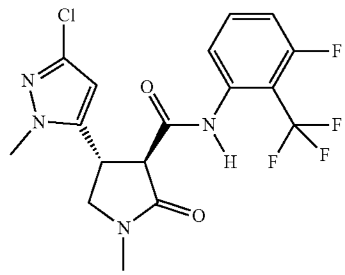 [SMILES: CN1C[C@H](c2cc(Cl)nn2C)[C@@H](C(=O)Nc2cccc(F)c2C(F)(F)F)C1=O] |
| 2.76 | (3S,4R)-4-(5-chloro-2-methyl-pyrazol-3-yl)-N-(3-fluoro-2-methoxy-phenyl)-1-methyl-2-oxo-pyrrolidine-3-carboxamide | 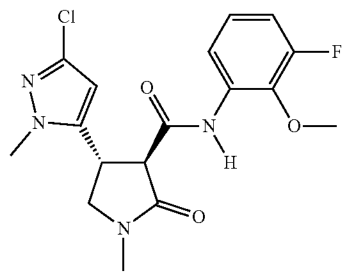 |
| 2.77 | (3S,4R)-1-methyl-4-[2-methyl-5-(trifluoromethyl)pyrazol-3-yl]-2-oxo-N-(2,3,4-trifluorophenyl)pyrrolidine-3-carboxamide | 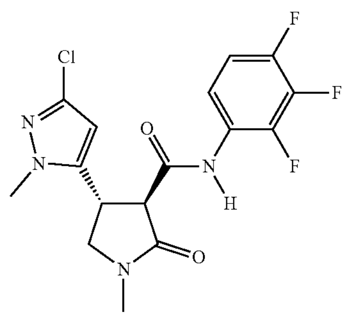 [SMILES: CN1C[C@H](c2cc(Cl)nn2C)[C@@H](C(=O)Nc2ccc(F)c(F)c2F)C1=O] |
| 2.78 | (3S,4R)-N-(2,6-difluoro-3-pyridyl)-1-methyl-4-[1-methyl-3-(chorol)-3H-pyrazol-5-yl]-2-oxo-pyrrolidine-3-carboxamide | 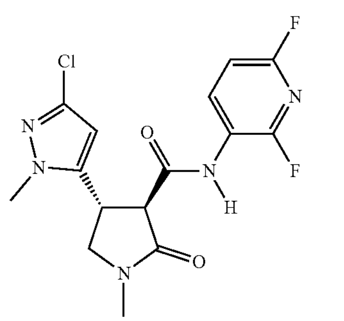 [SMILES: CN1C[C@H](c2cc(Cl)nn2C)[C@@H](C(=O)Nc2ccc(F)nc2F)C1=O] |
| 2.79 | (3S,4R)-N-(6-fluoro-2-pyridyl)-1-methyl-4-[1-methyl-3-(chloro)-3H-pyrazol-5-yl]-2-oxo-pyrrolidine-3-carboxamide | 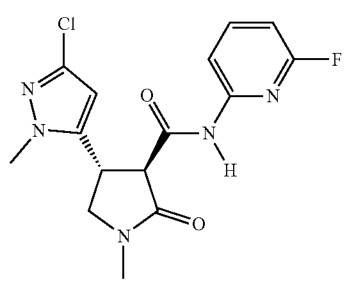 [SMILES: CN1C[C@H](c2cc(Cl)nn2C)[C@@H](C(=O)Nc2cccc(F)n2)C1=O] |

TABLE 1-continued

Compounds of formula (II) for use in compositions described herein.

| Compound No. | Name | Structure |
|---|---|---|
| 2.80 | (3S,4R)-N-[2-(difluoromethoxy)-3-fluoro-phenyl]-1-methyl-4-[1-methyl-3-(chloro)-3H-pyrazol-5-yl]-2-oxo-pyrrolidine-3-carboxamide | 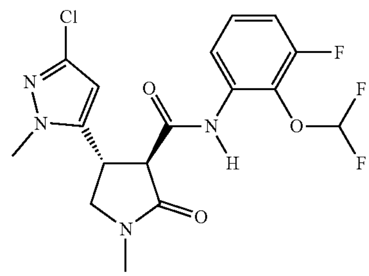 [SMILES: CN1C[C@H](c2cc(Cl)nn2C)[C@@H](C(=O)Nc2cccc(F)c2OC(F)F)C1=O] |
| 2.81 | (3S,4R)-N-(2-ethylphenyl)-1-methyl-4-[1-methyl-3-(chloro)-3H-pyrazol-5-yl]-2-oxo-pyrrolidine-3-carboxamide | 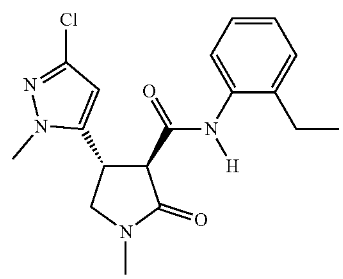 [SMILES: CCc1ccccc1NC(=O)[C@H]1C(=O)N(C)C[C@@H]1c1cc(Cl)nn1C] |
| 2.82 | (3S,4R)-N-[2-(1,1-difluoroethyl)-3-fluoro-phenyl]-1-methyl-4-[1-methyl-3-(chloro)-3H-pyrazol-5-yl]-2-oxo-pyrrolidine-3-carboxamide | 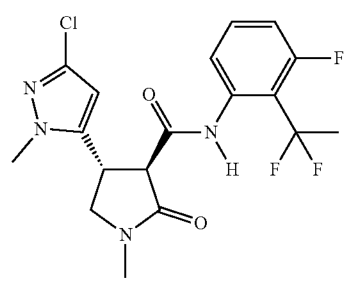 [SMILES: CN1C[C@H](c2cc(Cl)nn2C)[C@@H](C(=O)Nc2cccc(F)c2C(C)(F)F)C1=O] |
| 2.83 | (3S,4R)-N-(2-chloro-3-thienyl)-1-methyl-4-[1-methyl-3-(chloro)-3H-pyrazol-5-yl]-2-oxo-pyrrolidine-3-carboxamide | 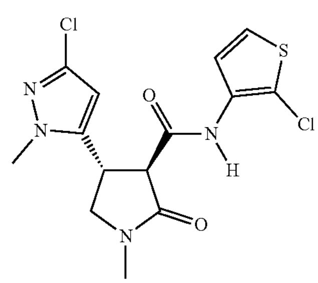 [SMILES: CN1C[C@H](c2cc(Cl)nn2C)[C@@H](C(=O)Nc2ccsc2Cl)C1=O] |
| 2.84 | (3S,4R)-N-(2-fluoro-3-thienyl)-1-methyl-4-[1-methyl-3-(chloro)-3H-pyrazol-5-yl]-2-oxo-pyrrolidine-3-carboxamide | 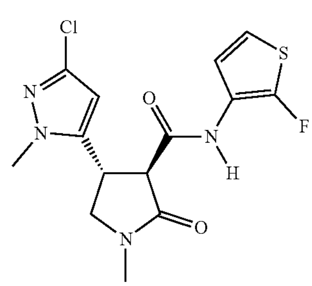 [SMILES: CN1C[C@H](c2cc(Cl)nn2C)[C@@H](C(=O)Nc2ccsc2F)C1=O] |

TABLE 1-continued

Compounds of formula (II) for use in compositions described herein.

| Compound No. | Name | Structure |
|---|---|---|
| 2.85 | (3S,4R)-4-(4-bromo-5-chloro-1-methyl-pyrazol-3-yl)-N-(2,3-difluorophenyl)-1-methyl-2-oxo-pyrrolidine-3-carboxamide | 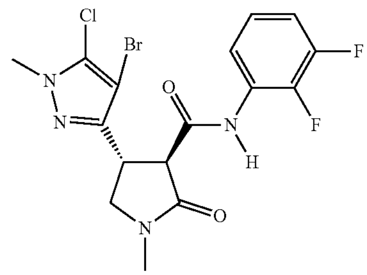 [SMILES: CN1C[C@H](c2nn(C)c(Cl)c2Br)[C@@H](C(=O)Nc2cccc(F)c2F)C1=O] |
| 2.86 | (3S,4R)-4-(4-bromo-5-chloro-1-methyl-pyrazol-3-yl)-N-(2-fluorophenyl)-1-methyl-2-oxo-pyrrolidine-3-carboxamide | 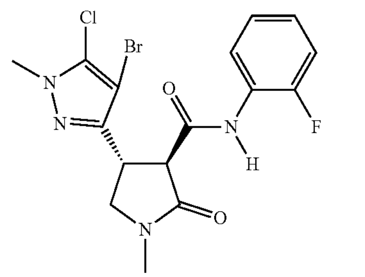 [SMILES: CN1C[C@H](c2nn(C)c(Cl)c2Br)[C@@H](C(=O)Nc2ccccc2F)C1=O] |
| 2.87 | (3S,4R)-4-(4-bromo-5-chloro-1-methyl-pyrazol-3-yl)-N-(2,4-difluorophenyl)-1-methyl-2-oxo-pyrrolidine-3-carboxamide | 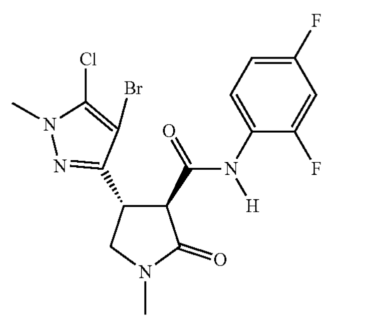 [SMILES: CN1C[C@H](c2nn(C)c(Cl)c2Br)[C@@H](C(=O)Nc2ccc(F)cc2F)C1=O] |
| 2.88 | (3S,4R)-4-(4-bromo-5-chloro-1-methyl-pyrazol-3-yl)-N-[3-fluoro-2-(trifluoromethoxy)phenyl]-1-methyl-2-oxo-pyrrolidine-3-carboxamide | 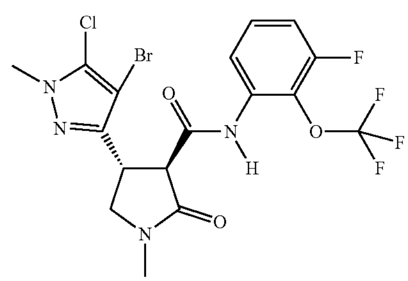 [SMILES: CN1C[C@H](c2nn(C)c(Cl)c2Br)[C@@H](C(=O)Nc2cccc(F)c2OC(F)(F)F)C1=O] |
| 2.89 | (3S,4R)-4-(4-bromo-5-chloro-1-methyl-pyrazol-3-yl)-N-[3-fluoro-2-(trifluoromethyl)phenyl]-1-methyl-2-oxo-pyrrolidine-3-carboxamide | 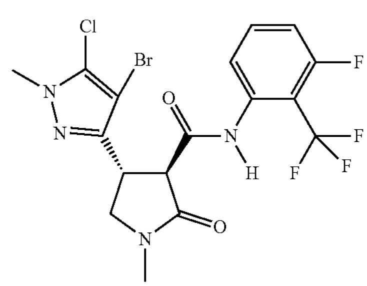 [SMILES: CN1C[C@H](c2nn(C)c(Cl)c2Br)[C@@H](C(=O)Nc2cccc(F)c2C(F)(F)F)C1=O] |

TABLE 1-continued

Compounds of formula (II) for use in compositions described herein.

| Compound No. | Name | Structure |
|---|---|---|
| 2.90 | (3S,4R)-4-(4-bromo-5-chloro-1-methyl-pyrazol-3-yl)-N-(3-fluoro-2-methoxy-phenyl)-1-methyl-2-oxo-pyrrolidine-3-carboxamide | 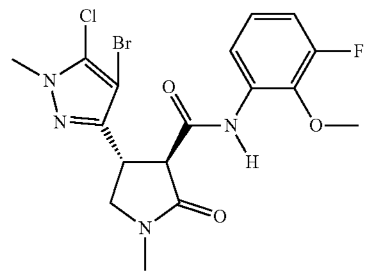 |
| 2.91 | (3S,4R)-4-(4-bromo-5-chloro-1-methyl-pyrazol-3-yl)-1-methyl-2-oxo-N-(2,3,4-trifluorophenyl)pyrrolidine-3-carboxamide | 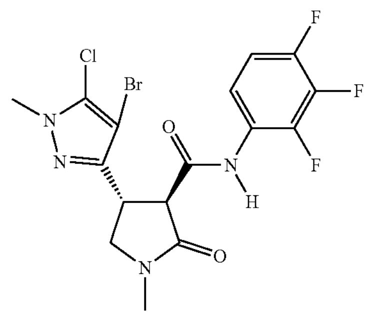 [SMILES: CN1C[C@H](c2nn(C)c(Cl)c2Br)[C@@H](C(=O)Nc2ccc(F)c(F)c2F)C1=O] |
| 2.92 | (3S,4R)-4-(4-bromo-5-chloro-1-methyl-pyrazol-3-yl)-N-(2,6-difluoro-3-pyridyl)-1-methyl-2-oxo-pyrrolidine-3-carboxamide | 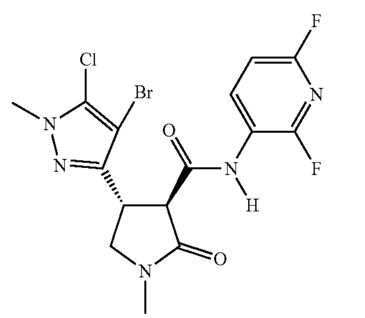 [SMILES: CN1C[C@H](c2nn(C)c(Cl)c2Br)[C@@H](C(=O)Nc2ccc(F)nc2F)C1=O] |
| 2.93 | (3S,4R)-4-(4-bromo-5-chloro-1-methyl-pyrazol-3-yl)-N-(6-fluoro-2-pyridyl)-1-methyl-2-oxo-pyrrolidine-3-carboxamide | 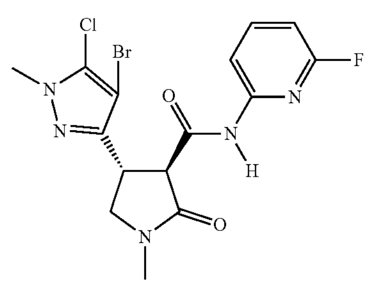 [SMILES: CN1C[C@H](c2nn(C)c(Cl)c2Br)[C@@H](C(=O)Nc2cccc(F)n2)C1=O] |
| 2.94 | (3S,4R)-4-(4-bromo-5-chloro-1-methyl-pyrazol-3-yl)-N-[2-(difluoromethoxy)-3-fluoro-phenyl]-1-methyl-2-oxo-pyrrolidine-3-carboxamide | 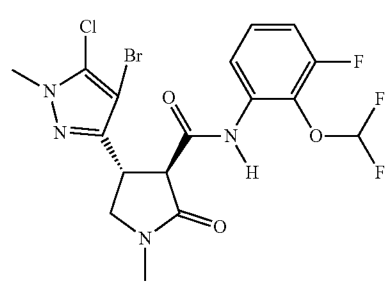 [SMILES: CN1C[C@H](c2nn(C)c(Cl)c2Br)[C@@H](C(=O)Nc2cccc(F)c2OC(F)F)C1=O] |

TABLE 1-continued

Compounds of formula (II) for use in compositions described herein.

| Compound No. | Name | Structure |
| --- | --- | --- |
| 2.95 | ((3S,4R)-4-(4-bromo-5-chloro-1-methyl-pyrazol-3-yl)-N-(2-ethylphenyl)-1-methyl-2-oxo-pyrrolidine-3-carboxamide | 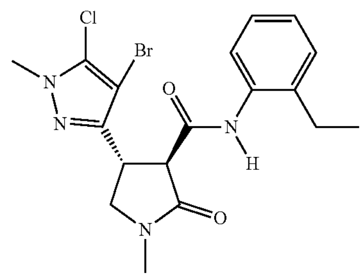 [SMILES: CCc1ccccc1NC(=O)[C@H]1C(=O)N(C)C[C@@H]1c1nn(C)c(Cl)c1Br] |
| 2.96 | (3S,4R)-4-(4-bromo-5-chloro-1-methyl-pyrazol-3-yl)-N-[2-(1,1-difluoroethyl)-3-fluoro-phenyl]-1-methyl-2-oxo-pyrrolidine-3-carboxamide | 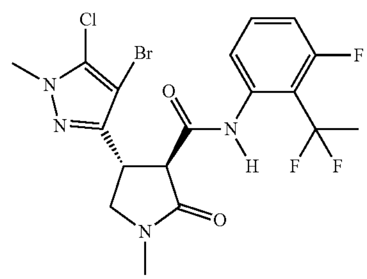 [SMILES: CN1C[C@H](c2nn(C)c(Cl)c2Br)[C@@H](C(=O)Nc2cccc(F)c2C(C)(F)F)C1=O] |
| 2.97 | (3S,4R)-4-(4-bromo-5-chloro-1-methyl-pyrazol-3-yl)-N-(2-chloro-3-thienyl)-1-methyl-2-oxo-pyrrolidine-3-carboxamide | 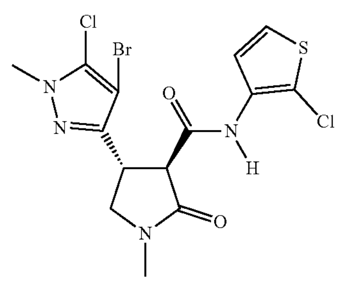 [SMILES: CN1C[C@H](c2nn(C)c(Cl)c2Br)[C@@H](C(=O)Nc2ccsc2Cl)C1=O] |
| 2.98 | (3S,4R)-4-(4-bromo-5-chloro-1-methyl-pyrazol-3-yl)-N-(2-fluoro-3-thienyl)-1-methyl-2-oxo-pyrrolidine-3-carboxamide | 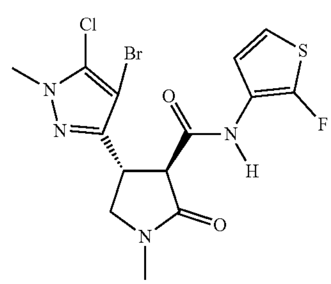 [SMILES: CN1C[C@H](c2nn(C)c(Cl)c2Br)[C@@H](C(=O)Nc2ccsc2F)C1=O] |
| 2.99 | (3S,4S)-4-(3-bromo-5-chloro-1-methyl-pyrazol-4-yl)-N-(2,3-difluorophenyl)-1-methyl-2-oxo-pyrrolidine-3-carboxamide | 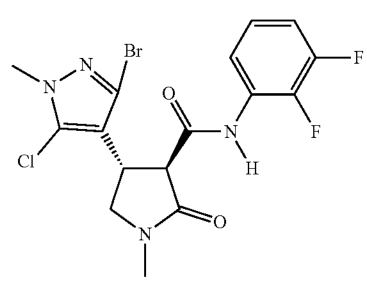 [SMILES: CN1C[C@H](c2c(Br)nn(C)c2Cl)[C@@H](C(=O)Nc2cccc(F)c2F)C1=O] |

TABLE 1-continued

Compounds of formula (II) for use in compositions described herein.

| Compound No. | Name | Structure |
|---|---|---|
| 2.100 | (3S,4S)-4-(3-bromo-5-chloro-1-methyl-pyrazol-4-yl)-N-(2-fluorophenyl)-1-methyl-2-oxo-pyrrolidine-3-carboxamide | 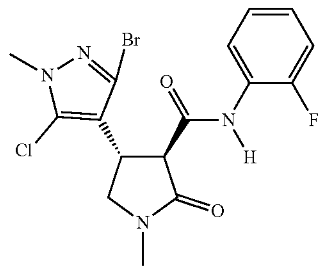 [SMILES: CN1C[C@H](c2c(Br)nn(C)c2Cl)[C@@H](C(=O)Nc2ccccc2F)C1=O] |
| 2.101 | (3S,4S)-4-(3-bromo-5-chloro-1-methyl-pyrazol-4-yl)-N-(2,4-difluorophenyl)-1-methyl-2-oxo-pyrrolidine-3-carboxamide | 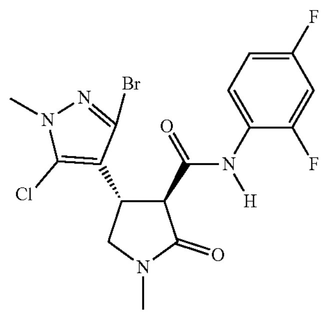 [SMILES: CN1C[C@H](c2c(Br)nn(C)c2Cl)[C@@H](C(=O)Nc2ccc(F)cc2F)C1=O] |
| 2.102 | (3S,4S)-4-(3-bromo-5-chloro-1-methyl-pyrazol-4-yl)-N-[3-fluoro-2-(trifluoromethoxy)phenyl]-1-methyl-2-oxo-pyrrolidine-3-carboxamide | 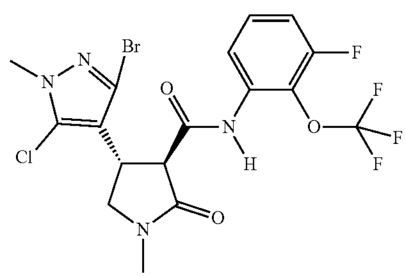 [SMILES: CN1C[C@H](c2c(Br)nn(C)c2Cl)[C@@H](C(=O)Nc2cccc(F)c2OC(F)(F)F)C1=O] |
| 2.103 | (3S,4S)-4-(3-bromo-5-chloro-1-methyl-pyrazol-4-yl)-N-[3-fluoro-2-(trifluoromethyl)phenyl]-1-methyl-2-oxo-pyrrolidine-3-carboxamide | 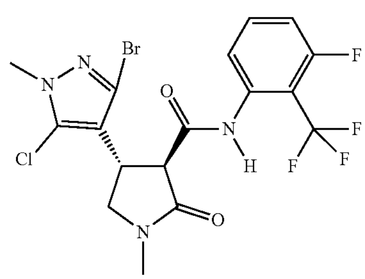 [SMILES: CN1C[C@H](c2c(Br)nn(C)c2Cl)[C@@H](C(=O)Nc2cccc(F)c2C(F)(F)F)C1=O] |
| 2.104 | (3S,4S)-4-(3-bromo-5-chloro-1-methyl-pyrazol-4-yl)-N-(3-fluoro-2-methoxy-phenyl)-1-methyl-2-oxo-pyrrolidine-3-carboxamide | 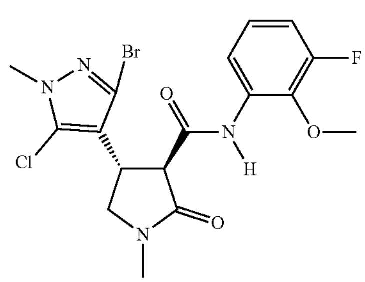 |

TABLE 1-continued

Compounds of formula (II) for use in compositions described herein.

| Compound No. | Name | Structure |
|---|---|---|
| 2.105 | (3S,4S)-4-(3-bromo-5-chloro-1-methyl-pyrazol-4-yl)-1-methyl-2-oxo-N-(2,3,4-trifluorophenyl)pyrrolidine-3-carboxamide | 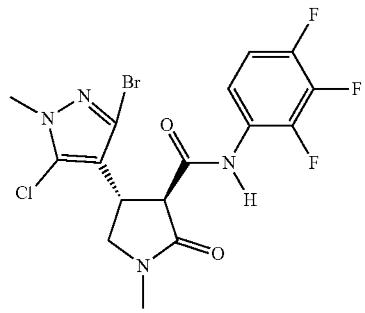 [SMILES: CN1C[C@H](c2c(Br)nn(C)c2Cl)[C@@H](C(=O)Nc2ccc(F)c(F)c2F)C1=O] |
| 2.106 | (3S,4S)-4-(3-bromo-5-chloro-1-methyl-pyrazol-4-yl)-N-(2,6-difluoro-3-pyridyl)-1-methyl-2-oxo-pyrrolidine-3-carboxamide | 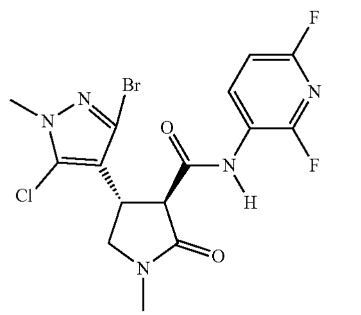 [SMILES: CN1C[C@H](c2c(Br)nn(C)c2Cl)[C@@H](C(=O)Nc2ccc(F)nc2F)C1=O] |
| 2.107 | (3S,4S)-4-(3-bromo-5-chloro-1-methyl-pyrazol-4-yl)-N-(6-fluoro-2-pyridyl)-1-methyl-2-oxo-pyrrolidine-3-carboxamide | 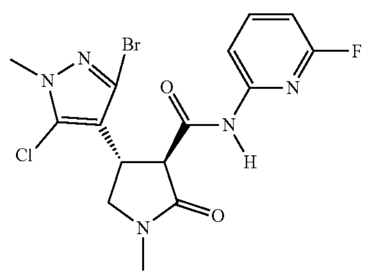 [SMILES: CN1C[C@H](c2c(Br)nn(C)c2Cl)[C@@H](C(=O)Nc2cccc(F)n2)C1=O] |
| 2.108 | (3S,4S)-4-(3-bromo-5-chloro-1-methyl-pyrazol-4-yl)-N-[2-(difluoromethoxy)-3-fluoro-phenyl]-1-methyl-2-oxo-pyrrolidine-3-carboxamide | 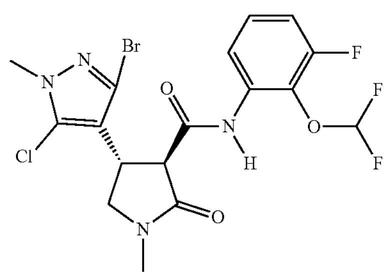 [SMILES: CN1C[C@H](c2c(Br)nn(C)c2Cl)[C@@H](C(=O)Nc2cccc(F)c2OC(F)F)C1=O] |
| 2.109 | (3S,4S)-4-(3-bromo-5-chloro-1-methyl-pyrazol-4-yl)-N-(2-ethylphenyl)-1-methyl-2-oxo-pyrrolidine-3-carboxamide | 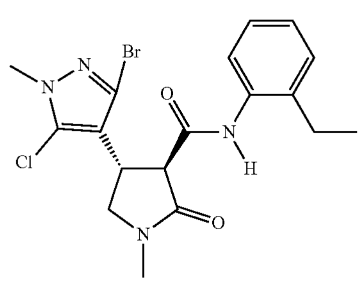 [SMILES: CCc1ccccc1NC(=O)[C@H]1C(=O)N(C)C[C@@H]1c1c(Br)nn(C)c1Cl] |

TABLE 1-continued

Compounds of formula (II) for use in compositions described herein.

| Compound No. | Name | Structure |
|---|---|---|
| 2.110 | (3S,4S)-4-(3-bromo-5-chloro-1-methyl-pyrazol-4-yl)-N-[2-(1,1-difluoroethyl)-3-fluoro-phenyl]-1-methyl-2-oxo-pyrrolidine-3-carboxamide | 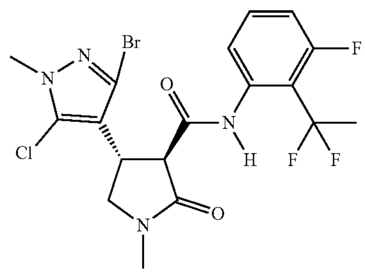 [SMILES: CN1C[C@H](c2c(Br)nn(C)c2Cl)[C@@H](C(=O)Nc2cccc(F)c2C(C)(F)F)C1=O] |
| 2.111 | (3S,4S)-4-(3-bromo-5-chloro-1-methyl-pyrazol-4-yl)-N-(2-chloro-3-thienyl)-1-methyl-2-oxo-pyrrolidine-3-carboxamide | 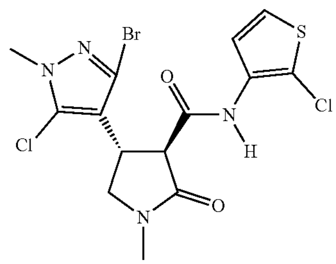 [SMILES: CN1C[C@H](c2c(Br)nn(C)c2Cl)[C@@H](C(=O)Nc2ccsc2Cl)C1=O] |
| 2.112 | (3S,4S)-4-(3-bromo-5-chloro-1-methyl-pyrazol-4-yl)-N-(2-fluoro-3-thienyl)-1-methyl-2-oxo-pyrrolidine-3-carboxamide | 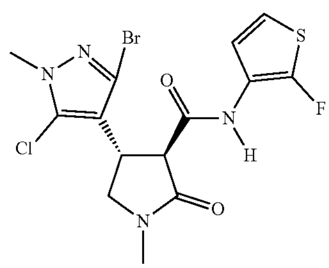 [SMILES: CN1C[C@H](c2c(Br)nn(C)c2Cl)[C@@H](C(=O)Nc2ccsc2F)C1=O] |
| 2.113 | (3S,4R)-4-(4-bromo-5-chloro-2-methyl-pyrazol-3-yl)-N-(2,3-difluorophenyl)-1-methyl-2-oxo-pyrrolidine-3-carboxamide | 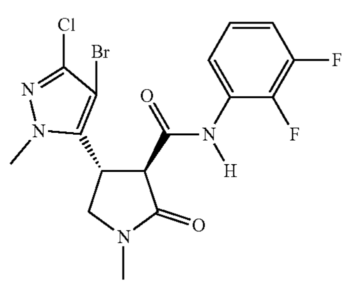 [SMILES: CN1C[C@H](c2c(Br)c(Cl)nn2C)[C@@H](C(=O)Nc2cccc(F)c2F)C1=O] |
| 2.114 | (3S)-4-(4-bromo-5-chloro-2-methyl-pyrazol-3-yl)-N-(2-fluorophenyl)-1-methyl-2-oxo-pyrrolidine-3-carboxamide | 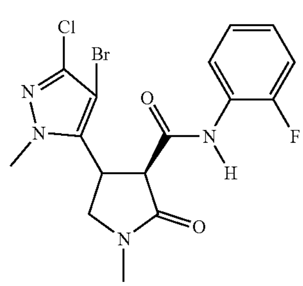 [SMILES: CN1CC(c2c(Br)c(Cl)nn2C)[C@@H](C(=O)Nc2ccccc2F)C1=O] |

TABLE 1-continued

Compounds of formula (II) for use in compositions described herein.

| Compound No. | Name | Structure |
|---|---|---|
| 2.115 | (3S,4R)-4-(4-bromo-5-chloro-2-methyl-pyrazol-3-yl)-N-(2,4-difluorophenyl)-1-methyl-2-oxo-pyrrolidine-3-carboxamide | 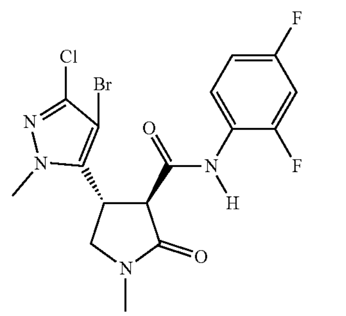 [SMILES: CN1C[C@H](c2c(Br)c(Cl)nn2C)[C@@H](C(=O)Nc2ccc(F)cc2F)C1=O] |
| 2.116 | (3S,4R)-4-(4-bromo-5-chloro-2-methyl-pyrazol-3-yl)-N-[3-fluoro-2-(trifluoromethoxy)phenyl]-1-methyl-2-oxo-pyrrolidine-3-carboxamide | 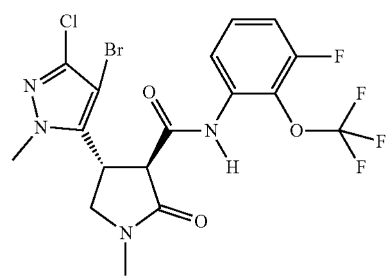 [SMILES: CN1C[C@H](c2c(Br)c(Cl)nn2C)[C@@H](C(=O)Nc2cccc(F)c2OC(F)(F)F)C1=O] |
| 2.117 | (3S,4R)-4-(4-bromo-5-chloro-2-methyl-pyrazol-3-yl)-N-[3-fluoro-2-(trifluoromethyl)phenyl]-1-methyl-2-oxo-pyrrolidine-3-carboxamide | 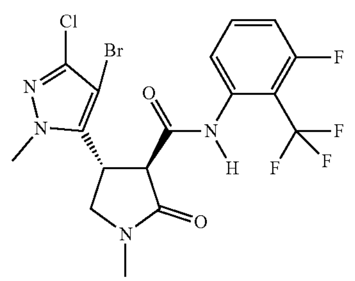 [SMILES: CN1C[C@H](c2c(Br)c(Cl)nn2C)[C@@H](C(=O)Nc2cccc(F)c2C(F)(F)F)C1=O] |
| 2.118 | (3S,4R)-4-(4-bromo-5-chloro-2-methyl-pyrazol-3-yl)-N-(3-fluoro-2-methoxy-phenyl)-1-methyl-2-oxo-pyrrolidine-3-carboxamide | 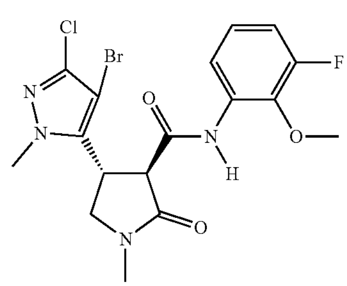 |
| 2.119 | (3S,4R)-4-(4-bromo-5-chloro-2-methyl-pyrazol-3-yl)-1-methyl-2-oxo-N-(2,3,4-trifluorophenyl)pyrrolidine-3-carboxamide | 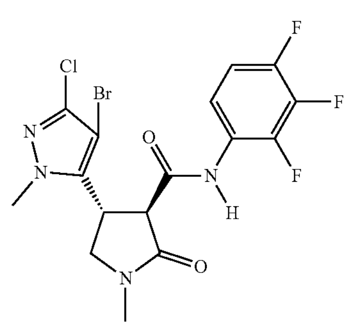 [SMILES: CN1C[C@H](c2c(Br)c(Cl)nn2C)[C@@H](C(=O)Nc2ccc(F)c(F)c2F)C1=O] |

TABLE 1-continued

Compounds of formula (II) for use in compositions described herein.

| Compound No. | Name | Structure |
|---|---|---|
| 2.120 | (3S,4R)-4-(4-bromo-3-chloro-1-methyl-3H-pyrazol-5-yl)-N-(2,6-difluoro-3-pyridyl)-1-methyl-2-oxo-pyrrolidine-3-carboxamide | 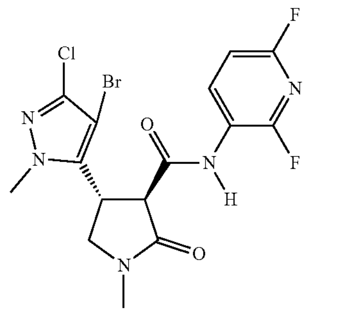 [SMILES: CN1C[C@H](c2c(Br)c(Cl)nn2C)[C@@H](C(=O)Nc2ccc(F)nc2F)C1=O] |
| 2.121 | (3S,4R)-4-(4-bromo-3-chloro-1-methyl-3H-pyrazol-5-yl)-N-(6-fluoro-2-pyridyl)-1-methyl-2-oxo-pyrrolidine-3-carboxamide | 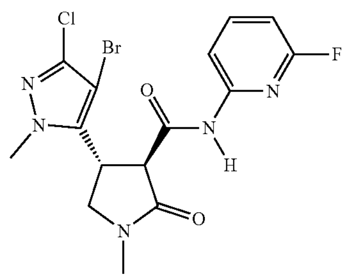 [SMILES: CN1C[C@H](c2c(Br)c(Cl)nn2C)[C@@H](C(=O)Nc2cccc(F)n2)C1=O] |
| 2.122 | (3S,4R)-4-(4-bromo-3-chloro-1-methyl-3H-pyrazol-5-yl)-N-[2-(difluoromethoxy)-3-fluoro-phenyl]-1-methyl-2-oxo-pyrrolidine-3-carboxamide | 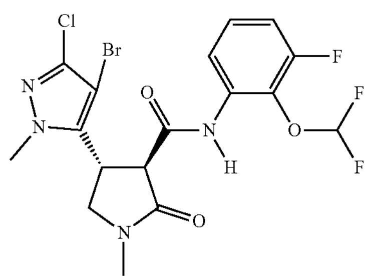 [SMILES: CN1C[C@H](c2c(Br)c(Cl)nn2C)[C@@H](C(=O)Nc2cccc(F)c2OC(F)F)C1=O] |
| 2.123 | (3S,4R)-4-(4-bromo-3-chloro-1-methyl-3H-pyrazol-5-yl)-N-(2-ethylphenyl)-1-methyl-2-oxo-pyrrolidine-3-carboxamide | 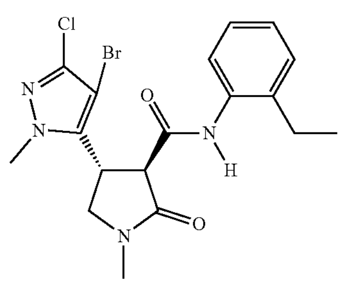 [SMILES: CCc1ccccc1NC(=O)[C@H]1C(=O)N(C)C[C@@H]1c1c(Br)c(Cl)nn1C] |
| 2.124 | (3S,4R)-4-(4-bromo-3-chloro-1-methyl-3H-pyrazol-5-yl)-N-[2-(1,1-difluoroethyl)-3-fluoro-phenyl]-1-methyl-2-oxo-pyrrolidine-3-carboxamide | 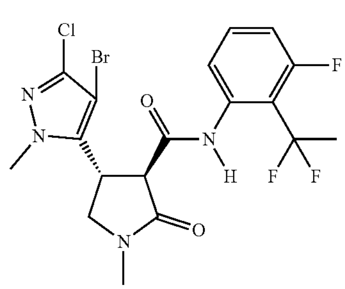 [SMILES: CN1C[C@H](c2c(Br)c(Cl)nn2C)[C@@H](C(=O)Nc2cccc(F)c2C(C)(F)F)C1=O] |

TABLE 1-continued

Compounds of formula (II) for use in compositions described herein.

| Compound No. | Name | Structure |
|---|---|---|
| 2.125 | (3S,4R)-4-(4-bromo-3-chloro-1-methyl-3H-pyrazol-5-yl)-N-(2-chloro-3-thienyl)-1-methyl-2-oxo-pyrrolidine-3-carboxamide | 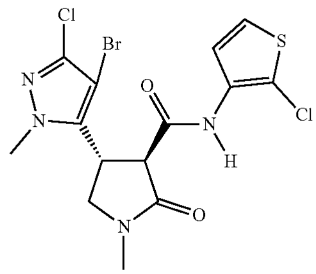 [SMILES: CN1C[C@H](c2c(Br)c(Cl)nn2C)[C@@H](C(=O)Nc2ccsc2Cl)C1=O] |
| 2.126I | (3S,4R)-4-(4-bromo-3-chloro-1-methyl-3H-pyrazol-5-yl)-N-(2-fluoro-3-thienyl)-1-methyl-2-oxo-pyrrolidine-3-carboxamide | 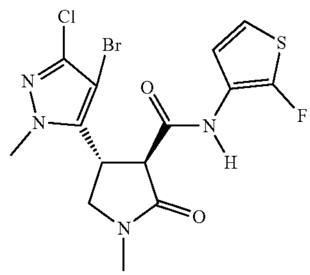 [SMILES: CN1C[C@H](c2c(Br)c(Cl)nn2C)[C@@H](C(=O)Nc2ccsc2F)C1=O] |

In one embodiment B is compound 2.1.
In one embodiment B is compound 2.2.
In one embodiment B is compound 2.3.
In one embodiment B is compound 2.4.
In one embodiment B is compound 2.5.
In one embodiment B is compound 2.6.
In one embodiment B is compound 2.7.
In one embodiment B is compound 2.8.
In one embodiment B is compound 2.9.
In one embodiment B is compound 2.10.
In one embodiment B is compound 2.11.
In one embodiment B is compound 2.12.
In one embodiment B is compound 2.13.
In one embodiment B is compound 2.14.
In one embodiment B is compound 2.15.
In one embodiment B is compound 2.16.
In one embodiment B is compound 2.17.
In one embodiment B is compound 2.18.
In one embodiment B is compound 2.19.
In one embodiment B is compound 2.20.
In one embodiment B is compound 2.21.
In one embodiment B is compound 2.22.
In one embodiment B is compound 2.23.
In one embodiment B is compound 2.24.
In one embodiment B is compound 2.25.
In one embodiment B is compound 2.26.
In one embodiment B is compound 2.27.
In one embodiment B is compound 2.28.
In one embodiment B is compound 2.29.
In one embodiment B is compound 2.30.
In one embodiment B is compound 2.31.
In one embodiment B is compound 2.32.
In one embodiment B is compound 2.33.
In one embodiment B is compound 2.34.
In one embodiment B is compound 2.35.
In one embodiment B is compound 2.36
In one embodiment B is compound 2.37
In one embodiment B is compound 2.38
In one embodiment B is compound 2.39.
In one embodiment B is compound 2.40.
In one embodiment B is compound 2.41.
In one embodiment B is compound 2.42.
In one embodiment B is compound 2.43.
In one embodiment B is compound 2.44
In one embodiment B is compound 2.45.
In one embodiment B is compound 2.46.
In one embodiment B is compound 2.47.
In one embodiment B is compound 2.48.
In one embodiment B is compound 2.49.
In one embodiment B is compound 2.50.
In one embodiment B is compound 2.51.
In one embodiment B is compound 2.52.
In one embodiment B is compound 2.53.
In one embodiment B is compound 2.54.
In one embodiment B is compound 2.55.
In one embodiment B is compound 2.56.
In one embodiment B is compound 2.57.
In one embodiment B is compound 2.58.
In one embodiment B is compound 2.59.
In one embodiment B is compound 2.60.
In one embodiment B is compound 2.61.
In one embodiment B is compound 2.62.
In one embodiment B is compound 2.63.
In one embodiment B is compound 2.64.
In one embodiment B is compound 2.65.
In one embodiment B is compound 2.66.
In one embodiment B is compound 2.67.
In one embodiment B is compound 2.68.
In one embodiment B is compound 2.69.
In one embodiment B is compound 2.70.
In one embodiment B is compound 2.71.
In one embodiment B is compound 2.72.
In one embodiment B is compound 2.73.
In one embodiment B is compound 2.74

In one embodiment B is compound 2.75.
In one embodiment B is compound 2.76.
In one embodiment B is compound 2.77.
In one embodiment B is compound 2.78.
In one embodiment B is compound 2.79.
In one embodiment B is compound 2.80.
In one embodiment B is compound 2.81.
In one embodiment B is compound 2.82.
In one embodiment B is compound 2.83
In one embodiment B is compound 2.84.
In one embodiment B is compound 2.85.
In one embodiment B is compound 2.86.
In one embodiment B is compound 2.87.
In one embodiment B is compound 2.88.
In one embodiment B is compound 2.89.
In one embodiment B is compound 2.90.
In one embodiment B is compound 2.91
In one embodiment B is compound 2.92.
In one embodiment B is compound 2.93
In one embodiment B is compound 2.94
In one embodiment B is compound 2.95.
In one embodiment B is compound 2.96.
In one embodiment B is compound 2.97.
In one embodiment B is compound 2.98.
In one embodiment B is compound 2.99
In one embodiment B is compound 2.100.
In one embodiment B is compound 2.101.
In one embodiment B is compound 2.102.
In one embodiment B is compound 2.103.
In one embodiment B is compound 2.104.
In one embodiment B is compound 2.105.
In one embodiment B is compound 2.106.
In one embodiment B is compound 2.107.
In one embodiment B is compound 2.108.
In one embodiment B is compound 2.109.
In one embodiment B is compound 2.110.
In one embodiment B is compound 2.111.
In one embodiment B is compound 2.112.
In one embodiment B is compound 2.113.
In one embodiment B is compound 2.114.
In one embodiment B is compound 2.115.
In one embodiment B is compound 2.116.
In one embodiment B is compound 2.117.
In one embodiment B is compound 2.118.
In one embodiment B is compound 2.119.
In one embodiment B is compound 2.120.
In one embodiment B is compound 2.121.
In one embodiment B is compound 2.122.
In one embodiment B is compound 2.123.
In one embodiment B is compound 2.124.
In one embodiment B is compound 2.125.
In one embodiment B is compound 2.126.

Compounds of formula (II) as described herein may be made as described in WO2015/084796 as well as by the racemic synthesis route and asymmetric synthesis route as described herein in the Preparation Examples.

The starting materials used for the preparation of the compounds employed in the invention may be purchased from usual commercial suppliers or may be prepared by known methods. The starting materials as well as the intermediates may be purified before use in the next WO 2015/193202step by state of the art methodologies such as chromatography, crystallization, distillation and filtration.

Crops of useful plants in which the composition according to the invention can be used include perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and Zoysia grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

Crops are to be understood as being those which are naturally occurring, obtained by conventional methods of breeding, or obtained by genetic engineering. They include crops which contain so-called output traits (e.g. improved storage stability, higher nutritional value and improved flavour).

Crops are to be understood as also including those crops which have been rendered tolerant to herbicides like bromoxynil or classes of herbicides such as ALS-, EPSPS-, GS-, HPPD- and PPO-inhibitors. An example of a crop that has been rendered tolerant to imidazolinones, e.g. imazamox, by conventional methods of breeding is Clearfield® summer canola. Examples of crops that have been rendered tolerant to herbicides by genetic engineering methods include e.g. glyphosate- and glufosinate-resistant maize varieties commercially available under the trade names RoundupReady®, Herculex I® and LibertyLink®.

Crops are also to be understood as being those which naturally are or have been rendered resistant to harmful insects. This includes plants transformed by the use of recombinant DNA techniques, for example, to be capable of synthesising one or more selectively acting toxins, such as are known, for example, from toxin-producing bacteria. Examples of toxins which can be expressed include δ-endotoxins, vegetative insecticidal proteins (Vip), insecticidal proteins of bacteria colonising nematodes, and toxins produced by scorpions, arachnids, wasps and fungi.

An example of a crop that has been modified to express the *Bacillus thuringiensis* toxin is the Bt maize KnockOut® (Syngenta Seeds). An example of a crop comprising more than one gene that codes for insecticidal resistance and thus expresses more than one toxin is VipCot® (Syngenta Seeds). Crops or seed material thereof can also be resistant to multiple types of pests (so-called stacked transgenic events when created by genetic modification). For example, a plant can have the ability to express an insecticidal protein while at the same time being herbicide tolerant, for example Herculex I® (Dow AgroSciences, Pioneer Hi-Bred International).

Compositions of the invention can typically be used to control a wide variety of monocotyledonous and dicotyledonous weed species. Examples of monocotyledonous species that can typically be controlled include *Alopecurus myosuroides, Avena fatua, Brachiaria plantaginea, Bromus tectorum, Cyperus esculentus, Digitaria sanguinalis, Echinochloa crus-galli, Lolium perenne, Lolium multiflorum, Panicum miliaceum, Poa annua, Setaria viridis, Setaria*

*faberi* and *Sorghum bicolor*. Examples of dicotyledonous species that can be controlled include *Abutilon theophrasti, Amaranthus retroflexus, Bidens pilosa, Chenopodium album, Euphorbia heterophylla, Galium aparine, Ipomoea hederacea, Kochia scoparia, Polygonum convolvulus, Sida spinosa, Sinapis arvensis, Solanum nigrum, Stellaria media, Veronica persica* and *Xanthium strumarium*.

In all aspects of the invention, in any particular embodiment, the weeds, e.g. to be controlled and/or growth-inhibited, may be monocotyledonous or dicotyledonous weeds, which are tolerant or resistant to one or more other herbicides for example, HPPD inhibitor herbicides such as mesotrione, PSII inhibitor herbicides such as atrazine or EPSPS inhibitors such as glyphosate. Such weeds include, but are not limited to resistant *Amaranthus* biotypes.

Compositions of this invention can also be mixed with one or more further pesticides including herbicides [typically different to the herbicides of formula (I) and formula (II)], fungicides, insecticides, nematocides, bactericides, acaricides, growth regulators, chemosterilants, semiochemicals, repellents, attractants, pheromones, feeding stimulants or other biologically active compounds to form a multi-component pesticide giving an even broader spectrum of agricultural protection.

Similarly compositions of the invention (which includes those comprising one or more additional pesticide as described in the preceding paragraph) can further include one or more safeners. In particular, the following safeners are especially preferred: AD 67 (MON 4660), benoxacor, cloquintocet-mexyl, cyometrinil, cyprosulfamide, dichlormid, dicyclonon, dietholate, fenchlorazole-ethyl, fenclorim, flurazole, fluxofenim, furilazole, furilazome, isoxadifen-ethyl, mefenpyr-diethyl, mephenate, oxabetrinil, naphthalic anhydride (CAS RN 81-84-5), TI-35, N-isopropyl-4-(2-methoxy-benzoylsulfamoyl)-benzamide (CAS RN 221668-34-4) and N-(2-methoxybenzoyl)-4-[(methylaminocarbonyl)amino]benzenesulfonamide. Such safeners may also be used in the form of esters or salts, as mentioned e.g. in The Pesticide Manual, 15th Ed. (BCPC), 2009. Thus, the reference to cloquintocet-mexyl also applies to cloquintocet and to a lithium, sodium, potassium, calcium, magnesium, aluminium, iron, ammonium, quaternary ammonium, sulfonium or phosphonium salt thereof as disclosed in WO02/34048 and the reference to fenchlorazole-ethyl also applies to fenchlorazole, etc.

In general, the mixing ratio (by weight) of the compound of formula (I) to the compound of formula (II) is from 0.01:1 to 100:1, more preferably from 0.05:1 to 20:1, even more preferably from 0.1:1 to 20:1 and most preferably from 0.2:1 to 20:1, for example, 0.3125:1, 0.625:1, 1:1, 1.25:1, 2.5:1, 5:1, 10:1 and 20:1.

The amount of a composition according to the invention to be applied, will depend on various factors, such as the compounds employed; the subject of the treatment, such as, for example the plants (crops and/or weeds), soil or seeds; the part of the plant to which the treatment is applied (e.g. foliar application, drench, in-furrow application) the type of treatment, such as, for example spraying, dusting or seed dressing; the application timing (pre- or post-emergence).

When applied per se to the useful plants, or the locus thereof, component (A) may be applied at a rate of 50 to 2000 g a.i./ha, particularly 100 to 1000 g a.i./ha and more particularly 300 to 500 g a.i./ha e.g. 300, 350, 400, 450 or 500 g a.i./ha. However, in certain embodiments, component (A) is preferably applied lower rates of 5 to 25 g a.i./ha, in particular at 5, 10, 15, 20 or 25 g a.i./ha.

Component (B), i.e. a compound of formula (II), when used per se, is typically applied at a rate of from 5 to 2000 g a.i./ha. In particular, it may be applied at a rate of 10, 25, 30, 60, 75, 100, 125, 200, 250, 300, 350, 400, 450, 500 or 1000 g a.i./ha.

In agricultural practice the application rates of the composition according to the invention depend on the type of effect desired, and typically range from 10 to 4000 g of total composition per hectare. Thus in particular compositions of the invention component (A) may be applied at a rate of 5, 10, 15, 20, 25, 50, 300, 350, 400, 450 or 500 g a.i./ha, typically in association with component B at a rate of 10, 25, 30, 60, 75, 100, 125, 200, 250, 300, 350, 400, 450, 500 or 1000 g a.i./ha.

The compounds of the invention can be applied before or after planting of the crops, before weeds emerge (pre-emergence application) or after weeds emerge (post-emergence application), and are particularly effective when applied pre-emergence to the weeds.

Where a safener is combined with mixtures of the invention, it is preferred that the mixing ratio of compound of formula (I) to safener is from 100:1 to 1:10, especially from 20:1 to 1:1.

It is possible that the safener and the compositions of the invention are applied simultaneously. For example, the safener and the composition of the invention might be applied to the locus pre-emergence or might be applied to the crop post-emergence. It is also possible that the safener and the composition of the invention are applied sequentially. For example, the safener might be applied before sowing the seeds as a seed treatment and the composition of the invention might be applied to the locus pre-emergence or might be applied to the crop post-emergence.

The compositions of the invention can advantageously be used in the below-mentioned formulations (in which case "active ingredient" relates to the respective mixture of compound of formula (I) with a compound of formula (II) or, when a safener is also used, the respective mixture of the compound of formula (I) with the compound of formula (II) and the safener).

The individual components of the composition of the invention may be utilised as the technical active ingredient as produced. More typically however, the compositions according to the invention may be formulated in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspo-emulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono and di-alkylphosphate esters; and also further substances described e.g. in McCutcheon's Detergents and Emulsifiers Annual, MC Publishing Corp., Ridgewood New Jersey (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The formulations according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, $10^{th}$ Edition, Southern Illinois University, 2010.

The formulations generally comprise from 0.1 to 99% by weight, especially from 0.1 to 95% by weight, of compounds (A) and (B) and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %), wherein the term "active ingredient" refers to the total weight % of the combination of all active ingredients in the composition:

Emulsifiable Concentrates:
  active ingredient: 1 to 95%, preferably 60 to 90%
  surface-active agent: 1 to 30%, preferably 5 to 20%
  liquid carrier: 1 to 80%, preferably 1 to 35%
Dusts:
  active ingredient: 0.1 to 10%, preferably 0.1 to 5%
  solid carrier: 99.9 to 90%, preferably 99.9 to 99%
Suspension Concentrates:
  active ingredient: 5 to 75%, preferably 10 to 50%
  water: 94 to 24%, preferably 88 to 30%
  surface-active agent: 1 to 40%, preferably 2 to 30%
Wettable Powders:
  active ingredient: 0.5 to 90%, preferably 1 to 80%
  surface-active agent: 0.5 to 20%, preferably 1 to 15%
  solid carrier: 5 to 95%, preferably 15 to 90%
Granules:
  active ingredient: 0.1 to 30%, preferably 0.1 to 15%
  solid carrier: 99.5 to 70%, preferably 97 to 85%

The following Examples further illustrate, but do not limit, the invention.

| Wettable powders | a) | b) | c) |
| --- | --- | --- | --- |
| active ingredients | 25% | 50% | 75% |
| sodium lignosulfonate | 5% | 5% | — |
| sodium lauryl sulphate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
| --- | --- | --- | --- |
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The combination is thoroughly mixed with the adjuvants and the mixture is thoroughly ground in a suitable mill, affording powders that can be used directly for seed treatment.

| Emulsifiable concentrate | |
| --- | --- |
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
| --- | --- | --- | --- |
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruded granules | |
| --- | --- |
| Active ingredients | 15% |
| sodium lignosulfonate | 2% |
| Carboxymethylcellulose | 1% |
| Kaolin | 82% |

The combination is mixed and ground with the adjuvants, and the mixture is moistened with water. The mixture is extruded and then dried in a stream of air.

| Coated granules | |
| --- | --- |
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

| Suspension concentrate | |
| --- | --- |
| active ingredients | 40% |
| propylene glycol | 10% |
| nonylphenol polyethylene glycol ether (15 mol of ethylene oxide) | 6% |
| Sodium lignosulfonate | 10% |
| Carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
| --- | --- |
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension

28 Parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

In one set of embodiments, the composition of the invention will comprise A and B as described in Table 2 below. Particularly preferred compositions of the invention are those from Table 2, comprising a compound of formula (II) as described herein in the Examples.

TABLE 2

Compositions of the Invention

| Composition Number | A Cmpd of formula (I) | B Cmpd of formula (II) | Typical Weight Ratio | Preferred Weight Ratio | More Preferred Weight Ratio |
|---|---|---|---|---|---|
| 1 | 1.1 | 2.1 | 0.01:1 to 100:1 | 0.05:1 to 20:1 | 0.1:1 to 20:1 |
| 2 | 1.1 | 2.2 | 0.01:1 to 100:1 | 0.05:1 to 20:1 | 0.1:1 to 20:1 |
| 3 | 1.1 | 2.3 | 0.01:1 to 100:1 | 0.05:1 to 20:1 | 0.1:1 to 20:1 |
| 4 | 1.1 | 2.4 | 0.01:1 to 100:1 | 0.05:1 to 20:1 | 0.1:1 to 20:1 |
| 5 | 1.1 | 2.5 | 0.01:1 to 100:1 | 0.05:1 to 20:1 | 0.1:1 to 20:1 |
| 6 | 1.1 | 2.6 | 0.01:1 to 100:1 | 0.05:1 to 20:1 | 0.1:1 to 20:1 |
| 7 | 1.1 | 2.7 | 0.01:1 to 100:1 | 0.05:1 to 20:1 | 0.1:1 to 20:1 |
| 8 | 1.1 | 2.8 | 0.01:1 to 100:1 | 0.05:1 to 20:1 | 0.1:1 to 20:1 |
| 9 | 1.1 | 2.9 | 0.01:1 to 100:1 | 0.05:1 to 20:1 | 0.1:1 to 20:1 |
| 10 | 1.1 | 2.10 | 0.01:1 to 100:1 | 0.05:1 to 20:1 | 0.1:1 to 20:1 |
| 11 | 1.1 | 2.11 | 0.01:1 to 100:1 | 0.05:1 to 20:1 | 0.1:1 to 20:1 |
| 12 | 1.1 | 2.12 | 0.01:1 to 100:1 | 0.05:1 to 20:1 | 0.1:1 to 20:1 |
| 13 | 1.1 | 2.13 | 0.01:1 to 100:1 | 0.05:1 to 20:1 | 0.1:1 to 20:1 |
| 14 | 1.1 | 2.14 | 0.01:1 to 100:1 | 0.05:1 to 20:1 | 0.1:1 to 20:1 |
| 15 | 1.1 | 2.15 | 0.01:1 to 100:1 | 0.05:1 to 20:1 | 0.1:1 to 20:1 |
| 16 | 1.1 | 2.16 | 0.01:1 to 100:1 | 0.05:1 to 20:1 | 0.1:1 to 20:1 |
| 17 | 1.1 | 2.17 | 0.01:1 to 100:1 | 0.05:1 to 20:1 | 0.1:1 to 20:1 |
| 18 | 1.1 | 2.18 | 0.01:1 to 100:1 | 0.05:1 to 20:1 | 0.1:1 to 20:1 |
| 19 | 1.1 | 2.19 | 0.01:1 to 100:1 | 0.05:1 to 20:1 | 0.1:1 to 20:1 |
| 20 | 1.1 | 2.20 | 0.01:1 to 100:1 | 0.05:1 to 20:1 | 0.1:1 to 20:1 |
| 21 | 1.1 | 2.21 | 0.01:1 to 100:1 | 0.05:1 to 20:1 | 0.1:1 to 20:1 |
| 22 | 1.1 | 2.22 | 0.01:1 to 100:1 | 0.05:1 to 20:1 | 0.1:1 to 20:1 |
| 23 | 1.1 | 2.23 | 0.01:1 to 100:1 | 0.05:1 to 20:1 | 0.1:1 to 20:1 |
| 24 | 1.1 | 2.24 | 0.01:1 to 100:1 | 0.05:1 to 20:1 | 0.1:1 to 20:1 |
| 25 | 1.1 | 2.25 | 0.01:1 to 100:1 | 0.05:1 to 20:1 | 0.1:1 to 20:1 |
| 26 | 1.1 | 2.26 | 0.01:1 to 100:1 | 0.05:1 to 20:1 | 0.1:1 to 20:1 |
| 27 | 1.1 | 2.27 | 0.01:1 to 100:1 | 0.05:1 to 20:1 | 0.1:1 to 20:1 |
| 28 | 1.1 | 2.28 | 0.01:1 to 100:1 | 0.05:1 to 20:1 | 0.1:1 to 20:1 |
| 29 | 1.1 | 2.29 | 0.01:1 to 100:1 | 0.05:1 to 20:1 | 0.1:1 to 20:1 |
| 30 | 1.1 | 2.30 | 0.01:1 to 100:1 | 0.05:1 to 20:1 | 0.1:1 to 20:1 |
| 31 | 1.1 | 2.31 | 0.01:1 to 100:1 | 0.05:1 to 20:1 | 0.1:1 to 20:1 |
| 32 | 1.1 | 2.32 | 0.01:1 to 100:1 | 0.05:1 to 20:1 | 0.1:1 to 20:1 |
| 33 | 1.1 | 2.33 | 0.01:1 to 100:1 | 0.05:1 to 20:1 | 0.1:1 to 20:1 |
| 34 | 1.1 | 2.34 | 0.01:1 to 100:1 | 0.05:1 to 20:1 | 0.1:1 to 20:1 |
| 35 | 1.1 | 2.35 | 0.01:1 to 100:1 | 0.05:1 to 20:1 | 0.1:1 to 20:1 |
| 36 | 1.1 | 2.36 | 0.01:1 to 100:1 | 0.05:1 to 20:1 | 0.1:1 to 20:1 |
| 37 | 1.1 | 2.37 | 0.01:1 to 100:1 | 0.05:1 to 20:1 | 0.1:1 to 20:1 |
| 38 | 1.1 | 2.38 | 0.01:1 to 100:1 | 0.05:1 to 20:1 | 0.1:1 to 20:1 |
| 39 | 1.1 | 2.39 | 0.01:1 to 100:1 | 0.05:1 to 20:1 | 0.1:1 to 20:1 |
| 40 | 1.1 | 2.40 | 0.01:1 to 100:1 | 0.05:1 to 20:1 | 0.1:1 to 20:1 |
| 41 | 1.1 | 2.41 | 0.01:1 to 100:1 | 0.05:1 to 20:1 | 0.1:1 to 20:1 |
| 42 | 1.1 | 2.42 | 0.01:1 to 100:1 | 0.05:1 to 20:1 | 0.1:1 to 20:1 |
| 43 | 1.1 | 2.43 | 0.01:1 to 100:1 | 0.05:1 to 20:1 | 0.1:1 to 20:1 |
| 44 | 1.1 | 2.44 | 0.01:1 to 100:1 | 0.05:1 to 20:1 | 0.1:1 to 20:1 |
| 45 | 1.1 | 2.45 | 0.01:1 to 100:1 | 0.05:1 to 20:1 | 0.1:1 to 20:1 |
| 46 | 1.1 | 2.46 | 0.01:1 to 100:1 | 0.05:1 to 20:1 | 0.1:1 to 20:1 |
| 47 | 1.1 | 2.47 | 0.01:1 to 100:1 | 0.05:1 to 20:1 | 0.1:1 to 20:1 |
| 48 | 1.1 | 2.48 | 0.01:1 to 100:1 | 0.05:1 to 20:1 | 0.1:1 to 20:1 |
| 49 | 1.1 | 2.49 | 0.01:1 to 100:1 | 0.05:1 to 20:1 | 0.1:1 to 20:1 |
| 50 | 1.1 | 2.50 | 0.01:1 to 100:1 | 0.05:1 to 20:1 | 0.1:1 to 20:1 |
| 51 | 1.1 | 2.51 | 0.01:1 to 100:1 | 0.05:1 to 20:1 | 0.1:1 to 20:1 |
| 52 | 1.1 | 2.52 | 0.01:1 to 100:1 | 0.05:1 to 20:1 | 0.1:1 to 20:1 |
| 53 | 1.1 | 2.53 | 0.01:1 to 100:1 | 0.05:1 to 20:1 | 0.1:1 to 20:1 |
| 54 | 1.1 | 2.54 | 0.01:1 to 100:1 | 0.05:1 to 20:1 | 0.1:1 to 20:1 |
| 55 | 1.1 | 2.55 | 0.01:1 to 100:1 | 0.05:1 to 20:1 | 0.1:1 to 20:1 |
| 56 | 1.1 | 2.56 | 0.01:1 to 100:1 | 0.05:1 to 20:1 | 0.1:1 to 20:1 |
| 57 | 1.1 | 2.57 | 0.01:1 to 100:1 | 0.05:1 to 20:1 | 0.1:1 to 20:1 |
| 58 | 1.1 | 2.58 | 0.01:1 to 100:1 | 0.05:1 to 20:1 | 0.1:1 to 20:1 |
| 59 | 1.1 | 2.59 | 0.01:1 to 100:1 | 0.05:1 to 20:1 | 0.1:1 to 20:1 |
| 60 | 1.1 | 2.60 | 0.01:1 to 100:1 | 0.05:1 to 20:1 | 0.1:1 to 20:1 |
| 61 | 1.1 | 2.61 | 0.01:1 to 100:1 | 0.05:1 to 20:1 | 0.1:1 to 20:1 |
| 62 | 1.1 | 2.62 | 0.01:1 to 100:1 | 0.05:1 to 20:1 | 0.1:1 to 20:1 |
| 63 | 1.1 | 2.63 | 0.01:1 to 100:1 | 0.05:1 to 20:1 | 0.1:1 to 20:1 |
| 64 | 1.1 | 2.64 | 0.01:1 to 100:1 | 0.05:1 to 20:1 | 0.1:1 to 20:1 |
| 65 | 1.1 | 2.65 | 0.01:1 to 100:1 | 0.05:1 to 20:1 | 0.1:1 to 20:1 |
| 66 | 1.1 | 2.66 | 0.01:1 to 100:1 | 0.05:1 to 20:1 | 0.1:1 to 20:1 |
| 67 | 1.1 | 2.67 | 0.01:1 to 100:1 | 0.05:1 to 20:1 | 0.1:1 to 20:1 |
| 68 | 1.1 | 2.68 | 0.01:1 to 100:1 | 0.05:1 to 20:1 | 0.1:1 to 20:1 |
| 69 | 1.1 | 2.69 | 0.01:1 to 100:1 | 0.05:1 to 20:1 | 0.1:1 to 20:1 |
| 70 | 1.1 | 2.70 | 0.01:1 to 100:1 | 0.05:1 to 20:1 | 0.1:1 to 20:1 |
| 71 | 1.1 | 2.71 | 0.01:1 to 100:1 | 0.05:1 to 20:1 | 0.1:1 to 20:1 |
| 72 | 1.1 | 2.72 | 0.01:1 to 100:1 | 0.05:1 to 20:1 | 0.1:1 to 20:1 |
| 73 | 1.1 | 2.73 | 0.01:1 to 100:1 | 0.05:1 to 20:1 | 0.1:1 to 20:1 |
| 74 | 1.1 | 2.74 | 0.01:1 to 100:1 | 0.05:1 to 20:1 | 0.1:1 to 20:1 |
| 75 | 1.1 | 2.75 | 0.01:1 to 100:1 | 0.05:1 to 20:1 | 0.1:1 to 20:1 |
| 76 | 1.1 | 2.76 | 0.01:1 to 100:1 | 0.05:1 to 20:1 | 0.1:1 to 20:1 |
| 77 | 1.1 | 2.77 | 0.01:1 to 100:1 | 0.05:1 to 20:1 | 0.1:1 to 20:1 |
| 78 | 1.1 | 2.78 | 0.01:1 to 100:1 | 0.05:1 to 20:1 | 0.1:1 to 20:1 |
| 79 | 1.1 | 2.79 | 0.01:1 to 100:1 | 0.05:1 to 20:1 | 0.1:1 to 20:1 |
| 80 | 1.1 | 2.80 | 0.01:1 to 100:1 | 0.05:1 to 20:1 | 0.1:1 to 20:1 |
| 81 | 1.1 | 2.81 | 0.01:1 to 100:1 | 0.05:1 to 20:1 | 0.1:1 to 20:1 |
| 82 | 1.1 | 2.82 | 0.01:1 to 100:1 | 0.05:1 to 20:1 | 0.1:1 to 20:1 |
| 83 | 1.1 | 2.83 | 0.01:1 to 100:1 | 0.05:1 to 20:1 | 0.1:1 to 20:1 |
| 84 | 1.1 | 2.84 | 0.01:1 to 100:1 | 0.05:1 to 20:1 | 0.1:1 to 20:1 |
| 85 | 1.1 | 2.85 | 0.01:1 to 100:1 | 0.05:1 to 20:1 | 0.1:1 to 20:1 |
| 86 | 1.1 | 2.86 | 0.01:1 to 100:1 | 0.05:1 to 20:1 | 0.1:1 to 20:1 |
| 87 | 1.1 | 2.87 | 0.01:1 to 100:1 | 0.05:1 to 20:1 | 0.1:1 to 20:1 |
| 88 | 1.1 | 2.88 | 0.01:1 to 100:1 | 0.05:1 to 20:1 | 0.1:1 to 20:1 |
| 89 | 1.1 | 2.89 | 0.01:1 to 100:1 | 0.05:1 to 20:1 | 0.1:1 to 20:1 |
| 90 | 1.1 | 2.90 | 0.01:1 to 100:1 | 0.05:1 to 20:1 | 0.1:1 to 20:1 |
| 91 | 1.1 | 2.91 | 0.01:1 to 100:1 | 0.05:1 to 20:1 | 0.1:1 to 20:1 |
| 92 | 1.1 | 2.92 | 0.01:1 to 100:1 | 0.05:1 to 20:1 | 0.1:1 to 20:1 |
| 93 | 1.1 | 2.93 | 0.01:1 to 100:1 | 0.05:1 to 20:1 | 0.1:1 to 20:1 |
| 94 | 1.1 | 2.94 | 0.01:1 to 100:1 | 0.05:1 to 20:1 | 0.1:1 to 20:1 |
| 95 | 1.1 | 2.95 | 0.01:1 to 100:1 | 0.05:1 to 20:1 | 0.1:1 to 20:1 |
| 96 | 1.1 | 2.96 | 0.01:1 to 100:1 | 0.05:1 to 20:1 | 0.1:1 to 20:1 |
| 97 | 1.1 | 2.97 | 0.01:1 to 100:1 | 0.05:1 to 20:1 | 0.1:1 to 20:1 |
| 98 | 1.1 | 2.98 | 0.01:1 to 100:1 | 0.05:1 to 20:1 | 0.1:1 to 20:1 |
| 99 | 1.1 | 2.99 | 0.01:1 to 100:1 | 0.05:1 to 20:1 | 0.1:1 to 20:1 |
| 100 | 1.1 | 2.100 | 0.01:1 to 100:1 | 0.05:1 to 20:1 | 0.1:1 to 20:1 |
| 101 | 1.1 | 2.101 | 0.01:1 to 100:1 | 0.05:1 to 20:1 | 0.1:1 to 20:1 |
| 102 | 1.1 | 2.102 | 0.01:1 to 100:1 | 0.05:1 to 20:1 | 0.1:1 to 20:1 |
| 103 | 1.1 | 2.103 | 0.01:1 to 100:1 | 0.05:1 to 20:1 | 0.1:1 to 20:1 |
| 104 | 1.1 | 2.104 | 0.01:1 to 100:1 | 0.05:1 to 20:1 | 0.1:1 to 20:1 |
| 105 | 1.1 | 2.105 | 0.01:1 to 100:1 | 0.05:1 to 20:1 | 0.1:1 to 20:1 |
| 106 | 1.1 | 2.106 | 0.01:1 to 100:1 | 0.05:1 to 20:1 | 0.1:1 to 20:1 |
| 107 | 1.1 | 2.107 | 0.01:1 to 100:1 | 0.05:1 to 20:1 | 0.1:1 to 20:1 |
| 108 | 1.1 | 2.108 | 0.01:1 to 100:1 | 0.05:1 to 20:1 | 0.1:1 to 20:1 |
| 109 | 1.1 | 2.109 | 0.01:1 to 100:1 | 0.05:1 to 20:1 | 0.1:1 to 20:1 |

TABLE 2-continued

Compositions of the Invention

| Composition Number | A Cmpd of formula (I) | B Cmpd of formula (II) | Typical Weight Ratio | Preferred Weight Ratio | More Preferred Weight Ratio |
|---|---|---|---|---|---|
| 110 | 1.1 | 2.110 | 0.01:1 to 100:1 | 0.05:1 to 20:1 | 0.1:1 to 20:1 |
| 111 | 1.1 | 2.111 | 0.01:1 to 100:1 | 0.05:1 to 20:1 | 0.1:1 to 20:1 |
| 112 | 1.1 | 2.112 | 0.01:1 to 100:1 | 0.05:1 to 20:1 | 0.1:1 to 20:1 |
| 113 | 1.1 | 2.113 | 0.01:1 to 100:1 | 0.05:1 to 20:1 | 0.1:1 to 20:1 |
| 114 | 1.1 | 2.114 | 0.01:1 to 100:1 | 0.05:1 to 20:1 | 0.1:1 to 20:1 |
| 115 | 1.1 | 2.115 | 0.01:1 to 100:1 | 0.05:1 to 20:1 | 0.1:1 to 20:1 |
| 116 | 1.1 | 2.116 | 0.01:1 to 100:1 | 0.05:1 to 20:1 | 0.1:1 to 20:1 |
| 117 | 1.1 | 2.117 | 0.01:1 to 100:1 | 0.05:1 to 20:1 | 0.1:1 to 20:1 |
| 118 | 1.1 | 2.118 | 0.01:1 to 100:1 | 0.05:1 to 20:1 | 0.1:1 to 20:1 |
| 119 | 1.1 | 2.119 | 0.01:1 to 100:1 | 0.05:1 to 20:1 | 0.1:1 to 20:1 |
| 120 | 1.1 | 2.120 | 0.01:1 to 100:1 | 0.05:1 to 20:1 | 0.1:1 to 20:1 |
| 121 | 1.1 | 2.121 | 0.01:1 to 100:1 | 0.05:1 to 20:1 | 0.1:1 to 20:1 |
| 122 | 1.1 | 2.122 | 0.01:1 to 100:1 | 0.05:1 to 20:1 | 0.1:1 to 20:1 |
| 123 | 1.1 | 2.123 | 0.01:1 to 100:1 | 0.05:1 to 20:1 | 0.1:1 to 20:1 |
| 124 | 1.1 | 2.124 | 0.01:1 to 100:1 | 0.05:1 to 20:1 | 0.1:1 to 20:1 |
| 125 | 1.1 | 2.125 | 0.01:1 to 100:1 | 0.05:1 to 20:1 | 0.1:1 to 20:1 |
| 126 | 1.1 | 2.126 | 0.01:1 to 100:1 | 0.05:1 to 20:1 | 0.1:1 to 20:1 |
| 127 | 1.2 | 2.1 | 0.01:1 to 100:1 | 0.05:1 to 20:1 | 0.1:1 to 20:1 |
| 128 | 1.2 | 2.2 | 0.01:1 to 100:1 | 0.05:1 to 20:1 | 0.1:1 to 20:1 |
| 129 | 1.2 | 2.3 | 0.01:1 to 100:1 | 0.05:1 to 20:1 | 0.1:1 to 20:1 |
| 130 | 1.2 | 2.4 | 0.01:1 to 100:1 | 0.05:1 to 20:1 | 0.1:1 to 20:1 |
| 131 | 1.2 | 2.5 | 0.01:1 to 100:1 | 0.05:1 to 20:1 | 0.1:1 to 20:1 |
| 132 | 1.2 | 2.6 | 0.01:1 to 100:1 | 0.05:1 to 20:1 | 0.1:1 to 20:1 |
| 133 | 1.2 | 2.7 | 0.01:1 to 100:1 | 0.05:1 to 20:1 | 0.1:1 to 20:1 |
| 134 | 1.2 | 2.8 | 0.01:1 to 100:1 | 0.05:1 to 20:1 | 0.1:1 to 20:1 |
| 135 | 1.2 | 2.9 | 0.01:1 to 100:1 | 0.05:1 to 20:1 | 0.1:1 to 20:1 |
| 136 | 1.2 | 2.10 | 0.01:1 to 100:1 | 0.05:1 to 20:1 | 0.1:1 to 20:1 |
| 137 | 1.2 | 2.11 | 0.01:1 to 100:1 | 0.05:1 to 20:1 | 0.1:1 to 20:1 |
| 138 | 1.2 | 2.12 | 0.01:1 to 100:1 | 0.05:1 to 20:1 | 0.1:1 to 20:1 |
| 139 | 1.2 | 2.13 | 0.01:1 to 100:1 | 0.05:1 to 20:1 | 0.1:1 to 20:1 |
| 140 | 1.2 | 2.14 | 0.01:1 to 100:1 | 0.05:1 to 20:1 | 0.1:1 to 20:1 |
| 141 | 1.2 | 2.15 | 0.01:1 to 100:1 | 0.05:1 to 20:1 | 0.1:1 to 20:1 |
| 142 | 1.2 | 2.16 | 0.01:1 to 100:1 | 0.05:1 to 20:1 | 0.1:1 to 20:1 |
| 143 | 1.2 | 2.17 | 0.01:1 to 100:1 | 0.05:1 to 20:1 | 0.1:1 to 20:1 |
| 144 | 1.2 | 2.18 | 0.01:1 to 100:1 | 0.05:1 to 20:1 | 0.1:1 to 20:1 |
| 145 | 1.2 | 2.19 | 0.01:1 to 100:1 | 0.05:1 to 20:1 | 0.1:1 to 20:1 |
| 146 | 1.2 | 2.20 | 0.01:1 to 100:1 | 0.05:1 to 20:1 | 0.1:1 to 20:1 |
| 147 | 1.2 | 2.21 | 0.01:1 to 100:1 | 0.05:1 to 20:1 | 0.1:1 to 20:1 |
| 148 | 1.2 | 2.22 | 0.01:1 to 100:1 | 0.05:1 to 20:1 | 0.1:1 to 20:1 |
| 149 | 1.2 | 2.23 | 0.01:1 to 100:1 | 0.05:1 to 20:1 | 0.1:1 to 20:1 |
| 150 | 1.2 | 2.24 | 0.01:1 to 100:1 | 0.05:1 to 20:1 | 0.1:1 to 20:1 |
| 151 | 1.2 | 2.25 | 0.01:1 to 100:1 | 0.05:1 to 20:1 | 0.1:1 to 20:1 |
| 152 | 1.2 | 2.26 | 0.01:1 to 100:1 | 0.05:1 to 20:1 | 0.1:1 to 20:1 |
| 153 | 1.2 | 2.27 | 0.01:1 to 100:1 | 0.05:1 to 20:1 | 0.1:1 to 20:1 |
| 154 | 1.2 | 2.28 | 0.01:1 to 100:1 | 0.05:1 to 20:1 | 0.1:1 to 20:1 |
| 155 | 1.2 | 2.29 | 0.01:1 to 100:1 | 0.05:1 to 20:1 | 0.1:1 to 20:1 |
| 156 | 1.2 | 2.30 | 0.01:1 to 100:1 | 0.05:1 to 20:1 | 0.1:1 to 20:1 |
| 157 | 1.2 | 2.31 | 0.01:1 to 100:1 | 0.05:1 to 20:1 | 0.1:1 to 20:1 |
| 158 | 1.2 | 2.32 | 0.01:1 to 100:1 | 0.05:1 to 20:1 | 0.1:1 to 20:1 |
| 159 | 1.2 | 2.33 | 0.01:1 to 100:1 | 0.05:1 to 20:1 | 0.1:1 to 20:1 |
| 160 | 1.2 | 2.34 | 0.01:1 to 100:1 | 0.05:1 to 20:1 | 0.1:1 to 20:1 |
| 161 | 1.2 | 2.35 | 0.01:1 to 100:1 | 0.05:1 to 20:1 | 0.1:1 to 20:1 |
| 162 | 1.2 | 2.36 | 0.01:1 to 100:1 | 0.05:1 to 20:1 | 0.1:1 to 20:1 |
| 163 | 1.2 | 2.37 | 0.01:1 to 100:1 | 0.05:1 to 20:1 | 0.1:1 to 20:1 |
| 164 | 1.2 | 2.38 | 0.01:1 to 100:1 | 0.05:1 to 20:1 | 0.1:1 to 20:1 |
| 165 | 1.2 | 2.39 | 0.01:1 to 100:1 | 0.05:1 to 20:1 | 0.1:1 to 20:1 |
| 166 | 1.2 | 2.40 | 0.01:1 to 100:1 | 0.05:1 to 20:1 | 0.1:1 to 20:1 |
| 167 | 1.2 | 2.41 | 0.01:1 to 100:1 | 0.05:1 to 20:1 | 0.1:1 to 20:1 |
| 168 | 1.2 | 2.42 | 0.01:1 to 100:1 | 0.05:1 to 20:1 | 0.1:1 to 20:1 |
| 169 | 1.2 | 2.43 | 0.01:1 to 100:1 | 0.05:1 to 20:1 | 0.1:1 to 20:1 |
| 170 | 1.2 | 2.44 | 0.01:1 to 100:1 | 0.05:1 to 20:1 | 0.1:1 to 20:1 |
| 171 | 1.2 | 2.45 | 0.01:1 to 100:1 | 0.05:1 to 20:1 | 0.1:1 to 20:1 |
| 172 | 1.2 | 2.46 | 0.01:1 to 100:1 | 0.05:1 to 20:1 | 0.1:1 to 20:1 |
| 173 | 1.2 | 2.47 | 0.01:1 to 100:1 | 0.05:1 to 20:1 | 0.1:1 to 20:1 |
| 174 | 1.2 | 2.48 | 0.01:1 to 100:1 | 0.05:1 to 20:1 | 0.1:1 to 20:1 |
| 175 | 1.2 | 2.49 | 0.01:1 to 100:1 | 0.05:1 to 20:1 | 0.1:1 to 20:1 |
| 176 | 1.2 | 2.50 | 0.01:1 to 100:1 | 0.05:1 to 20:1 | 0.1:1 to 20:1 |
| 177 | 1.2 | 2.51 | 0.01:1 to 100:1 | 0.05:1 to 20:1 | 0.1:1 to 20:1 |
| 178 | 1.2 | 2.52 | 0.01:1 to 100:1 | 0.05:1 to 20:1 | 0.1:1 to 20:1 |
| 179 | 1.2 | 2.53 | 0.01:1 to 100:1 | 0.05:1 to 20:1 | 0.1:1 to 20:1 |
| 180 | 1.2 | 2.54 | 0.01:1 to 100:1 | 0.05:1 to 20:1 | 0.1:1 to 20:1 |
| 181 | 1.2 | 2.55 | 0.01:1 to 100:1 | 0.05:1 to 20:1 | 0.1:1 to 20:1 |
| 182 | 1.2 | 2.56 | 0.01:1 to 100:1 | 0.05:1 to 20:1 | 0.1:1 to 20:1 |
| 183 | 1.2 | 2.57 | 0.01:1 to 100:1 | 0.05:1 to 20:1 | 0.1:1 to 20:1 |
| 184 | 1.2 | 2.58 | 0.01:1 to 100:1 | 0.05:1 to 20:1 | 0.1:1 to 20:1 |
| 185 | 1.2 | 2.59 | 0.01:1 to 100:1 | 0.05:1 to 20:1 | 0.1:1 to 20:1 |
| 186 | 1.2 | 2.60 | 0.01:1 to 100:1 | 0.05:1 to 20:1 | 0.1:1 to 20:1 |
| 187 | 1.2 | 2.61 | 0.01:1 to 100:1 | 0.05:1 to 20:1 | 0.1:1 to 20:1 |
| 188 | 1.2 | 2.62 | 0.01:1 to 100:1 | 0.05:1 to 20:1 | 0.1:1 to 20:1 |
| 189 | 1.2 | 2.63 | 0.01:1 to 100:1 | 0.05:1 to 20:1 | 0.1:1 to 20:1 |
| 190 | 1.2 | 2.64 | 0.01:1 to 100:1 | 0.05:1 to 20:1 | 0.1:1 to 20:1 |
| 191 | 1.2 | 2.65 | 0.01:1 to 100:1 | 0.05:1 to 20:1 | 0.1:1 to 20:1 |
| 192 | 1.2 | 2.66 | 0.01:1 to 100:1 | 0.05:1 to 20:1 | 0.1:1 to 20:1 |
| 193 | 1.2 | 2.67 | 0.01:1 to 100:1 | 0.05:1 to 20:1 | 0.1:1 to 20:1 |
| 194 | 1.2 | 2.68 | 0.01:1 to 100:1 | 0.05:1 to 20:1 | 0.1:1 to 20:1 |
| 195 | 1.2 | 2.69 | 0.01:1 to 100:1 | 0.05:1 to 20:1 | 0.1:1 to 20:1 |
| 196 | 1.2 | 2.70 | 0.01:1 to 100:1 | 0.05:1 to 20:1 | 0.1:1 to 20:1 |
| 197 | 1.2 | 2.71 | 0.01:1 to 100:1 | 0.05:1 to 20:1 | 0.1:1 to 20:1 |
| 198 | 1.2 | 2.72 | 0.01:1 to 100:1 | 0.05:1 to 20:1 | 0.1:1 to 20:1 |
| 199 | 1.2 | 2.73 | 0.01:1 to 100:1 | 0.05:1 to 20:1 | 0.1:1 to 20:1 |
| 200 | 1.2 | 2.74 | 0.01:1 to 100:1 | 0.05:1 to 20:1 | 0.1:1 to 20:1 |
| 201 | 1.2 | 2.75 | 0.01:1 to 100:1 | 0.05:1 to 20:1 | 0.1:1 to 20:1 |
| 202 | 1.2 | 2.76 | 0.01:1 to 100:1 | 0.05:1 to 20:1 | 0.1:1 to 20:1 |
| 203 | 1.2 | 2.77 | 0.01:1 to 100:1 | 0.05:1 to 20:1 | 0.1:1 to 20:1 |
| 204 | 1.2 | 2.78 | 0.01:1 to 100:1 | 0.05:1 to 20:1 | 0.1:1 to 20:1 |
| 205 | 1.2 | 2.79 | 0.01:1 to 100:1 | 0.05:1 to 20:1 | 0.1:1 to 20:1 |
| 206 | 1.2 | 2.80 | 0.01:1 to 100:1 | 0.05:1 to 20:1 | 0.1:1 to 20:1 |
| 207 | 1.2 | 2.81 | 0.01:1 to 100:1 | 0.05:1 to 20:1 | 0.1:1 to 20:1 |
| 208 | 1.2 | 2.82 | 0.01:1 to 100:1 | 0.05:1 to 20:1 | 0.1:1 to 20:1 |
| 209 | 1.2 | 2.83 | 0.01:1 to 100:1 | 0.05:1 to 20:1 | 0.1:1 to 20:1 |
| 210 | 1.2 | 2.84 | 0.01:1 to 100:1 | 0.05:1 to 20:1 | 0.1:1 to 20:1 |
| 211 | 1.2 | 2.85 | 0.01:1 to 100:1 | 0.05:1 to 20:1 | 0.1:1 to 20:1 |
| 212 | 1.2 | 2.86 | 0.01:1 to 100:1 | 0.05:1 to 20:1 | 0.1:1 to 20:1 |
| 213 | 1.2 | 2.87 | 0.01:1 to 100:1 | 0.05:1 to 20:1 | 0.1:1 to 20:1 |
| 214 | 1.2 | 2.88 | 0.01:1 to 100:1 | 0.05:1 to 20:1 | 0.1:1 to 20:1 |
| 215 | 1.2 | 2.89 | 0.01:1 to 100:1 | 0.05:1 to 20:1 | 0.1:1 to 20:1 |
| 216 | 1.2 | 2.90 | 0.01:1 to 100:1 | 0.05:1 to 20:1 | 0.1:1 to 20:1 |
| 217 | 1.2 | 2.91 | 0.01:1 to 100:1 | 0.05:1 to 20:1 | 0.1:1 to 20:1 |
| 218 | 1.2 | 2.92 | 0.01:1 to 100:1 | 0.05:1 to 20:1 | 0.1:1 to 20:1 |
| 219 | 1.2 | 2.93 | 0.01:1 to 100:1 | 0.05:1 to 20:1 | 0.1:1 to 20:1 |
| 220 | 1.2 | 2.94 | 0.01:1 to 100:1 | 0.05:1 to 20:1 | 0.1:1 to 20:1 |
| 221 | 1.2 | 2.95 | 0.01:1 to 100:1 | 0.05:1 to 20:1 | 0.1:1 to 20:1 |
| 222 | 1.2 | 2.96 | 0.01:1 to 100:1 | 0.05:1 to 20:1 | 0.1:1 to 20:1 |
| 223 | 1.2 | 2.97 | 0.01:1 to 100:1 | 0.05:1 to 20:1 | 0.1:1 to 20:1 |
| 224 | 1.2 | 2.98 | 0.01:1 to 100:1 | 0.05:1 to 20:1 | 0.1:1 to 20:1 |
| 225 | 1.2 | 2.99 | 0.01:1 to 100:1 | 0.05:1 to 20:1 | 0.1:1 to 20:1 |
| 226 | 1.2 | 2.100 | 0.01:1 to 100:1 | 0.05:1 to 20:1 | 0.1:1 to 20:1 |
| 227 | 1.2 | 2.101 | 0.01:1 to 100:1 | 0.05:1 to 20:1 | 0.1:1 to 20:1 |
| 228 | 1.2 | 2.102 | 0.01:1 to 100:1 | 0.05:1 to 20:1 | 0.1:1 to 20:1 |
| 229 | 1.2 | 2.103 | 0.01:1 to 100:1 | 0.05:1 to 20:1 | 0.1:1 to 20:1 |
| 230 | 1.2 | 2.104 | 0.01:1 to 100:1 | 0.05:1 to 20:1 | 0.1:1 to 20:1 |
| 231 | 1.2 | 2.105 | 0.01:1 to 100:1 | 0.05:1 to 20:1 | 0.1:1 to 20:1 |
| 232 | 1.2 | 2.106 | 0.01:1 to 100:1 | 0.05:1 to 20:1 | 0.1:1 to 20:1 |
| 233 | 1.2 | 2.107 | 0.01:1 to 100:1 | 0.05:1 to 20:1 | 0.1:1 to 20:1 |
| 234 | 1.2 | 2.108 | 0.01:1 to 100:1 | 0.05:1 to 20:1 | 0.1:1 to 20:1 |
| 235 | 1.2 | 2.109 | 0.01:1 to 100:1 | 0.05:1 to 20:1 | 0.1:1 to 20:1 |
| 236 | 1.2 | 2.110 | 0.01:1 to 100:1 | 0.05:1 to 20:1 | 0.1:1 to 20:1 |
| 237 | 1.2 | 2.111 | 0.01:1 to 100:1 | 0.05:1 to 20:1 | 0.1:1 to 20:1 |
| 238 | 1.2 | 2.112 | 0.01:1 to 100:1 | 0.05:1 to 20:1 | 0.1:1 to 20:1 |
| 239 | 1.2 | 2.113 | 0.01:1 to 100:1 | 0.05:1 to 20:1 | 0.1:1 to 20:1 |
| 240 | 1.2 | 2.114 | 0.01:1 to 100:1 | 0.05:1 to 20:1 | 0.1:1 to 20:1 |
| 241 | 1.2 | 2.115 | 0.01:1 to 100:1 | 0.05:1 to 20:1 | 0.1:1 to 20:1 |
| 242 | 1.2 | 2.116 | 0.01:1 to 100:1 | 0.05:1 to 20:1 | 0.1:1 to 20:1 |
| 243 | 1.2 | 2.117 | 0.01:1 to 100:1 | 0.05:1 to 20:1 | 0.1:1 to 20:1 |
| 244 | 1.2 | 2.118 | 0.01:1 to 100:1 | 0.05:1 to 20:1 | 0.1:1 to 20:1 |
| 245 | 1.2 | 2.119 | 0.01:1 to 100:1 | 0.05:1 to 20:1 | 0.1:1 to 20:1 |
| 246 | 1.2 | 2.120 | 0.01:1 to 100:1 | 0.05:1 to 20:1 | 0.1:1 to 20:1 |
| 247 | 1.2 | 2.121 | 0.01:1 to 100:1 | 0.05:1 to 20:1 | 0.1:1 to 20:1 |
| 248 | 1.2 | 2.122 | 0.01:1 to 100:1 | 0.05:1 to 20:1 | 0.1:1 to 20:1 |
| 249 | 1.2 | 2.123 | 0.01:1 to 100:1 | 0.05:1 to 20:1 | 0.1:1 to 20:1 |
| 250 | 1.2 | 2.124 | 0.01:1 to 100:1 | 0.05:1 to 20:1 | 0.1:1 to 20:1 |
| 251 | 1.2 | 2.125 | 0.01:1 to 100:1 | 0.05:1 to 20:1 | 0.1:1 to 20:1 |

TABLE 2-continued

Compositions of the Invention

| Composition Number | A Cmpd of formula (I) | B Cmpd of formula (II) | Typical Weight Ratio | Preferred Weight Ratio | More Preferred Weight Ratio |
|---|---|---|---|---|---|
| 252 | 1.2 | 2.126 | 0.01:1 to 100:1 | 0.05:1 to 20:1 | 0.1:1 to 20:1 |
| 253 | 1.3 | 2.1 | 0.01:1 to 100:1 | 0.05:1 to 20:1 | 0.1:1 to 20:1 |
| 254 | 1.3 | 2.2 | 0.01:1 to 100:1 | 0.05:1 to 20:1 | 0.1:1 to 20:1 |
| 255 | 1.3 | 2.3 | 0.01:1 to 100:1 | 0.05:1 to 20:1 | 0.1:1 to 20:1 |
| 256 | 1.3 | 2.4 | 0.01:1 to 100:1 | 0.05:1 to 20:1 | 0.1:1 to 20:1 |
| 257 | 1.3 | 2.5 | 0.01:1 to 100:1 | 0.05:1 to 20:1 | 0.1:1 to 20:1 |
| 258 | 1.3 | 2.6 | 0.01:1 to 100:1 | 0.05:1 to 20:1 | 0.1:1 to 20:1 |
| 259 | 1.3 | 2.7 | 0.01:1 to 100:1 | 0.05:1 to 20:1 | 0.1:1 to 20:1 |
| 260 | 1.3 | 2.8 | 0.01:1 to 100:1 | 0.05:1 to 20:1 | 0.1:1 to 20:1 |
| 261 | 1.3 | 2.9 | 0.01:1 to 100:1 | 0.05:1 to 20:1 | 0.1:1 to 20:1 |
| 262 | 1.3 | 2.10 | 0.01:1 to 100:1 | 0.05:1 to 20:1 | 0.1:1 to 20:1 |
| 263 | 1.3 | 2.11 | 0.01:1 to 100:1 | 0.05:1 to 20:1 | 0.1:1 to 20:1 |
| 264 | 1.3 | 2.12 | 0.01:1 to 100:1 | 0.05:1 to 20:1 | 0.1:1 to 20:1 |
| 265 | 1.3 | 2.13 | 0.01:1 to 100:1 | 0.05:1 to 20:1 | 0.1:1 to 20:1 |
| 266 | 1.3 | 2.14 | 0.01:1 to 100:1 | 0.05:1 to 20:1 | 0.1:1 to 20:1 |
| 267 | 1.3 | 2.15 | 0.01:1 to 100:1 | 0.05:1 to 20:1 | 0.1:1 to 20:1 |
| 268 | 1.3 | 2.16 | 0.01:1 to 100:1 | 0.05:1 to 20:1 | 0.1:1 to 20:1 |
| 269 | 1.3 | 2.17 | 0.01:1 to 100:1 | 0.05:1 to 20:1 | 0.1:1 to 20:1 |
| 270 | 1.3 | 2.18 | 0.01:1 to 100:1 | 0.05:1 to 20:1 | 0.1:1 to 20:1 |
| 271 | 1.3 | 2.19 | 0.01:1 to 100:1 | 0.05:1 to 20:1 | 0.1:1 to 20:1 |
| 272 | 1.3 | 2.20 | 0.01:1 to 100:1 | 0.05:1 to 20:1 | 0.1:1 to 20:1 |
| 273 | 1.3 | 2.21 | 0.01:1 to 100:1 | 0.05:1 to 20:1 | 0.1:1 to 20:1 |
| 274 | 1.3 | 2.22 | 0.01:1 to 100:1 | 0.05:1 to 20:1 | 0.1:1 to 20:1 |
| 275 | 1.3 | 2.23 | 0.01:1 to 100:1 | 0.05:1 to 20:1 | 0.1:1 to 20:1 |
| 276 | 1.3 | 2.24 | 0.01:1 to 100:1 | 0.05:1 to 20:1 | 0.1:1 to 20:1 |
| 277 | 1.3 | 2.25 | 0.01:1 to 100:1 | 0.05:1 to 20:1 | 0.1:1 to 20:1 |
| 278 | 1.3 | 2.26 | 0.01:1 to 100:1 | 0.05:1 to 20:1 | 0.1:1 to 20:1 |
| 279 | 1.3 | 2.27 | 0.01:1 to 100:1 | 0.05:1 to 20:1 | 0.1:1 to 20:1 |
| 280 | 1.3 | 2.28 | 0.01:1 to 100:1 | 0.05:1 to 20:1 | 0.1:1 to 20:1 |
| 281 | 1.3 | 2.29 | 0.01:1 to 100:1 | 0.05:1 to 20:1 | 0.1:1 to 20:1 |
| 282 | 1.3 | 2.30 | 0.01:1 to 100:1 | 0.05:1 to 20:1 | 0.1:1 to 20:1 |
| 283 | 1.3 | 2.31 | 0.01:1 to 100:1 | 0.05:1 to 20:1 | 0.1:1 to 20:1 |
| 284 | 1.3 | 2.32 | 0.01:1 to 100:1 | 0.05:1 to 20:1 | 0.1:1 to 20:1 |
| 285 | 1.3 | 2.33 | 0.01:1 to 100:1 | 0.05:1 to 20:1 | 0.1:1 to 20:1 |
| 286 | 1.3 | 2.34 | 0.01:1 to 100:1 | 0.05:1 to 20:1 | 0.1:1 to 20:1 |
| 287 | 1.3 | 2.35 | 0.01:1 to 100:1 | 0.05:1 to 20:1 | 0.1:1 to 20:1 |
| 288 | 1.3 | 2.36 | 0.01:1 to 100:1 | 0.05:1 to 20:1 | 0.1:1 to 20:1 |
| 289 | 1.3 | 2.37 | 0.01:1 to 100:1 | 0.05:1 to 20:1 | 0.1:1 to 20:1 |
| 290 | 1.3 | 2.38 | 0.01:1 to 100:1 | 0.05:1 to 20:1 | 0.1:1 to 20:1 |
| 291 | 1.3 | 2.39 | 0.01:1 to 100:1 | 0.05:1 to 20:1 | 0.1:1 to 20:1 |
| 292 | 1.3 | 2.40 | 0.01:1 to 100:1 | 0.05:1 to 20:1 | 0.1:1 to 20:1 |
| 293 | 1.3 | 2.41 | 0.01:1 to 100:1 | 0.05:1 to 20:1 | 0.1:1 to 20:1 |
| 294 | 1.3 | 2.42 | 0.01:1 to 100:1 | 0.05:1 to 20:1 | 0.1:1 to 20:1 |
| 295 | 1.3 | 2.43 | 0.01:1 to 100:1 | 0.05:1 to 20:1 | 0.1:1 to 20:1 |
| 296 | 1.3 | 2.44 | 0.01:1 to 100:1 | 0.05:1 to 20:1 | 0.1:1 to 20:1 |
| 297 | 1.3 | 2.45 | 0.01:1 to 100:1 | 0.05:1 to 20:1 | 0.1:1 to 20:1 |
| 298 | 1.3 | 2.46 | 0.01:1 to 100:1 | 0.05:1 to 20:1 | 0.1:1 to 20:1 |
| 299 | 1.3 | 2.47 | 0.01:1 to 100:1 | 0.05:1 to 20:1 | 0.1:1 to 20:1 |
| 300 | 1.3 | 2.48 | 0.01:1 to 100:1 | 0.05:1 to 20:1 | 0.1:1 to 20:1 |
| 301 | 1.3 | 2.49 | 0.01:1 to 100:1 | 0.05:1 to 20:1 | 0.1:1 to 20:1 |
| 302 | 1.3 | 2.50 | 0.01:1 to 100:1 | 0.05:1 to 20:1 | 0.1:1 to 20:1 |
| 303 | 1.3 | 2.51 | 0.01:1 to 100:1 | 0.05:1 to 20:1 | 0.1:1 to 20:1 |
| 304 | 1.3 | 2.52 | 0.01:1 to 100:1 | 0.05:1 to 20:1 | 0.1:1 to 20:1 |
| 305 | 1.3 | 2.53 | 0.01:1 to 100:1 | 0.05:1 to 20:1 | 0.1:1 to 20:1 |
| 306 | 1.3 | 2.54 | 0.01:1 to 100:1 | 0.05:1 to 20:1 | 0.1:1 to 20:1 |
| 307 | 1.3 | 2.55 | 0.01:1 to 100:1 | 0.05:1 to 20:1 | 0.1:1 to 20:1 |
| 308 | 1.3 | 2.56 | 0.01:1 to 100:1 | 0.05:1 to 20:1 | 0.1:1 to 20:1 |
| 309 | 1.3 | 2.57 | 0.01:1 to 100:1 | 0.05:1 to 20:1 | 0.1:1 to 20:1 |
| 310 | 1.3 | 2.58 | 0.01:1 to 100:1 | 0.05:1 to 20:1 | 0.1:1 to 20:1 |
| 311 | 1.3 | 2.59 | 0.01:1 to 100:1 | 0.05:1 to 20:1 | 0.1:1 to 20:1 |
| 312 | 1.3 | 2.60 | 0.01:1 to 100:1 | 0.05:1 to 20:1 | 0.1:1 to 20:1 |
| 313 | 1.3 | 2.61 | 0.01:1 to 100:1 | 0.05:1 to 20:1 | 0.1:1 to 20:1 |
| 314 | 1.3 | 2.62 | 0.01:1 to 100:1 | 0.05:1 to 20:1 | 0.1:1 to 20:1 |
| 315 | 1.3 | 2.63 | 0.01:1 to 100:1 | 0.05:1 to 20:1 | 0.1:1 to 20:1 |
| 316 | 1.3 | 2.64 | 0.01:1 to 100:1 | 0.05:1 to 20:1 | 0.1:1 to 20:1 |
| 317 | 1.3 | 2.65 | 0.01:1 to 100:1 | 0.05:1 to 20:1 | 0.1:1 to 20:1 |
| 318 | 1.3 | 2.66 | 0.01:1 to 100:1 | 0.05:1 to 20:1 | 0.1:1 to 20:1 |
| 319 | 1.3 | 2.67 | 0.01:1 to 100:1 | 0.05:1 to 20:1 | 0.1:1 to 20:1 |
| 320 | 1.3 | 2.68 | 0.01:1 to 100:1 | 0.05:1 to 20:1 | 0.1:1 to 20:1 |
| 321 | 1.3 | 2.69 | 0.01:1 to 100:1 | 0.05:1 to 20:1 | 0.1:1 to 20:1 |
| 322 | 1.3 | 2.70 | 0.01:1 to 100:1 | 0.05:1 to 20:1 | 0.1:1 to 20:1 |
| 323 | 1.3 | 2.71 | 0.01:1 to 100:1 | 0.05:1 to 20:1 | 0.1:1 to 20:1 |
| 324 | 1.3 | 2.72 | 0.01:1 to 100:1 | 0.05:1 to 20:1 | 0.1:1 to 20:1 |
| 325 | 1.3 | 2.73 | 0.01:1 to 100:1 | 0.05:1 to 20:1 | 0.1:1 to 20:1 |
| 326 | 1.3 | 2.74 | 0.01:1 to 100:1 | 0.05:1 to 20:1 | 0.1:1 to 20:1 |
| 327 | 1.3 | 2.75 | 0.01:1 to 100:1 | 0.05:1 to 20:1 | 0.1:1 to 20:1 |
| 328 | 1.3 | 2.76 | 0.01:1 to 100:1 | 0.05:1 to 20:1 | 0.1:1 to 20:1 |
| 329 | 1.3 | 2.77 | 0.01:1 to 100:1 | 0.05:1 to 20:1 | 0.1:1 to 20:1 |
| 330 | 1.3 | 2.78 | 0.01:1 to 100:1 | 0.05:1 to 20:1 | 0.1:1 to 20:1 |
| 331 | 1.3 | 2.79 | 0.01:1 to 100:1 | 0.05:1 to 20:1 | 0.1:1 to 20:1 |
| 332 | 1.3 | 2.80 | 0.01:1 to 100:1 | 0.05:1 to 20:1 | 0.1:1 to 20:1 |
| 333 | 1.3 | 2.81 | 0.01:1 to 100:1 | 0.05:1 to 20:1 | 0.1:1 to 20:1 |
| 334 | 1.3 | 2.82 | 0.01:1 to 100:1 | 0.05:1 to 20:1 | 0.1:1 to 20:1 |
| 335 | 1.3 | 2.83 | 0.01:1 to 100:1 | 0.05:1 to 20:1 | 0.1:1 to 20:1 |
| 336 | 1.3 | 2.84 | 0.01:1 to 100:1 | 0.05:1 to 20:1 | 0.1:1 to 20:1 |
| 337 | 1.3 | 2.85 | 0.01:1 to 100:1 | 0.05:1 to 20:1 | 0.1:1 to 20:1 |
| 338 | 1.3 | 2.86 | 0.01:1 to 100:1 | 0.05:1 to 20:1 | 0.1:1 to 20:1 |
| 339 | 1.3 | 2.87 | 0.01:1 to 100:1 | 0.05:1 to 20:1 | 0.1:1 to 20:1 |
| 340 | 1.3 | 2.88 | 0.01:1 to 100:1 | 0.05:1 to 20:1 | 0.1:1 to 20:1 |
| 341 | 1.3 | 2.89 | 0.01:1 to 100:1 | 0.05:1 to 20:1 | 0.1:1 to 20:1 |
| 342 | 1.3 | 2.90 | 0.01:1 to 100:1 | 0.05:1 to 20:1 | 0.1:1 to 20:1 |
| 343 | 1.3 | 2.91 | 0.01:1 to 100:1 | 0.05:1 to 20:1 | 0.1:1 to 20:1 |
| 344 | 1.3 | 2.92 | 0.01:1 to 100:1 | 0.05:1 to 20:1 | 0.1:1 to 20:1 |
| 345 | 1.3 | 2.93 | 0.01:1 to 100:1 | 0.05:1 to 20:1 | 0.1:1 to 20:1 |
| 346 | 1.3 | 2.94 | 0.01:1 to 100:1 | 0.05:1 to 20:1 | 0.1:1 to 20:1 |
| 347 | 1.3 | 2.95 | 0.01:1 to 100:1 | 0.05:1 to 20:1 | 0.1:1 to 20:1 |
| 348 | 1.3 | 2.96 | 0.01:1 to 100:1 | 0.05:1 to 20:1 | 0.1:1 to 20:1 |
| 349 | 1.3 | 2.97 | 0.01:1 to 100:1 | 0.05:1 to 20:1 | 0.1:1 to 20:1 |
| 350 | 1.3 | 2.98 | 0.01:1 to 100:1 | 0.05:1 to 20:1 | 0.1:1 to 20:1 |
| 351 | 1.3 | 2.99 | 0.01:1 to 100:1 | 0.05:1 to 20:1 | 0.1:1 to 20:1 |
| 352 | 1.3 | 2.100 | 0.01:1 to 100:1 | 0.05:1 to 20:1 | 0.1:1 to 20:1 |
| 353 | 1.3 | 2.101 | 0.01:1 to 100:1 | 0.05:1 to 20:1 | 0.1:1 to 20:1 |
| 354 | 1.3 | 2.102 | 0.01:1 to 100:1 | 0.05:1 to 20:1 | 0.1:1 to 20:1 |
| 355 | 1.3 | 2.103 | 0.01:1 to 100:1 | 0.05:1 to 20:1 | 0.1:1 to 20:1 |
| 356 | 1.3 | 2.104 | 0.01:1 to 100:1 | 0.05:1 to 20:1 | 0.1:1 to 20:1 |
| 357 | 1.3 | 2.105 | 0.01:1 to 100:1 | 0.05:1 to 20:1 | 0.1:1 to 20:1 |
| 358 | 1.3 | 2.106 | 0.01:1 to 100:1 | 0.05:1 to 20:1 | 0.1:1 to 20:1 |
| 359 | 1.3 | 2.107 | 0.01:1 to 100:1 | 0.05:1 to 20:1 | 0.1:1 to 20:1 |
| 360 | 1.3 | 2.108 | 0.01:1 to 100:1 | 0.05:1 to 20:1 | 0.1:1 to 20:1 |
| 361 | 1.3 | 2.109 | 0.01:1 to 100:1 | 0.05:1 to 20:1 | 0.1:1 to 20:1 |
| 362 | 1.3 | 2.110 | 0.01:1 to 100:1 | 0.05:1 to 20:1 | 0.1:1 to 20:1 |
| 363 | 1.3 | 2.111 | 0.01:1 to 100:1 | 0.05:1 to 20:1 | 0.1:1 to 20:1 |
| 364 | 1.3 | 2.112 | 0.01:1 to 100:1 | 0.05:1 to 20:1 | 0.1:1 to 20:1 |
| 365 | 1.3 | 2.113 | 0.01:1 to 100:1 | 0.05:1 to 20:1 | 0.1:1 to 20:1 |
| 366 | 1.3 | 2.114 | 0.01:1 to 100:1 | 0.05:1 to 20:1 | 0.1:1 to 20:1 |
| 367 | 1.3 | 2.115 | 0.01:1 to 100:1 | 0.05:1 to 20:1 | 0.1:1 to 20:1 |
| 368 | 1.3 | 2.116 | 0.01:1 to 100:1 | 0.05:1 to 20:1 | 0.1:1 to 20:1 |
| 369 | 1.3 | 2.117 | 0.01:1 to 100:1 | 0.05:1 to 20:1 | 0.1:1 to 20:1 |
| 370 | 1.3 | 2.118 | 0.01:1 to 100:1 | 0.05:1 to 20:1 | 0.1:1 to 20:1 |
| 371 | 1.3 | 2.119 | 0.01:1 to 100:1 | 0.05:1 to 20:1 | 0.1:1 to 20:1 |
| 372 | 1.3 | 2.120 | 0.01:1 to 100:1 | 0.05:1 to 20:1 | 0.1:1 to 20:1 |
| 373 | 1.3 | 2.121 | 0.01:1 to 100:1 | 0.05:1 to 20:1 | 0.1:1 to 20:1 |
| 374 | 1.3 | 2.122 | 0.01:1 to 100:1 | 0.05:1 to 20:1 | 0.1:1 to 20:1 |
| 375 | 1.3 | 2.123 | 0.01:1 to 100:1 | 0.05:1 to 20:1 | 0.1:1 to 20:1 |
| 376 | 1.3 | 2.124 | 0.01:1 to 100:1 | 0.05:1 to 20:1 | 0.1:1 to 20:1 |
| 377 | 1.3 | 2.125 | 0.01:1 to 100:1 | 0.05:1 to 20:1 | 0.1:1 to 20:1 |
| 378 | 1.3 | 2.126 | 0.01:1 to 100:1 | 0.05:1 to 20:1 | 0.1:1 to 20:1 |
| 379 | 1.4 | 2.1 | 0.01:1 to 100:1 | 0.05:1 to 20:1 | 0.1:1 to 20:1 |
| 380 | 1.4 | 2.2 | 0.01:1 to 100:1 | 0.05:1 to 20:1 | 0.1:1 to 20:1 |
| 381 | 1.4 | 2.3 | 0.01:1 to 100:1 | 0.05:1 to 20:1 | 0.1:1 to 20:1 |
| 382 | 1.4 | 2.4 | 0.01:1 to 100:1 | 0.05:1 to 20:1 | 0.1:1 to 20:1 |
| 383 | 1.4 | 2.5 | 0.01:1 to 100:1 | 0.05:1 to 20:1 | 0.1:1 to 20:1 |
| 384 | 1.4 | 2.6 | 0.01:1 to 100:1 | 0.05:1 to 20:1 | 0.1:1 to 20:1 |
| 385 | 1.4 | 2.7 | 0.01:1 to 100:1 | 0.05:1 to 20:1 | 0.1:1 to 20:1 |
| 386 | 1.4 | 2.8 | 0.01:1 to 100:1 | 0.05:1 to 20:1 | 0.1:1 to 20:1 |
| 387 | 1.4 | 2.9 | 0.01:1 to 100:1 | 0.05:1 to 20:1 | 0.1:1 to 20:1 |
| 388 | 1.4 | 2.10 | 0.01:1 to 100:1 | 0.05:1 to 20:1 | 0.1:1 to 20:1 |
| 389 | 1.4 | 2.11 | 0.01:1 to 100:1 | 0.05:1 to 20:1 | 0.1:1 to 20:1 |
| 390 | 1.4 | 2.12 | 0.01:1 to 100:1 | 0.05:1 to 20:1 | 0.1:1 to 20:1 |
| 391 | 1.4 | 2.13 | 0.01:1 to 100:1 | 0.05:1 to 20:1 | 0.1:1 to 20:1 |
| 392 | 1.4 | 2.14 | 0.01:1 to 100:1 | 0.05:1 to 20:1 | 0.1:1 to 20:1 |
| 393 | 1.4 | 2.15 | 0.01:1 to 100:1 | 0.05:1 to 20:1 | 0.1:1 to 20:1 |

TABLE 2-continued

Compositions of the Invention

| Composition Number | A Cmpd of formula (I) | B Cmpd of formula (II) | Typical Weight Ratio | Preferred Weight Ratio | More Preferred Weight Ratio |
|---|---|---|---|---|---|
| 394 | 1.4 | 2.16 | 0.01:1 to 100:1 | 0.05:1 to 20:1 | 0.1:1 to 20:1 |
| 395 | 1.4 | 2.17 | 0.01:1 to 100:1 | 0.05:1 to 20:1 | 0.1:1 to 20:1 |
| 396 | 1.4 | 2.18 | 0.01:1 to 100:1 | 0.05:1 to 20:1 | 0.1:1 to 20:1 |
| 397 | 1.4 | 2.19 | 0.01:1 to 100:1 | 0.05:1 to 20:1 | 0.1:1 to 20:1 |
| 398 | 1.4 | 2.20 | 0.01:1 to 100:1 | 0.05:1 to 20:1 | 0.1:1 to 20:1 |
| 399 | 1.4 | 2.21 | 0.01:1 to 100:1 | 0.05:1 to 20:1 | 0.1:1 to 20:1 |
| 400 | 1.4 | 2.22 | 0.01:1 to 100:1 | 0.05:1 to 20:1 | 0.1:1 to 20:1 |
| 401 | 1.4 | 2.23 | 0.01:1 to 100:1 | 0.05:1 to 20:1 | 0.1:1 to 20:1 |
| 402 | 1.4 | 2.24 | 0.01:1 to 100:1 | 0.05:1 to 20:1 | 0.1:1 to 20:1 |
| 403 | 1.4 | 2.25 | 0.01:1 to 100:1 | 0.05:1 to 20:1 | 0.1:1 to 20:1 |
| 404 | 1.4 | 2.26 | 0.01:1 to 100:1 | 0.05:1 to 20:1 | 0.1:1 to 20:1 |
| 405 | 1.4 | 2.27 | 0.01:1 to 100:1 | 0.05:1 to 20:1 | 0.1:1 to 20:1 |
| 406 | 1.4 | 2.28 | 0.01:1 to 100:1 | 0.05:1 to 20:1 | 0.1:1 to 20:1 |
| 407 | 1.4 | 2.29 | 0.01:1 to 100:1 | 0.05:1 to 20:1 | 0.1:1 to 20:1 |
| 408 | 1.4 | 2.30 | 0.01:1 to 100:1 | 0.05:1 to 20:1 | 0.1:1 to 20:1 |
| 409 | 1.4 | 2.31 | 0.01:1 to 100:1 | 0.05:1 to 20:1 | 0.1:1 to 20:1 |
| 410 | 1.4 | 2.32 | 0.01:1 to 100:1 | 0.05:1 to 20:1 | 0.1:1 to 20:1 |
| 411 | 1.4 | 2.33 | 0.01:1 to 100:1 | 0.05:1 to 20:1 | 0.1:1 to 20:1 |
| 412 | 1.4 | 2.34 | 0.01:1 to 100:1 | 0.05:1 to 20:1 | 0.1:1 to 20:1 |
| 413 | 1.4 | 2.35 | 0.01:1 to 100:1 | 0.05:1 to 20:1 | 0.1:1 to 20:1 |
| 414 | 1.4 | 2.36 | 0.01:1 to 100:1 | 0.05:1 to 20:1 | 0.1:1 to 20:1 |
| 415 | 1.4 | 2.37 | 0.01:1 to 100:1 | 0.05:1 to 20:1 | 0.1:1 to 20:1 |
| 416 | 1.4 | 2.38 | 0.01:1 to 100:1 | 0.05:1 to 20:1 | 0.1:1 to 20:1 |
| 417 | 1.4 | 2.39 | 0.01:1 to 100:1 | 0.05:1 to 20:1 | 0.1:1 to 20:1 |
| 418 | 1.4 | 2.40 | 0.01:1 to 100:1 | 0.05:1 to 20:1 | 0.1:1 to 20:1 |
| 419 | 1.4 | 2.41 | 0.01:1 to 100:1 | 0.05:1 to 20:1 | 0.1:1 to 20:1 |
| 420 | 1.4 | 2.42 | 0.01:1 to 100:1 | 0.05:1 to 20:1 | 0.1:1 to 20:1 |
| 421 | 1.4 | 2.43 | 0.01:1 to 100:1 | 0.05:1 to 20:1 | 0.1:1 to 20:1 |
| 422 | 1.4 | 2.44 | 0.01:1 to 100:1 | 0.05:1 to 20:1 | 0.1:1 to 20:1 |
| 423 | 1.4 | 2.45 | 0.01:1 to 100:1 | 0.05:1 to 20:1 | 0.1:1 to 20:1 |
| 424 | 1.4 | 2.46 | 0.01:1 to 100:1 | 0.05:1 to 20:1 | 0.1:1 to 20:1 |
| 425 | 1.4 | 2.47 | 0.01:1 to 100:1 | 0.05:1 to 20:1 | 0.1:1 to 20:1 |
| 426 | 1.4 | 2.48 | 0.01:1 to 100:1 | 0.05:1 to 20:1 | 0.1:1 to 20:1 |
| 427 | 1.4 | 2.49 | 0.01:1 to 100:1 | 0.05:1 to 20:1 | 0.1:1 to 20:1 |
| 428 | 1.4 | 2.50 | 0.01:1 to 100:1 | 0.05:1 to 20:1 | 0.1:1 to 20:1 |
| 429 | 1.4 | 2.51 | 0.01:1 to 100:1 | 0.05:1 to 20:1 | 0.1:1 to 20:1 |
| 430 | 1.4 | 2.52 | 0.01:1 to 100:1 | 0.05:1 to 20:1 | 0.1:1 to 20:1 |
| 431 | 1.4 | 2.53 | 0.01:1 to 100:1 | 0.05:1 to 20:1 | 0.1:1 to 20:1 |
| 432 | 1.4 | 2.54 | 0.01:1 to 100:1 | 0.05:1 to 20:1 | 0.1:1 to 20:1 |
| 433 | 1.4 | 2.55 | 0.01:1 to 100:1 | 0.05:1 to 20:1 | 0.1:1 to 20:1 |
| 434 | 1.4 | 2.56 | 0.01:1 to 100:1 | 0.05:1 to 20:1 | 0.1:1 to 20:1 |
| 435 | 1.4 | 2.57 | 0.01:1 to 100:1 | 0.05:1 to 20:1 | 0.1:1 to 20:1 |
| 436 | 1.4 | 2.58 | 0.01:1 to 100:1 | 0.05:1 to 20:1 | 0.1:1 to 20:1 |
| 437 | 1.4 | 2.59 | 0.01:1 to 100:1 | 0.05:1 to 20:1 | 0.1:1 to 20:1 |
| 438 | 1.4 | 2.60 | 0.01:1 to 100:1 | 0.05:1 to 20:1 | 0.1:1 to 20:1 |
| 439 | 1.4 | 2.61 | 0.01:1 to 100:1 | 0.05:1 to 20:1 | 0.1:1 to 20:1 |
| 440 | 1.4 | 2.62 | 0.01:1 to 100:1 | 0.05:1 to 20:1 | 0.1:1 to 20:1 |
| 441 | 1.4 | 2.63 | 0.01:1 to 100:1 | 0.05:1 to 20:1 | 0.1:1 to 20:1 |
| 442 | 1.4 | 2.64 | 0.01:1 to 100:1 | 0.05:1 to 20:1 | 0.1:1 to 20:1 |
| 443 | 1.4 | 2.65 | 0.01:1 to 100:1 | 0.05:1 to 20:1 | 0.1:1 to 20:1 |
| 444 | 1.4 | 2.66 | 0.01:1 to 100:1 | 0.05:1 to 20:1 | 0.1:1 to 20:1 |
| 445 | 1.4 | 2.67 | 0.01:1 to 100:1 | 0.05:1 to 20:1 | 0.1:1 to 20:1 |
| 446 | 1.4 | 2.68 | 0.01:1 to 100:1 | 0.05:1 to 20:1 | 0.1:1 to 20:1 |
| 447 | 1.4 | 2.69 | 0.01:1 to 100:1 | 0.05:1 to 20:1 | 0.1:1 to 20:1 |
| 448 | 1.4 | 2.70 | 0.01:1 to 100:1 | 0.05:1 to 20:1 | 0.1:1 to 20:1 |
| 449 | 1.4 | 2.71 | 0.01:1 to 100:1 | 0.05:1 to 20:1 | 0.1:1 to 20:1 |
| 450 | 1.4 | 2.72 | 0.01:1 to 100:1 | 0.05:1 to 20:1 | 0.1:1 to 20:1 |
| 451 | 1.4 | 2.73 | 0.01:1 to 100:1 | 0.05:1 to 20:1 | 0.1:1 to 20:1 |
| 452 | 1.4 | 2.74 | 0.01:1 to 100:1 | 0.05:1 to 20:1 | 0.1:1 to 20:1 |
| 453 | 1.4 | 2.75 | 0.01:1 to 100:1 | 0.05:1 to 20:1 | 0.1:1 to 20:1 |
| 454 | 1.4 | 2.76 | 0.01:1 to 100:1 | 0.05:1 to 20:1 | 0.1:1 to 20:1 |
| 455 | 1.4 | 2.77 | 0.01:1 to 100:1 | 0.05:1 to 20:1 | 0.1:1 to 20:1 |
| 456 | 1.4 | 2.78 | 0.01:1 to 100:1 | 0.05:1 to 20:1 | 0.1:1 to 20:1 |
| 457 | 1.4 | 2.79 | 0.01:1 to 100:1 | 0.05:1 to 20:1 | 0.1:1 to 20:1 |
| 458 | 1.4 | 2.80 | 0.01:1 to 100:1 | 0.05:1 to 20:1 | 0.1:1 to 20:1 |
| 459 | 1.4 | 2.81 | 0.01:1 to 100:1 | 0.05:1 to 20:1 | 0.1:1 to 20:1 |
| 460 | 1.4 | 2.82 | 0.01:1 to 100:1 | 0.05:1 to 20:1 | 0.1:1 to 20:1 |
| 461 | 1.4 | 2.83 | 0.01:1 to 100:1 | 0.05:1 to 20:1 | 0.1:1 to 20:1 |
| 462 | 1.4 | 2.84 | 0.01:1 to 100:1 | 0.05:1 to 20:1 | 0.1:1 to 20:1 |
| 463 | 1.4 | 2.85 | 0.01:1 to 100:1 | 0.05:1 to 20:1 | 0.1:1 to 20:1 |
| 464 | 1.4 | 2.86 | 0.01:1 to 100:1 | 0.05:1 to 20:1 | 0.1:1 to 20:1 |
| 465 | 1.4 | 2.87 | 0.01:1 to 100:1 | 0.05:1 to 20:1 | 0.1:1 to 20:1 |
| 466 | 1.4 | 2.88 | 0.01:1 to 100:1 | 0.05:1 to 20:1 | 0.1:1 to 20:1 |
| 467 | 1.4 | 2.89 | 0.01:1 to 100:1 | 0.05:1 to 20:1 | 0.1:1 to 20:1 |
| 468 | 1.4 | 2.90 | 0.01:1 to 100:1 | 0.05:1 to 20:1 | 0.1:1 to 20:1 |
| 469 | 1.4 | 2.91 | 0.01:1 to 100:1 | 0.05:1 to 20:1 | 0.1:1 to 20:1 |
| 470 | 1.4 | 2.92 | 0.01:1 to 100:1 | 0.05:1 to 20:1 | 0.1:1 to 20:1 |
| 471 | 1.4 | 2.93 | 0.01:1 to 100:1 | 0.05:1 to 20:1 | 0.1:1 to 20:1 |
| 472 | 1.4 | 2.94 | 0.01:1 to 100:1 | 0.05:1 to 20:1 | 0.1:1 to 20:1 |
| 473 | 1.4 | 2.95 | 0.01:1 to 100:1 | 0.05:1 to 20:1 | 0.1:1 to 20:1 |
| 474 | 1.4 | 2.96 | 0.01:1 to 100:1 | 0.05:1 to 20:1 | 0.1:1 to 20:1 |
| 475 | 1.4 | 2.97 | 0.01:1 to 100:1 | 0.05:1 to 20:1 | 0.1:1 to 20:1 |
| 476 | 1.4 | 2.98 | 0.01:1 to 100:1 | 0.05:1 to 20:1 | 0.1:1 to 20:1 |
| 477 | 1.4 | 2.99 | 0.01:1 to 100:1 | 0.05:1 to 20:1 | 0.1:1 to 20:1 |
| 478 | 1.4 | 2.100 | 0.01:1 to 100:1 | 0.05:1 to 20:1 | 0.1:1 to 20:1 |
| 479 | 1.4 | 2.101 | 0.01:1 to 100:1 | 0.05:1 to 20:1 | 0.1:1 to 20:1 |
| 480 | 1.4 | 2.102 | 0.01:1 to 100:1 | 0.05:1 to 20:1 | 0.1:1 to 20:1 |
| 481 | 1.4 | 2.103 | 0.01:1 to 100:1 | 0.05:1 to 20:1 | 0.1:1 to 20:1 |
| 482 | 1.4 | 2.104 | 0.01:1 to 100:1 | 0.05:1 to 20:1 | 0.1:1 to 20:1 |
| 483 | 1.4 | 2.105 | 0.01:1 to 100:1 | 0.05:1 to 20:1 | 0.1:1 to 20:1 |
| 484 | 1.4 | 2.106 | 0.01:1 to 100:1 | 0.05:1 to 20:1 | 0.1:1 to 20:1 |
| 485 | 1.4 | 2.107 | 0.01:1 to 100:1 | 0.05:1 to 20:1 | 0.1:1 to 20:1 |
| 486 | 1.4 | 2.108 | 0.01:1 to 100:1 | 0.05:1 to 20:1 | 0.1:1 to 20:1 |
| 487 | 1.4 | 2.109 | 0.01:1 to 100:1 | 0.05:1 to 20:1 | 0.1:1 to 20:1 |
| 488 | 1.4 | 2.110 | 0.01:1 to 100:1 | 0.05:1 to 20:1 | 0.1:1 to 20:1 |
| 489 | 1.4 | 2.111 | 0.01:1 to 100:1 | 0.05:1 to 20:1 | 0.1:1 to 20:1 |
| 490 | 1.4 | 2.112 | 0.01:1 to 100:1 | 0.05:1 to 20:1 | 0.1:1 to 20:1 |
| 491 | 1.4 | 2.113 | 0.01:1 to 100:1 | 0.05:1 to 20:1 | 0.1:1 to 20:1 |
| 492 | 1.4 | 2.114 | 0.01:1 to 100:1 | 0.05:1 to 20:1 | 0.1:1 to 20:1 |
| 493 | 1.4 | 2.115 | 0.01:1 to 100:1 | 0.05:1 to 20:1 | 0.1:1 to 20:1 |
| 494 | 1.4 | 2.116 | 0.01:1 to 100:1 | 0.05:1 to 20:1 | 0.1:1 to 20:1 |
| 495 | 1.4 | 2.117 | 0.01:1 to 100:1 | 0.05:1 to 20:1 | 0.1:1 to 20:1 |
| 496 | 1.4 | 2.118 | 0.01:1 to 100:1 | 0.05:1 to 20:1 | 0.1:1 to 20:1 |
| 497 | 1.4 | 2.119 | 0.01:1 to 100:1 | 0.05:1 to 20:1 | 0.1:1 to 20:1 |
| 498 | 1.4 | 2.120 | 0.01:1 to 100:1 | 0.05:1 to 20:1 | 0.1:1 to 20:1 |
| 499 | 1.4 | 2.121 | 0.01:1 to 100:1 | 0.05:1 to 20:1 | 0.1:1 to 20:1 |
| 500 | 1.4 | 2.122 | 0.01:1 to 100:1 | 0.05:1 to 20:1 | 0.1:1 to 20:1 |
| 501 | 1.4 | 2.123 | 0.01:1 to 100:1 | 0.05:1 to 20:1 | 0.1:1 to 20:1 |
| 502 | 1.4 | 2.124 | 0.01:1 to 100:1 | 0.05:1 to 20:1 | 0.1:1 to 20:1 |
| 503 | 1.4 | 2.125 | 0.01:1 to 100:1 | 0.05:1 to 20:1 | 0.1:1 to 20:1 |
| 504 | 1.4 | 2.126 | 0.01:1 to 100:1 | 0.05:1 to 20:1 | 0.1:1 to 20:1 |
| 505 | 1.5 | 2.1 | 0.01:1 to 100:1 | 0.05:1 to 20:1 | 0.1:1 to 20:1 |
| 506 | 1.5 | 2.2 | 0.01:1 to 100:1 | 0.05:1 to 20:1 | 0.1:1 to 20:1 |
| 507 | 1.5 | 2.3 | 0.01:1 to 100:1 | 0.05:1 to 20:1 | 0.1:1 to 20:1 |
| 508 | 1.5 | 2.4 | 0.01:1 to 100:1 | 0.05:1 to 20:1 | 0.1:1 to 20:1 |
| 509 | 1.5 | 2.5 | 0.01:1 to 100:1 | 0.05:1 to 20:1 | 0.1:1 to 20:1 |
| 510 | 1.5 | 2.6 | 0.01:1 to 100:1 | 0.05:1 to 20:1 | 0.1:1 to 20:1 |
| 511 | 1.5 | 2.7 | 0.01:1 to 100:1 | 0.05:1 to 20:1 | 0.1:1 to 20:1 |
| 512 | 1.5 | 2.8 | 0.01:1 to 100:1 | 0.05:1 to 20:1 | 0.1:1 to 20:1 |
| 513 | 1.5 | 2.9 | 0.01:1 to 100:1 | 0.05:1 to 20:1 | 0.1:1 to 20:1 |
| 514 | 1.5 | 2.10 | 0.01:1 to 100:1 | 0.05:1 to 20:1 | 0.1:1 to 20:1 |
| 515 | 1.5 | 2.11 | 0.01:1 to 100:1 | 0.05:1 to 20:1 | 0.1:1 to 20:1 |
| 516 | 1.5 | 2.12 | 0.01:1 to 100:1 | 0.05:1 to 20:1 | 0.1:1 to 20:1 |
| 517 | 1.5 | 2.13 | 0.01:1 to 100:1 | 0.05:1 to 20:1 | 0.1:1 to 20:1 |
| 518 | 1.5 | 2.14 | 0.01:1 to 100:1 | 0.05:1 to 20:1 | 0.1:1 to 20:1 |
| 519 | 1.5 | 2.15 | 0.01:1 to 100:1 | 0.05:1 to 20:1 | 0.1:1 to 20:1 |
| 520 | 1.5 | 2.16 | 0.01:1 to 100:1 | 0.05:1 to 20:1 | 0.1:1 to 20:1 |
| 521 | 1.5 | 2.17 | 0.01:1 to 100:1 | 0.05:1 to 20:1 | 0.1:1 to 20:1 |
| 522 | 1.5 | 2.18 | 0.01:1 to 100:1 | 0.05:1 to 20:1 | 0.1:1 to 20:1 |
| 523 | 1.5 | 2.19 | 0.01:1 to 100:1 | 0.05:1 to 20:1 | 0.1:1 to 20:1 |
| 524 | 1.5 | 2.20 | 0.01:1 to 100:1 | 0.05:1 to 20:1 | 0.1:1 to 20:1 |
| 525 | 1.5 | 2.21 | 0.01:1 to 100:1 | 0.05:1 to 20:1 | 0.1:1 to 20:1 |
| 526 | 1.5 | 2.22 | 0.01:1 to 100:1 | 0.05:1 to 20:1 | 0.1:1 to 20:1 |
| 527 | 1.5 | 2.23 | 0.01:1 to 100:1 | 0.05:1 to 20:1 | 0.1:1 to 20:1 |
| 528 | 1.5 | 2.24 | 0.01:1 to 100:1 | 0.05:1 to 20:1 | 0.1:1 to 20:1 |
| 529 | 1.5 | 2.25 | 0.01:1 to 100:1 | 0.05:1 to 20:1 | 0.1:1 to 20:1 |
| 530 | 1.5 | 2.26 | 0.01:1 to 100:1 | 0.05:1 to 20:1 | 0.1:1 to 20:1 |
| 531 | 1.5 | 2.27 | 0.01:1 to 100:1 | 0.05:1 to 20:1 | 0.1:1 to 20:1 |
| 532 | 1.5 | 2.28 | 0.01:1 to 100:1 | 0.05:1 to 20:1 | 0.1:1 to 20:1 |
| 533 | 1.5 | 2.29 | 0.01:1 to 100:1 | 0.05:1 to 20:1 | 0.1:1 to 20:1 |
| 534 | 1.5 | 2.30 | 0.01:1 to 100:1 | 0.05:1 to 20:1 | 0.1:1 to 20:1 |
| 535 | 1.5 | 2.31 | 0.01:1 to 100:1 | 0.05:1 to 20:1 | 0.1:1 to 20:1 |

TABLE 2-continued

Compositions of the Invention

| Composition Number | A Cmpd of formula (I) | B Cmpd of formula (II) | Typical Weight Ratio | Preferred Weight Ratio | More Preferred Weight Ratio |
|---|---|---|---|---|---|
| 536 | 1.5 | 2.32 | 0.01:1 to 100:1 | 0.05:1 to 20:1 | 0.1:1 to 20:1 |
| 537 | 1.5 | 2.33 | 0.01:1 to 100:1 | 0.05:1 to 20:1 | 0.1:1 to 20:1 |
| 538 | 1.5 | 2.34 | 0.01:1 to 100:1 | 0.05:1 to 20:1 | 0.1:1 to 20:1 |
| 539 | 1.5 | 2.35 | 0.01:1 to 100:1 | 0.05:1 to 20:1 | 0.1:1 to 20:1 |
| 540 | 1.5 | 2.36 | 0.01:1 to 100:1 | 0.05:1 to 20:1 | 0.1:1 to 20:1 |
| 541 | 1.5 | 2.37 | 0.01:1 to 100:1 | 0.05:1 to 20:1 | 0.1:1 to 20:1 |
| 542 | 1.5 | 2.38 | 0.01:1 to 100:1 | 0.05:1 to 20:1 | 0.1:1 to 20:1 |
| 543 | 1.5 | 2.39 | 0.01:1 to 100:1 | 0.05:1 to 20:1 | 0.1:1 to 20:1 |
| 544 | 1.5 | 2.40 | 0.01:1 to 100:1 | 0.05:1 to 20:1 | 0.1:1 to 20:1 |
| 545 | 1.5 | 2.41 | 0.01:1 to 100:1 | 0.05:1 to 20:1 | 0.1:1 to 20:1 |
| 546 | 1.5 | 2.42 | 0.01:1 to 100:1 | 0.05:1 to 20:1 | 0.1:1 to 20:1 |
| 547 | 1.5 | 2.43 | 0.01:1 to 100:1 | 0.05:1 to 20:1 | 0.1:1 to 20:1 |
| 548 | 1.5 | 2.44 | 0.01:1 to 100:1 | 0.05:1 to 20:1 | 0.1:1 to 20:1 |
| 549 | 1.5 | 2.45 | 0.01:1 to 100:1 | 0.05:1 to 20:1 | 0.1:1 to 20:1 |
| 550 | 1.5 | 2.46 | 0.01:1 to 100:1 | 0.05:1 to 20:1 | 0.1:1 to 20:1 |
| 551 | 1.5 | 2.47 | 0.01:1 to 100:1 | 0.05:1 to 20:1 | 0.1:1 to 20:1 |
| 552 | 1.5 | 2.48 | 0.01:1 to 100:1 | 0.05:1 to 20:1 | 0.1:1 to 20:1 |
| 553 | 1.5 | 2.49 | 0.01:1 to 100:1 | 0.05:1 to 20:1 | 0.1:1 to 20:1 |
| 554 | 1.5 | 2.50 | 0.01:1 to 100:1 | 0.05:1 to 20:1 | 0.1:1 to 20:1 |
| 555 | 1.5 | 2.51 | 0.01:1 to 100:1 | 0.05:1 to 20:1 | 0.1:1 to 20:1 |
| 556 | 1.5 | 2.52 | 0.01:1 to 100:1 | 0.05:1 to 20:1 | 0.1:1 to 20:1 |
| 557 | 1.5 | 2.53 | 0.01:1 to 100:1 | 0.05:1 to 20:1 | 0.1:1 to 20:1 |
| 558 | 1.5 | 2.54 | 0.01:1 to 100:1 | 0.05:1 to 20:1 | 0.1:1 to 20:1 |
| 559 | 1.5 | 2.55 | 0.01:1 to 100:1 | 0.05:1 to 20:1 | 0.1:1 to 20:1 |
| 560 | 1.5 | 2.56 | 0.01:1 to 100:1 | 0.05:1 to 20:1 | 0.1:1 to 20:1 |
| 561 | 1.5 | 2.57 | 0.01:1 to 100:1 | 0.05:1 to 20:1 | 0.1:1 to 20:1 |
| 562 | 1.5 | 2.58 | 0.01:1 to 100:1 | 0.05:1 to 20:1 | 0.1:1 to 20:1 |
| 563 | 1.5 | 2.59 | 0.01:1 to 100:1 | 0.05:1 to 20:1 | 0.1:1 to 20:1 |
| 564 | 1.5 | 2.60 | 0.01:1 to 100:1 | 0.05:1 to 20:1 | 0.1:1 to 20:1 |
| 565 | 1.5 | 2.61 | 0.01:1 to 100:1 | 0.05:1 to 20:1 | 0.1:1 to 20:1 |
| 566 | 1.5 | 2.62 | 0.01:1 to 100:1 | 0.05:1 to 20:1 | 0.1:1 to 20:1 |
| 567 | 1.5 | 2.63 | 0.01:1 to 100:1 | 0.05:1 to 20:1 | 0.1:1 to 20:1 |
| 568 | 1.5 | 2.64 | 0.01:1 to 100:1 | 0.05:1 to 20:1 | 0.1:1 to 20:1 |
| 569 | 1.5 | 2.65 | 0.01:1 to 100:1 | 0.05:1 to 20:1 | 0.1:1 to 20:1 |
| 570 | 1.5 | 2.66 | 0.01:1 to 100:1 | 0.05:1 to 20:1 | 0.1:1 to 20:1 |
| 571 | 1.5 | 2.67 | 0.01:1 to 100:1 | 0.05:1 to 20:1 | 0.1:1 to 20:1 |
| 572 | 1.5 | 2.68 | 0.01:1 to 100:1 | 0.05:1 to 20:1 | 0.1:1 to 20:1 |
| 573 | 1.5 | 2.69 | 0.01:1 to 100:1 | 0.05:1 to 20:1 | 0.1:1 to 20:1 |
| 574 | 1.5 | 2.70 | 0.01:1 to 100:1 | 0.05:1 to 20:1 | 0.1:1 to 20:1 |
| 575 | 1.5 | 2.71 | 0.01:1 to 100:1 | 0.05:1 to 20:1 | 0.1:1 to 20:1 |
| 576 | 1.5 | 2.72 | 0.01:1 to 100:1 | 0.05:1 to 20:1 | 0.1:1 to 20:1 |
| 577 | 1.5 | 2.73 | 0.01:1 to 100:1 | 0.05:1 to 20:1 | 0.1:1 to 20:1 |
| 578 | 1.5 | 2.74 | 0.01:1 to 100:1 | 0.05:1 to 20:1 | 0.1:1 to 20:1 |
| 579 | 1.5 | 2.75 | 0.01:1 to 100:1 | 0.05:1 to 20:1 | 0.1:1 to 20:1 |
| 580 | 1.5 | 2.76 | 0.01:1 to 100:1 | 0.05:1 to 20:1 | 0.1:1 to 20:1 |
| 581 | 1.5 | 2.77 | 0.01:1 to 100:1 | 0.05:1 to 20:1 | 0.1:1 to 20:1 |
| 582 | 1.5 | 2.78 | 0.01:1 to 100:1 | 0.05:1 to 20:1 | 0.1:1 to 20:1 |
| 583 | 1.5 | 2.79 | 0.01:1 to 100:1 | 0.05:1 to 20:1 | 0.1:1 to 20:1 |
| 584 | 1.5 | 2.80 | 0.01:1 to 100:1 | 0.05:1 to 20:1 | 0.1:1 to 20:1 |
| 585 | 1.5 | 2.81 | 0.01:1 to 100:1 | 0.05:1 to 20:1 | 0.1:1 to 20:1 |
| 586 | 1.5 | 2.82 | 0.01:1 to 100:1 | 0.05:1 to 20:1 | 0.1:1 to 20:1 |
| 587 | 1.5 | 2.83 | 0.01:1 to 100:1 | 0.05:1 to 20:1 | 0.1:1 to 20:1 |
| 588 | 1.5 | 2.84 | 0.01:1 to 100:1 | 0.05:1 to 20:1 | 0.1:1 to 20:1 |
| 589 | 1.5 | 2.85 | 0.01:1 to 100:1 | 0.05:1 to 20:1 | 0.1:1 to 20:1 |
| 590 | 1.5 | 2.86 | 0.01:1 to 100:1 | 0.05:1 to 20:1 | 0.1:1 to 20:1 |
| 591 | 1.5 | 2.87 | 0.01:1 to 100:1 | 0.05:1 to 20:1 | 0.1:1 to 20:1 |
| 592 | 1.5 | 2.88 | 0.01:1 to 100:1 | 0.05:1 to 20:1 | 0.1:1 to 20:1 |
| 593 | 1.5 | 2.89 | 0.01:1 to 100:1 | 0.05:1 to 20:1 | 0.1:1 to 20:1 |
| 594 | 1.5 | 2.90 | 0.01:1 to 100:1 | 0.05:1 to 20:1 | 0.1:1 to 20:1 |
| 595 | 1.5 | 2.91 | 0.01:1 to 100:1 | 0.05:1 to 20:1 | 0.1:1 to 20:1 |
| 596 | 1.5 | 2.92 | 0.01:1 to 100:1 | 0.05:1 to 20:1 | 0.1:1 to 20:1 |
| 597 | 1.5 | 2.93 | 0.01:1 to 100:1 | 0.05:1 to 20:1 | 0.1:1 to 20:1 |
| 598 | 1.5 | 2.94 | 0.01:1 to 100:1 | 0.05:1 to 20:1 | 0.1:1 to 20:1 |
| 599 | 1.5 | 2.95 | 0.01:1 to 100:1 | 0.05:1 to 20:1 | 0.1:1 to 20:1 |
| 600 | 1.5 | 2.96 | 0.01:1 to 100:1 | 0.05:1 to 20:1 | 0.1:1 to 20:1 |
| 601 | 1.5 | 2.97 | 0.01:1 to 100:1 | 0.05:1 to 20:1 | 0.1:1 to 20:1 |
| 602 | 1.5 | 2.98 | 0.01:1 to 100:1 | 0.05:1 to 20:1 | 0.1:1 to 20:1 |
| 603 | 1.5 | 2.99 | 0.01:1 to 100:1 | 0.05:1 to 20:1 | 0.1:1 to 20:1 |
| 604 | 1.5 | 2.100 | 0.01:1 to 100:1 | 0.05:1 to 20:1 | 0.1:1 to 20:1 |
| 605 | 1.5 | 2.101 | 0.01:1 to 100:1 | 0.05:1 to 20:1 | 0.1:1 to 20:1 |
| 606 | 1.5 | 2.102 | 0.01:1 to 100:1 | 0.05:1 to 20:1 | 0.1:1 to 20:1 |
| 607 | 1.5 | 2.103 | 0.01:1 to 100:1 | 0.05:1 to 20:1 | 0.1:1 to 20:1 |
| 608 | 1.5 | 2.104 | 0.01:1 to 100:1 | 0.05:1 to 20:1 | 0.1:1 to 20:1 |
| 609 | 1.5 | 2.105 | 0.01:1 to 100:1 | 0.05:1 to 20:1 | 0.1:1 to 20:1 |
| 610 | 1.5 | 2.106 | 0.01:1 to 100:1 | 0.05:1 to 20:1 | 0.1:1 to 20:1 |
| 611 | 1.5 | 2.107 | 0.01:1 to 100:1 | 0.05:1 to 20:1 | 0.1:1 to 20:1 |
| 612 | 1.5 | 2.108 | 0.01:1 to 100:1 | 0.05:1 to 20:1 | 0.1:1 to 20:1 |
| 613 | 1.5 | 2.109 | 0.01:1 to 100:1 | 0.05:1 to 20:1 | 0.1:1 to 20:1 |
| 614 | 1.5 | 2.110 | 0.01:1 to 100:1 | 0.05:1 to 20:1 | 0.1:1 to 20:1 |
| 615 | 1.5 | 2.111 | 0.01:1 to 100:1 | 0.05:1 to 20:1 | 0.1:1 to 20:1 |
| 616 | 1.5 | 2.112 | 0.01:1 to 100:1 | 0.05:1 to 20:1 | 0.1:1 to 20:1 |
| 617 | 1.5 | 2.113 | 0.01:1 to 100:1 | 0.05:1 to 20:1 | 0.1:1 to 20:1 |
| 618 | 1.5 | 2.114 | 0.01:1 to 100:1 | 0.05:1 to 20:1 | 0.1:1 to 20:1 |
| 619 | 1.5 | 2.115 | 0.01:1 to 100:1 | 0.05:1 to 20:1 | 0.1:1 to 20:1 |
| 620 | 1.5 | 2.116 | 0.01:1 to 100:1 | 0.05:1 to 20:1 | 0.1:1 to 20:1 |
| 621 | 1.5 | 2.117 | 0.01:1 to 100:1 | 0.05:1 to 20:1 | 0.1:1 to 20:1 |
| 622 | 1.5 | 2.118 | 0.01:1 to 100:1 | 0.05:1 to 20:1 | 0.1:1 to 20:1 |
| 623 | 1.5 | 2.119 | 0.01:1 to 100:1 | 0.05:1 to 20:1 | 0.1:1 to 20:1 |
| 624 | 1.5 | 2.120 | 0.01:1 to 100:1 | 0.05:1 to 20:1 | 0.1:1 to 20:1 |
| 625 | 1.5 | 2.121 | 0.01:1 to 100:1 | 0.05:1 to 20:1 | 0.1:1 to 20:1 |
| 626 | 1.5 | 2.122 | 0.01:1 to 100:1 | 0.05:1 to 20:1 | 0.1:1 to 20:1 |
| 627 | 1.5 | 2.123 | 0.01:1 to 100:1 | 0.05:1 to 20:1 | 0.1:1 to 20:1 |
| 628 | 1.5 | 2.124 | 0.01:1 to 100:1 | 0.05:1 to 20:1 | 0.1:1 to 20:1 |
| 629 | 1.5 | 2.125 | 0.01:1 to 100:1 | 0.05:1 to 20:1 | 0.1:1 to 20:1 |
| 630 | 1.5 | 2.126 | 0.01:1 to 100:1 | 0.05:1 to 20:1 | 0.1:1 to 20:1 |
| 631 | 1.6 | 2.1 | 0.01:1 to 100:1 | 0.05:1 to 20:1 | 0.1:1 to 20:1 |
| 632 | 1.6 | 2.2 | 0.01:1 to 100:1 | 0.05:1 to 20:1 | 0.1:1 to 20:1 |
| 633 | 1.6 | 2.3 | 0.01:1 to 100:1 | 0.05:1 to 20:1 | 0.1:1 to 20:1 |
| 634 | 1.6 | 2.4 | 0.01:1 to 100:1 | 0.05:1 to 20:1 | 0.1:1 to 20:1 |
| 635 | 1.6 | 2.5 | 0.01:1 to 100:1 | 0.05:1 to 20:1 | 0.1:1 to 20:1 |
| 636 | 1.6 | 2.6 | 0.01:1 to 100:1 | 0.05:1 to 20:1 | 0.1:1 to 20:1 |
| 637 | 1.6 | 2.7 | 0.01:1 to 100:1 | 0.05:1 to 20:1 | 0.1:1 to 20:1 |
| 638 | 1.6 | 2.8 | 0.01:1 to 100:1 | 0.05:1 to 20:1 | 0.1:1 to 20:1 |
| 639 | 1.6 | 2.9 | 0.01:1 to 100:1 | 0.05:1 to 20:1 | 0.1:1 to 20:1 |
| 640 | 1.6 | 2.10 | 0.01:1 to 100:1 | 0.05:1 to 20:1 | 0.1:1 to 20:1 |
| 641 | 1.6 | 2.11 | 0.01:1 to 100:1 | 0.05:1 to 20:1 | 0.1:1 to 20:1 |
| 642 | 1.6 | 2.12 | 0.01:1 to 100:1 | 0.05:1 to 20:1 | 0.1:1 to 20:1 |
| 643 | 1.6 | 2.13 | 0.01:1 to 100:1 | 0.05:1 to 20:1 | 0.1:1 to 20:1 |
| 644 | 1.6 | 2.14 | 0.01:1 to 100:1 | 0.05:1 to 20:1 | 0.1:1 to 20:1 |
| 645 | 1.6 | 2.15 | 0.01:1 to 100:1 | 0.05:1 to 20:1 | 0.1:1 to 20:1 |
| 646 | 1.6 | 2.16 | 0.01:1 to 100:1 | 0.05:1 to 20:1 | 0.1:1 to 20:1 |
| 647 | 1.6 | 2.17 | 0.01:1 to 100:1 | 0.05:1 to 20:1 | 0.1:1 to 20:1 |
| 648 | 1.6 | 2.18 | 0.01:1 to 100:1 | 0.05:1 to 20:1 | 0.1:1 to 20:1 |
| 649 | 1.6 | 2.19 | 0.01:1 to 100:1 | 0.05:1 to 20:1 | 0.1:1 to 20:1 |
| 650 | 1.6 | 2.20 | 0.01:1 to 100:1 | 0.05:1 to 20:1 | 0.1:1 to 20:1 |
| 651 | 1.6 | 2.21 | 0.01:1 to 100:1 | 0.05:1 to 20:1 | 0.1:1 to 20:1 |
| 652 | 1.6 | 2.22 | 0.01:1 to 100:1 | 0.05:1 to 20:1 | 0.1:1 to 20:1 |
| 653 | 1.6 | 2.23 | 0.01:1 to 100:1 | 0.05:1 to 20:1 | 0.1:1 to 20:1 |
| 654 | 1.6 | 2.24 | 0.01:1 to 100:1 | 0.05:1 to 20:1 | 0.1:1 to 20:1 |
| 655 | 1.6 | 2.25 | 0.01:1 to 100:1 | 0.05:1 to 20:1 | 0.1:1 to 20:1 |
| 656 | 1.6 | 2.26 | 0.01:1 to 100:1 | 0.05:1 to 20:1 | 0.1:1 to 20:1 |
| 657 | 1.6 | 2.27 | 0.01:1 to 100:1 | 0.05:1 to 20:1 | 0.1:1 to 20:1 |
| 658 | 1.6 | 2.28 | 0.01:1 to 100:1 | 0.05:1 to 20:1 | 0.1:1 to 20:1 |
| 659 | 1.6 | 2.29 | 0.01:1 to 100:1 | 0.05:1 to 20:1 | 0.1:1 to 20:1 |
| 660 | 1.6 | 2.30 | 0.01:1 to 100:1 | 0.05:1 to 20:1 | 0.1:1 to 20:1 |
| 661 | 1.6 | 2.31 | 0.01:1 to 100:1 | 0.05:1 to 20:1 | 0.1:1 to 20:1 |
| 662 | 1.6 | 2.32 | 0.01:1 to 100:1 | 0.05:1 to 20:1 | 0.1:1 to 20:1 |
| 663 | 1.6 | 2.33 | 0.01:1 to 100:1 | 0.05:1 to 20:1 | 0.1:1 to 20:1 |
| 664 | 1.6 | 2.34 | 0.01:1 to 100:1 | 0.05:1 to 20:1 | 0.1:1 to 20:1 |
| 665 | 1.6 | 2.35 | 0.01:1 to 100:1 | 0.05:1 to 20:1 | 0.1:1 to 20:1 |
| 666 | 1.6 | 2.36 | 0.01:1 to 100:1 | 0.05:1 to 20:1 | 0.1:1 to 20:1 |
| 667 | 1.6 | 2.37 | 0.01:1 to 100:1 | 0.05:1 to 20:1 | 0.1:1 to 20:1 |
| 668 | 1.6 | 2.38 | 0.01:1 to 100:1 | 0.05:1 to 20:1 | 0.1:1 to 20:1 |
| 669 | 1.6 | 2.39 | 0.01:1 to 100:1 | 0.05:1 to 20:1 | 0.1:1 to 20:1 |
| 670 | 1.6 | 2.40 | 0.01:1 to 100:1 | 0.05:1 to 20:1 | 0.1:1 to 20:1 |
| 671 | 1.6 | 2.41 | 0.01:1 to 100:1 | 0.05:1 to 20:1 | 0.1:1 to 20:1 |
| 672 | 1.6 | 2.42 | 0.01:1 to 100:1 | 0.05:1 to 20:1 | 0.1:1 to 20:1 |
| 673 | 1.6 | 2.43 | 0.01:1 to 100:1 | 0.05:1 to 20:1 | 0.1:1 to 20:1 |
| 674 | 1.6 | 2.44 | 0.01:1 to 100:1 | 0.05:1 to 20:1 | 0.1:1 to 20:1 |
| 675 | 1.6 | 2.45 | 0.01:1 to 100:1 | 0.05:1 to 20:1 | 0.1:1 to 20:1 |
| 676 | 1.6 | 2.46 | 0.01:1 to 100:1 | 0.05:1 to 20:1 | 0.1:1 to 20:1 |
| 677 | 1.6 | 2.47 | 0.01:1 to 100:1 | 0.05:1 to 20:1 | 0.1:1 to 20:1 |

TABLE 2-continued

Compositions of the Invention

| Composition Number | A Cmpd of formula (I) | B Cmpd of formula (II) | Typical Weight Ratio | Preferred Weight Ratio | More Preferred Weight Ratio |
|---|---|---|---|---|---|
| 678 | 1.6 | 2.48 | 0.01:1 to 100:1 | 0.05:1 to 20:1 | 0.1:1 to 20:1 |
| 679 | 1.6 | 2.49 | 0.01:1 to 100:1 | 0.05:1 to 20:1 | 0.1:1 to 20:1 |
| 680 | 1.6 | 2.50 | 0.01:1 to 100:1 | 0.05:1 to 20:1 | 0.1:1 to 20:1 |
| 681 | 1.6 | 2.51 | 0.01:1 to 100:1 | 0.05:1 to 20:1 | 0.1:1 to 20:1 |
| 682 | 1.6 | 2.52 | 0.01:1 to 100:1 | 0.05:1 to 20:1 | 0.1:1 to 20:1 |
| 683 | 1.6 | 2.53 | 0.01:1 to 100:1 | 0.05:1 to 20:1 | 0.1:1 to 20:1 |
| 684 | 1.6 | 2.54 | 0.01:1 to 100:1 | 0.05:1 to 20:1 | 0.1:1 to 20:1 |
| 685 | 1.6 | 2.55 | 0.01:1 to 100:1 | 0.05:1 to 20:1 | 0.1:1 to 20:1 |
| 686 | 1.6 | 2.56 | 0.01:1 to 100:1 | 0.05:1 to 20:1 | 0.1:1 to 20:1 |
| 687 | 1.6 | 2.57 | 0.01:1 to 100:1 | 0.05:1 to 20:1 | 0.1:1 to 20:1 |
| 688 | 1.6 | 2.58 | 0.01:1 to 100:1 | 0.05:1 to 20:1 | 0.1:1 to 20:1 |
| 689 | 1.6 | 2.59 | 0.01:1 to 100:1 | 0.05:1 to 20:1 | 0.1:1 to 20:1 |
| 690 | 1.6 | 2.60 | 0.01:1 to 100:1 | 0.05:1 to 20:1 | 0.1:1 to 20:1 |
| 691 | 1.6 | 2.61 | 0.01:1 to 100:1 | 0.05:1 to 20:1 | 0.1:1 to 20:1 |
| 692 | 1.6 | 2.62 | 0.01:1 to 100:1 | 0.05:1 to 20:1 | 0.1:1 to 20:1 |
| 693 | 1.6 | 2.63 | 0.01:1 to 100:1 | 0.05:1 to 20:1 | 0.1:1 to 20:1 |
| 694 | 1.6 | 2.64 | 0.01:1 to 100:1 | 0.05:1 to 20:1 | 0.1:1 to 20:1 |
| 695 | 1.6 | 2.65 | 0.01:1 to 100:1 | 0.05:1 to 20:1 | 0.1:1 to 20:1 |
| 696 | 1.6 | 2.66 | 0.01:1 to 100:1 | 0.05:1 to 20:1 | 0.1:1 to 20:1 |
| 697 | 1.6 | 2.67 | 0.01:1 to 100:1 | 0.05:1 to 20:1 | 0.1:1 to 20:1 |
| 698 | 1.6 | 2.68 | 0.01:1 to 100:1 | 0.05:1 to 20:1 | 0.1:1 to 20:1 |
| 699 | 1.6 | 2.69 | 0.01:1 to 100:1 | 0.05:1 to 20:1 | 0.1:1 to 20:1 |
| 700 | 1.6 | 2.70 | 0.01:1 to 100:1 | 0.05:1 to 20:1 | 0.1:1 to 20:1 |
| 701 | 1.6 | 2.71 | 0.01:1 to 100:1 | 0.05:1 to 20:1 | 0.1:1 to 20:1 |
| 702 | 1.6 | 2.72 | 0.01:1 to 100:1 | 0.05:1 to 20:1 | 0.1:1 to 20:1 |
| 703 | 1.6 | 2.73 | 0.01:1 to 100:1 | 0.05:1 to 20:1 | 0.1:1 to 20:1 |
| 704 | 1.6 | 2.74 | 0.01:1 to 100:1 | 0.05:1 to 20:1 | 0.1:1 to 20:1 |
| 705 | 1.6 | 2.75 | 0.01:1 to 100:1 | 0.05:1 to 20:1 | 0.1:1 to 20:1 |
| 706 | 1.6 | 2.76 | 0.01:1 to 100:1 | 0.05:1 to 20:1 | 0.1:1 to 20:1 |
| 707 | 1.6 | 2.77 | 0.01:1 to 100:1 | 0.05:1 to 20:1 | 0.1:1 to 20:1 |
| 708 | 1.6 | 2.78 | 0.01:1 to 100:1 | 0.05:1 to 20:1 | 0.1:1 to 20:1 |
| 709 | 1.6 | 2.79 | 0.01:1 to 100:1 | 0.05:1 to 20:1 | 0.1:1 to 20:1 |
| 710 | 1.6 | 2.80 | 0.01:1 to 100:1 | 0.05:1 to 20:1 | 0.1:1 to 20:1 |
| 711 | 1.6 | 2.81 | 0.01:1 to 100:1 | 0.05:1 to 20:1 | 0.1:1 to 20:1 |
| 712 | 1.6 | 2.82 | 0.01:1 to 100:1 | 0.05:1 to 20:1 | 0.1:1 to 20:1 |
| 713 | 1.6 | 2.83 | 0.01:1 to 100:1 | 0.05:1 to 20:1 | 0.1:1 to 20:1 |
| 714 | 1.6 | 2.84 | 0.01:1 to 100:1 | 0.05:1 to 20:1 | 0.1:1 to 20:1 |
| 715 | 1.6 | 2.85 | 0.01:1 to 100:1 | 0.05:1 to 20:1 | 0.1:1 to 20:1 |
| 716 | 1.6 | 2.86 | 0.01:1 to 100:1 | 0.05:1 to 20:1 | 0.1:1 to 20:1 |
| 717 | 1.6 | 2.87 | 0.01:1 to 100:1 | 0.05:1 to 20:1 | 0.1:1 to 20:1 |
| 718 | 1.6 | 2.88 | 0.01:1 to 100:1 | 0.05:1 to 20:1 | 0.1:1 to 20:1 |
| 719 | 1.6 | 2.89 | 0.01:1 to 100:1 | 0.05:1 to 20:1 | 0.1:1 to 20:1 |
| 720 | 1.6 | 2.90 | 0.01:1 to 100:1 | 0.05:1 to 20:1 | 0.1:1 to 20:1 |
| 721 | 1.6 | 2.91 | 0.01:1 to 100:1 | 0.05:1 to 20:1 | 0.1:1 to 20:1 |
| 722 | 1.6 | 2.92 | 0.01:1 to 100:1 | 0.05:1 to 20:1 | 0.1:1 to 20:1 |
| 723 | 1.6 | 2.93 | 0.01:1 to 100:1 | 0.05:1 to 20:1 | 0.1:1 to 20:1 |
| 724 | 1.6 | 2.94 | 0.01:1 to 100:1 | 0.05:1 to 20:1 | 0.1:1 to 20:1 |
| 725 | 1.6 | 2.95 | 0.01:1 to 100:1 | 0.05:1 to 20:1 | 0.1:1 to 20:1 |
| 726 | 1.6 | 2.96 | 0.01:1 to 100:1 | 0.05:1 to 20:1 | 0.1:1 to 20:1 |
| 727 | 1.6 | 2.97 | 0.01:1 to 100:1 | 0.05:1 to 20:1 | 0.1:1 to 20:1 |
| 728 | 1.6 | 2.98 | 0.01:1 to 100:1 | 0.05:1 to 20:1 | 0.1:1 to 20:1 |
| 729 | 1.6 | 2.99 | 0.01:1 to 100:1 | 0.05:1 to 20:1 | 0.1:1 to 20:1 |
| 730 | 1.6 | 2.100 | 0.01:1 to 100:1 | 0.05:1 to 20:1 | 0.1:1 to 20:1 |
| 731 | 1.6 | 2.101 | 0.01:1 to 100:1 | 0.05:1 to 20:1 | 0.1:1 to 20:1 |
| 732 | 1.6 | 2.102 | 0.01:1 to 100:1 | 0.05:1 to 20:1 | 0.1:1 to 20:1 |
| 733 | 1.6 | 2.103 | 0.01:1 to 100:1 | 0.05:1 to 20:1 | 0.1:1 to 20:1 |
| 734 | 1.6 | 2.104 | 0.01:1 to 100:1 | 0.05:1 to 20:1 | 0.1:1 to 20:1 |
| 735 | 1.6 | 2.105 | 0.01:1 to 100:1 | 0.05:1 to 20:1 | 0.1:1 to 20:1 |
| 736 | 1.6 | 2.106 | 0.01:1 to 100:1 | 0.05:1 to 20:1 | 0.1:1 to 20:1 |
| 737 | 1.6 | 2.107 | 0.01:1 to 100:1 | 0.05:1 to 20:1 | 0.1:1 to 20:1 |
| 738 | 1.6 | 2.108 | 0.01:1 to 100:1 | 0.05:1 to 20:1 | 0.1:1 to 20:1 |
| 739 | 1.6 | 2.109 | 0.01:1 to 100:1 | 0.05:1 to 20:1 | 0.1:1 to 20:1 |
| 740 | 1.6 | 2.110 | 0.01:1 to 100:1 | 0.05:1 to 20:1 | 0.1:1 to 20:1 |
| 741 | 1.6 | 2.111 | 0.01:1 to 100:1 | 0.05:1 to 20:1 | 0.1:1 to 20:1 |
| 742 | 1.6 | 2.112 | 0.01:1 to 100:1 | 0.05:1 to 20:1 | 0.1:1 to 20:1 |
| 743 | 1.6 | 2.113 | 0.01:1 to 100:1 | 0.05:1 to 20:1 | 0.1:1 to 20:1 |
| 744 | 1.6 | 2.114 | 0.01:1 to 100:1 | 0.05:1 to 20:1 | 0.1:1 to 20:1 |
| 745 | 1.6 | 2.115 | 0.01:1 to 100:1 | 0.05:1 to 20:1 | 0.1:1 to 20:1 |
| 746 | 1.6 | 2.116 | 0.01:1 to 100:1 | 0.05:1 to 20:1 | 0.1:1 to 20:1 |
| 747 | 1.6 | 2.117 | 0.01:1 to 100:1 | 0.05:1 to 20:1 | 0.1:1 to 20:1 |
| 748 | 1.6 | 2.118 | 0.01:1 to 100:1 | 0.05:1 to 20:1 | 0.1:1 to 20:1 |
| 749 | 1.6 | 2.119 | 0.01:1 to 100:1 | 0.05:1 to 20:1 | 0.1:1 to 20:1 |
| 750 | 1.6 | 2.120 | 0.01:1 to 100:1 | 0.05:1 to 20:1 | 0.1:1 to 20:1 |
| 751 | 1.6 | 2.121 | 0.01:1 to 100:1 | 0.05:1 to 20:1 | 0.1:1 to 20:1 |
| 752 | 1.6 | 2.122 | 0.01:1 to 100:1 | 0.05:1 to 20:1 | 0.1:1 to 20:1 |
| 753 | 1.6 | 2.123 | 0.01:1 to 100:1 | 0.05:1 to 20:1 | 0.1:1 to 20:1 |
| 754 | 1.6 | 2.124 | 0.01:1 to 100:1 | 0.05:1 to 20:1 | 0.1:1 to 20:1 |
| 755 | 1.6 | 2.125 | 0.01:1 to 100:1 | 0.05:1 to 20:1 | 0.1:1 to 20:1 |
| 756 | 1.6 | 2.126 | 0.01:1 to 100:1 | 0.05:1 to 20:1 | 0.1:1 to 20:1 |

The skilled man will appreciate that the most preferred ratio range of A:B for any one of composition numbers 1 to 756 described in Table 2 above is from 0.2:1 to 20:1, and that each one of composition numbers 1 to 756 described in Table 2 may used at the ratio of A:B of 0.3125:1, or at the ratio of A:B of 0.625:1, or at the ratio of A:B of 1.25:1, or at the ratio of A:B of 2.5:1, or at the ratio of A:B of 5:1, or at the ratio of A:B of 10:1, or at the ratio of A:B of 20:1.

Whilst 756 two-way mixtures of a compound of formula (I) and another herbicide are explicitly disclosed above, the skilled man will appreciate that the invention extends to three-way and further multiple combinations comprising the above two-way mixtures. In particular, the present invention provides compositions comprising the three-way mixtures, wherein each of the 2-way mixtures described in Table 2 above, is combined with (a) mesotrione (mixtures 3a1 to 3a756, respectively); (b) bicyclopyrone (mixtures 3b1 to 3b756, respectively); (c) atrazine (mixtures 3d1 to 3c756, respectively); (d) S-metholachlor (mixtures 3d1 to 3d756, respectively); (e) terbuthylazine (mixtures 3e1 to 3e756, respectively); (f) dimethaclor (mixtures 3f1 to 3f756, respectively); (g) flufenacet (mixtures 3g1 to 3g756, respectively); (h) glyphosate (mixtures 3h1 to 3h756, respectively); (i) isoxaflutole (mixtures 3i1 to 3i756, respectively); (j) nicosulfuron (mixtures 3j1 to 3j756, respectively); (k) ametryn (mixtures 3k1 to 3k756, respectively); (l) hexazinone (mixtures 3l1 to 3l756, respectively); (m) paraquat (mixtures 3m1 to 3m756, respectively); (n) diquat (mixtures 3n1 to 3n756, respectively); (o) pyridate (mixtures 3o1 to 3o756, respectively); (p) acetochlor (mixtures 3p1 to 3p756, respectively); (q) dimethenamid-P (mixtures 3q1 to 3q756, respectively); (r) alachlor (mixtures 3r1 to 3r756, respectively); (s) pethoxamid (mixtures 3s1 to 3s756, respectively); (t) pyroxosulfone (mixtures 3t1 to 3t756, respectively); (u) trifloxysulfuron sodium (mixtures 3u1 to 3u756, respectively); (v) flazasulfuron (mixtures 3v1 to 3v756, respectively); (w) prosulfocarb (mixtures 3w1 to 3w756, respectively); (x) metolachlor (mixtures 3×1 to 3×756, respectively); or (y) pretilachlor (mixtures 3y1 to 3y756, respectively).

Various aspects and embodiments of the present invention will now be illustrated in more detail by way of example. It will be appreciated that modification of detail may be made without departing from the scope of the invention.

For the avoidance of doubt, where a literary reference, patent application, or patent, is cited within the text of this application, the entire text of said citation is herein incorporated by reference.

PREPARATION EXAMPLES FOR COMPOUNDS OF FORMULA (11)

General Experimental

Chiral HPLC was recorded on the columns below with the solvents and gradients stated.

Column:

Regis Whelk O1 (s,s) 4.6×100 mm, 3.5 μm

Chiralpak IC 4.6×100 mm, 3.0 μm

Solvents:

A: iso-Hexane+0.1% glacial Acetic Acid (v/v)

B: Ethanol+0.1% glacial Acetic Acid (v/v)

Gradient:

| Time (mins): | Flow (mL/min): | % A: | % B: |
|---|---|---|---|
| 0.0 | 1.0 | 85 | 15 |
| 1.0 | 1.0 | 85 | 15 |
| 7.0 | 1.0 | 50 | 50 |
| 15.0 | 1.0 | 40 | 60 |

Synthesis Method (I): Racemic Synthesis Route

Exemplar compound: N-(2,3-difluorophenyl)-1-methyl-4-[1-methyl-5-(trifluoromethyl)pyrazol-3-yl]-2-oxo-pyrrolidine-3-carboxamide Synthesis scheme (I)

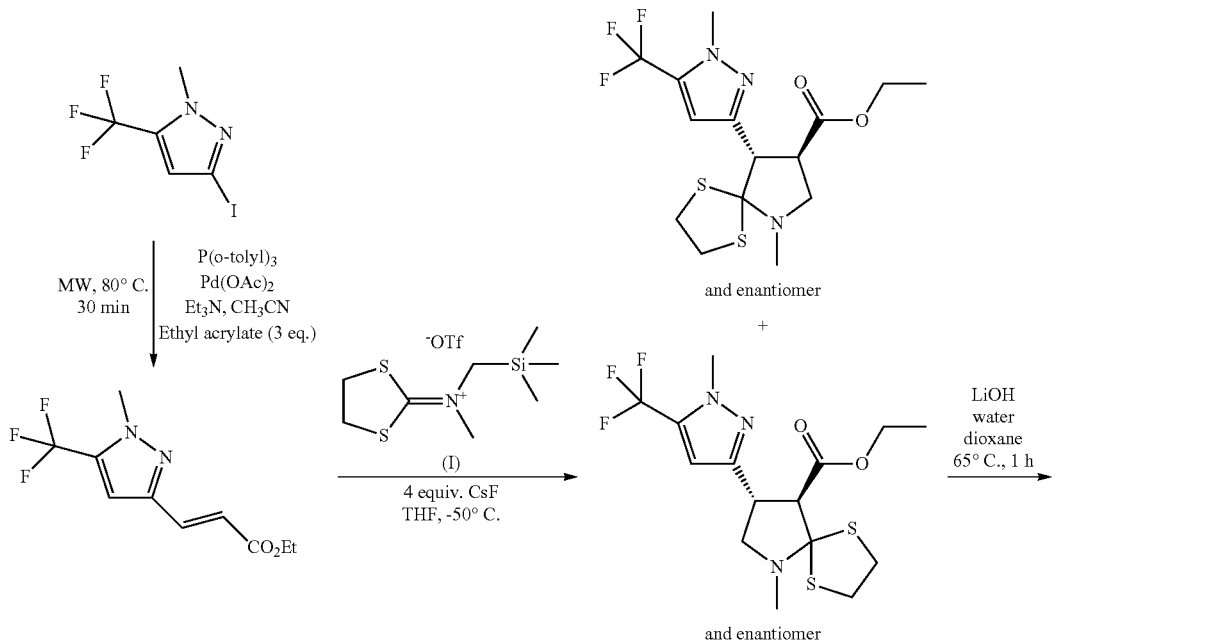

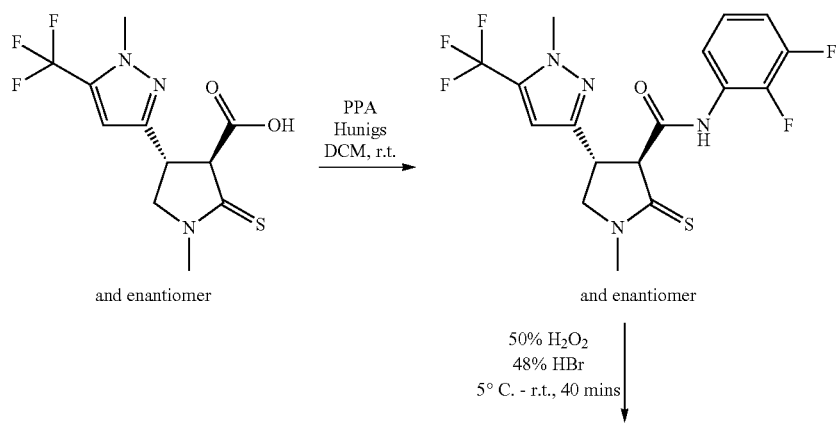

-continued

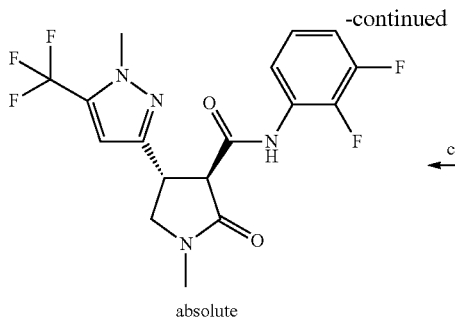

absolute

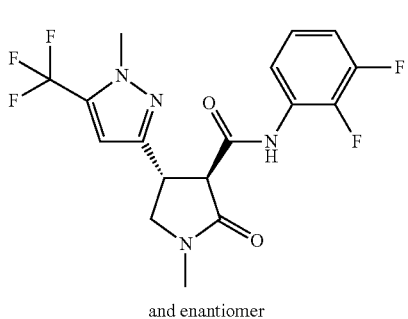

and enantiomer

Salt (1) can be prepared as described in *Tetrahedron Lett.* 1995, 36, 9409.

Step 1 Ethyl (E)-3-[1-methyl-5-(trifluoromethyl)pyrazol-3-yl]prop-2-enoate

In a large microwave vial 3-iodo-1-methyl-5-(trifluoromethyl)pyrazole (3.62 mmol, 1.00 g) was dissolved in acetonitrile (15.2 mL), and ethyl acrylate (1.19 mL, 10.9 mmol), triethylamine (0.507 mL, 3.64 mmol), tri-ortho-tolylphosphine (0.362 mmol, 0.110 g) and palladium(II) acetate (0.362 mmol, 0.0813 g) were added, the air space above the stirred orange solution was swept with nitrogen, and the vial sealed and heated at 110° C. under microwave irradiation for 60 minutes. The reaction mixture was filtered (rinsing through with small portions of EtOAc), and the combined filtrate and washings were concentrated to remove the bulk of solvent. The residual orange-brown liquid was diluted with water (12 mL) and extracted with EtOAc (3×15 mL). The organic extracts were combined, washed with water (10 mL), passed through a phase seperation cartridge then concentrated. Column chromatography (EtOAc/iso-hexane gradient elution) gave ethyl (E)-3-[1-methyl-5-(trifluoromethyl)pyrazol-3-yl]prop-2-enoate as a yellow oil, 0.51 g (57%).

$^1$H NMR: (400 MHz, CDCl$_3$): δ=7.58 (d, J=16.1 Hz, 1H), 6.81 (s, 1H), 6.43 (d, J=16.1 Hz, 1H), 4.26 (q, J=7.1 Hz, 2H), 4.01 (d, J=0.6 Hz, 3H), 1.33 (t, J=7.1 Hz, 3H).

Step 2 Ethyl-6-methyl-8-[1-methyl-5-(trifluoromethyl)pyrazol-3-yl]-1,4-dithia-6-azaspiro[4.4]nonane-9-carboxylate To a suspension of finely divided cesium fluoride (12.7 mmol, 1.93 g) in tetrahydrofuran (9.51 mL) stirred at −50° C., under a nitrogen atmosphere, was added a solution of ethyl (E)-3-[1-methyl-5-(trifluoromethyl)pyrazol-3-yl]prop-2-enoate (3.17 mmol, 0.787 g) and 1,3-dithiolan-2-ylidenemethyl-(trimethylsilylmethyl)ammonium; trifluoromethanesulfonic acid (5.55 mmol, 2.06 g) in tetrahydrofuran (39.51 mL) drop-wise over approx. 15 minutes, keeping the reaction temperature below −45° C. The resulting very pale yellow cloudy suspension was allowed to warm slowly to room temperature and stirring was continued overnight. The reaction mixture was then diluted with DCM and filtered, washing through with further portions of DCM. The combined filtrate and washings were concentrated, and the crude material purified by column chromatography (EtOAc/cyclohexane gradient elution) giving ethyl-6-methyl-8-[1-methyl-5-(trifluoromethyl)pyrazol-3-yl]-1,4-dithia-6-azaspiro[4.4]nonane-9-carboxylate as a pale yellow oil, 566 mg (45%).

$^1$H NMR: (400 MHz, CDCl$_3$): δ=6.45 (s, 1H), 4.31-4.17 (m, 2H), 3.90 (d, J=0.6 Hz, 3H), 3.89-3.79 (m, 2H), 3.35-3.06 (m, 5H), 2.97-2.91 (m, 1H), 2.47 (s, 3H), 1.31 (t, J=7.2 Hz, 3H).

Step 3 1-Methyl-4-[1-methyl-5-(trifluoromethyl)pyrazol-3-yl]-2-thioxo-pyrrolidine-3-carboxylic acid To a solution of ethyl 6-methyl-8-[1-methyl-5-(trifluoromethyl)pyrazol-3-yl]-1,4-dithia-6-azaspiro[4.4]nonane-9-carboxylate (1.43 mmol, 0.566 g) in dioxane (34.3 mL) and water (11.4 mL) was added LiOH (14.3 mmol, 0.343 g), and the stirred mixture heated to 60° C. under a nitrogen atmosphere for 1 hour. The reaction mixture was then allowed to cool to around 35° C. then concentrated to remove the bulk of dioxane. The residual mixture was diluted with water (10 mL), and partitioned between dilute HCl (5 mL, to pH3) and DCM (20 mL). The two-phase mixture was filtered to remove fine solids then the organic phase was separated. The aqueous was further extracted with DCM (2×15 mL), and all organic extracts combined, dried over MgSO$_4$, filtered and the filtrate concentrated giving 1-methyl-4-[1-methyl-5-(trifluoromethyl)pyrazol-3-yl]-2-thioxo-pyrrolidine-3-carboxylic acid as a light yellow solid, 399 mg (90%).

$^1$H NMR: (400 MHz, CDCl$_3$): δ=6.66 (s, 1H), 4.19-4.03 (m, 4H), 3.93 (d, J=0.5 Hz, 3H), 3.34 (s, 3H).

Step 4 N-(2,3-difluorophenyl)-1-methyl-4-[1-methyl-5-(trifluoromethyl)pyrazol-3-yl]-2-thioxo-pyrrolidine-3-carboxamide To a solution of 1-methyl-4-[1-methyl-5-(trifluoromethyl)pyrazol-3-yl]-2-thioxo-pyrrolidine-3-carboxylic acid (0.340 g, 1.11 mmol) in DCM (8.0 mL) was added 2,3-difluoroaniline (0.112 mL, 1.11 mmol) giving a pale yellow solution. Propylphosphonic anhydride (50 mass %) in ethyl acetate (1.88 mmol, 1.12 mL) was added, followed by the N,N-diisopropylamine (3.32 mmol, 0.578 mL) and the reaction mixture was stirred at room temperature for 1 hour. The reaction mixture was then quenched by the addition of water (2 mL) with stirring, transferred to a phase separation cartridge and the organics collected and concentrated. Column chromatography (EtOAc/iso-hexane gradient elution) gave N-(2,3-difluorophenyl)-1-methyl-4-[1-methyl-5-(trifluoromethyl)pyrazol-3-yl]-2-thioxo-pyrrolidine-3-carboxamide as a colourless crystalline solid, 264 mg (57%).

$^1$H NMR: (400 MHz, CDCl$_3$): δ=10.25 (br s, 1H), 8.01 (tdd, J=1.6, 6.6, 8.3 Hz, 1H), 7.04 (ddt, J=2.1, 5.9, 8.3 Hz, 1H), 6.94-6.86 (m, 1H), 6.58 (s, 1H), 4.40 (td, J=6.3, 8.6 Hz, 1H), 4.20 (d, J=6.4 Hz, 1H), 4.13 (dd, 1H), 4.00 (dd, 1H), 3.93 (d, 3H), 3.33 (s, 3H).

Step 5 N-(2,3-difluorophenyl)-1-methyl-4-[1-methyl-5-(trifluoromethyl)pyrazol-3-yl]-2-oxo-pyrrolidine-3-carboxamide To a solution of N-(2,3-difluorophenyl)-1-methyl-4-[1-methyl-5-(trifluoromethyl)pyrazol-3-yl]-2-thioxo-pyrrolidine-3-carboxamide (0.621 mmol, 0.260 g) in acetonitrile (6.21 mL) stirred and cooled to around 0 to −5° C., in an ice-salt bath, was added 50% hydrogen peroxide (0.746 mL) drop-wise and a white suspension resulted. After 5 minutes 45% aq. hydrobromic acid (0.0750 mL, 0.621 mmol) was added drop-wise and after stirring for 10 minutes the mixture was allowed to warm to room temperature. After 3 hours the reaction mixture was re-cooled to 5° C., and quenched with sodium thiosulfate solution (~10 mL). The mixture was diluted with EtOAc (15 mL) and water (10 mL), and the organic phase separated. The aqueous was further extracted with EtOAc (2×10 mL), then the organic extracts were combined, run through a phase separation cartridge then concentrated giving a colourless gum. Column chromatography (EtOAc/iso-hexane gradient elution) gave N-(2,3-difluorophenyl)-1-methyl-4-[1-methyl-5-(trifluoromethyl)pyrazol-3-yl]-2-oxo-pyrrolidine-3-carboxamide as a white crystalline solid, 210 mg (84%).

$^1$H NMR: (400 MHz, CDCl$_3$): δ=10.15 (br s, 1H), 8.04 (dd, J=6.6, 8.3 Hz, 1H), 7.06-6.99 (m, 1H), 6.89 (br dd, J=1.1, 8.6 Hz, 1H), 6.69 (s, 1H), 4.09 (q, 1H), 3.94 (s, 3H), 3.78 (d, J=9.5 Hz, 1H), 3.76-3.65 (m, 2H), 2.98 (d, 3H).

The racemic N-(2,3-difluorophenyl)-1-methyl-4-[1-methyl-5-(trifluoromethyl)pyrazol-3-yl]-2-oxo-pyrrolidine-3-carboxamide could be separated to afford the enantiomers (3S,4R)—N-(2,3-difluorophenyl)-1-methyl-4-[1-methyl-5-(trifluoromethyl)pyrazol-3-yl]-2-oxo-pyrrolidine-3 carboxamide and (3R,4S)—N-(2,3-difluorophenyl)-1-methyl-4-[1-methyl-5-(trifluoromethyl)pyrazol-3-yl]-2-oxo-pyrrolidine-3-carboxamide using a Chiralpak IA, 10×250 mm, 5 μm column with sc-CO$_2$ (solvent A) B=Isopropanol (solvent B) as solvents under isocratic conditions: 85% solvent A:15% solvent B at 15 mL/min.

Synthesis Method (II): Asymmetric Synthesis Route

Exemplar Compound: (3S,4R)—N-(2,3-difluorophenyl)-1-methyl-4-[1-methyl-5-(trifluoromethyl)pyrazol-3-yl]-2-oxo-pyrrolidine-3-carboxamide

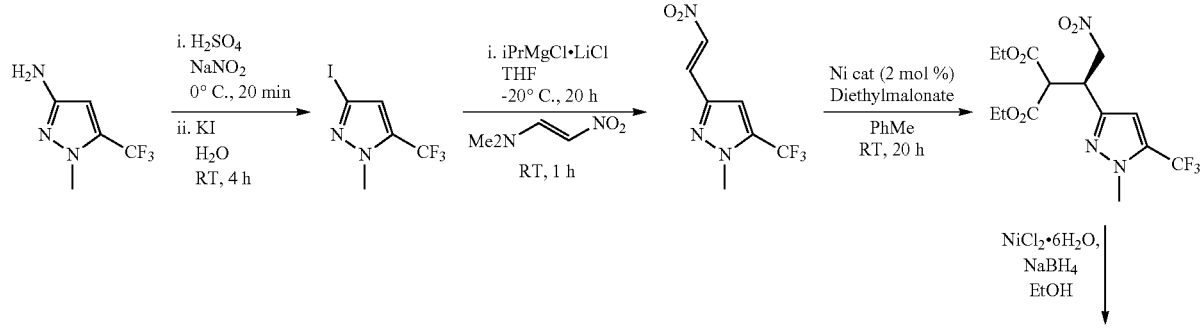

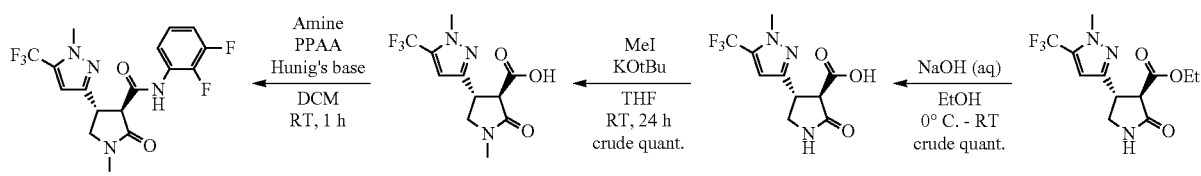

The Nickel catalyst used in step 3, which catalyses the asymmetric malonate addition to the nitro olefin, can be prepared as in J. Am. Chem. Soc. 2005, 127, 9958-9959.

Step 1 3-iodo-1-methyl-5-(trifluoromethyl)pyrazole

The compound 1-methyl-5-(trifluoromethyl)pyrazol-3-amine (5.00 g, 30.3 mmol) was stirred in 9M sulfuric acid (818 mmol, 91 mL) in a 500 mL beaker, using an overhead stirrer at 0° C. (ice bath) until a homogenous mixture resulted. Sodium nitrite (60.6 mmol, 4.18 g), in 10 mL of water, was then added dropwise over 5 minutes, resulting in a colourless solution and the reaction was stirred at 0° C. for a further 20 minutes. Potassium iodide (75.7 mmol, 12.6 g), in 20 mL of water, was added dropwise to the reaction and the mixture was then stirred for a further 4 hours. The reaction was quenched with saturated sodium thiosulfate until the mixture became clear. The mixture was then diluted with dichloromethane and the phases were separated. The aqueous was further extracted with dichloromethane and the combined organic extracts were washed with water, dried (MgSO4), filtered and concentrated under vacuum to afford a pale yellow oil. The crude product was purified by column chromatography (EtOAc/hexanes gradient elution) to afford 3-iodo-1-methyl-5-(trifluoromethyl)pyrazole as a colourless oil, 3.9 g, (47%).
$^1$H NMR (400 MHz, CDCl$_3$) δ=6.76 (s, 1H) 4.01 (d, J=0.61 Hz, 3H).

Step 2 1-Methyl-3-[(E)-2-nitrovinyl]-5-(trifluoromethyl)pyrazole

Isopropylmagnesium chloride-Lithium chloride in THE (23.55 mmol, 1.3 mol/L) was added dropwise to 3-iodo-1-methyl-5-(trifluoromethyl)pyrazole (5.0 g, 18.12 mmol) in THE (90 mL) at −20° C. and the mixture was stirred for 2 hours. 1-Dimethylamino-2-nitroethylene (27.17 mmol, 3.321 g) was added and the reaction was slowly warmed to RT over 1 hour. The reaction mixture was then carefully quenched with 2 M HCl, and extracted with ethyl acetate. The organic extracts were washed with brine, dried (MgSO4), filtered, concentrated and purified by chromatography (EtOAc/cyclohexane gradient elution) to afford 1-methyl-3-[(E)-2-nitrovinyl]-5-(trifluoromethyl)pyrazole (74.6%) as a yellow oil, 2.99 g (74.6%).
$^1$H NMR (400 MHz, CDCl$_3$) δ=7.89 (d, J=13.7 Hz, 1H), 7.63 (d, J=13.7 Hz, 1H), 6.88 (s, 1H), 4.05 (d, J=0.6 Hz, 3H).

Step 3 Diethyl 2-[(1S)-1-[1-methyl-5-(trifluoromethyl)pyrazol-3-yl]-2-nitro-ethyl]propanedioate To a solution of 1-methyl-3-[(E)-2-nitrovinyl]-5-(trifluoromethyl)pyrazole (0.650 g, 2.94 mmol) in toluene (19.5 mL) was added diethyl malonate (0.676 mL, 4.41 mmol) followed by Nickel(II)Bis[(1R,2R)—N1,N2-bis(phenylmethyl)-1,2-cyclohexanediamine-N1,N2]dibromide (0.0588 mmol, 0.0472 g), and the mixture was stirred at ambient temperature for 20 hours.

The reaction mixture was washed with water (2×10 mL) and the organic phase separated, concentrated and purified by chromatography (EtOAc/cyclohexane gradient elution) to afford diethyl 2-[(1S)-1-[1-methyl-5-(trifluoromethyl)pyrazol-3-yl]-2-nitro-ethyl]propanedioate as pale yellow oil, 1.07 g (95%).
$^1$H NMR (400 MHz, CDCl$_3$) δ=6.53 (s, 1H), 5.01 (dd, 1H), 4.88 (dd, J=4.3, 13.9 Hz, 1H), 4.35 (ddd, J=4.4, 7.7, 9.0 Hz, 1H), 4.22 (q, 2H), 4.16 (q, J=7.1 Hz, 2H), 3.90 (s, 3H), 3.89 (d, 1H), 1.26 (t, 3H), 1.20 (t, J=7.2 Hz, 3H).

Step 4 Ethyl (3R,4R)-4-[1-methyl-5-(trifluoromethyl)pyrazol-3-yl]-2-oxo-pyrrolidine-3-carboxylate To a solution of diethyl 2-[(1R)-1-[1-methyl-5-(trifluoromethyl)pyrazol-3-yl]-2-nitro-ethyl]propanedioate (1.07 g, 2.81 mmol) in ethanol (42.1 mL) cooled to 0-5° C. (ice bath) under nitrogen, was added dichloronickel hexahydrate (2.95 mmol, 0.700 g). Sodium borohydride (8.42 mmol, 0.325 g) was then added portionwise to the pale greenish-blue solution. After 30 minutes the cooling was removed and the reaction mixture allowed to warm to ambient temperature. After stirring for 5 hours, at ambient temperature, the reaction mixture was cooled to 5-10° C., in an ice-water bath, and slowly quenched with ammonium chloride solution, and the mixture stirred for a further 20 minutes. The mixture was then diluted with EtOAc (20 mL), and filtered through a bed of celite, washing through with portions of water and EtOAc. The collected two-phase mixture was concentrated to remove the bulk of solvent and the residue transferred to a separating funnel, diluted with EtOAc (20 mL) and the organic phase separated. The aqueous phase was further extracted with EtOAc (2×25 mL) and all organic extracts combined, passed through a phase separation concentrated and purified by chromatography (EtOAc/hexanes gradient elution) to afford a pale yellow oil, 0.61 g (77%) which crystallised on standing.
$^1$H NMR (400 MHz, CDCl$_3$) δ=6.91 (br s, 1H), 6.47 (s, 1H), 4.28 (q, J=7.2 Hz, 2H), 4.14 (q, 1H), 3.94 (d, 3H), 3.80 (dt, J=1.0, 9.0 Hz, 1H), 3.63 (d, J=9.3 Hz, 1H), 3.52 (dd, J=8.2, 9.5 Hz, 1H), 1.32 (t, J=7.2 Hz, 3H).

Step 5 (3R,4R)-4-[1-methyl-5-(trifluoromethyl)pyrazol-3-yl]-2-oxo-pyrrolidine-3-carboxylic acid To a solution of ethyl (3R,4R)-4-[1-methyl-5-(trifluoromethyl)pyrazol-3-yl]-2-oxo-pyrrolidine-3-carboxylate (0.61 g, 2.0 mmol) in ethanol (6.0 mL) and water (2.0 mL) at 0° C. (ice bath) was added 2M sodium hydroxide (3 mL, 6.0 mmol). The reaction mixture was stirred at 0° C. for 30 minutes and then diluted with water (15 mL) and extracted with EtOAc (25 mL). The organic extracts were washed with water (10 mL), and the aqueous extracts combined and acidified to pH 2 with dilute HCl. The acidified aqueous extracts were then re-extracted with EtOAc (3×20 mL) and these organic extracts were run through a phase separation cartridge and concentrated affording a pale yellow oil, 0.54 g (quantitative) which crystallised on standing.
$^1$H NMR (400 MHz, CDCl3) □=6.59 (s, 1H), 4.09 (q, 1H), 3.94 (s, 3H), 3.85-3.77 (m, 1H), 3.72 (d, J=10.0 Hz, 1H), 3.66-3.58 (m, 1H).

Step 6 (3R,4R)-1-methyl-4-[1-methyl-5-(trifluoromethyl)pyrazol-3-yl]-2-oxo-pyrrolidine-3-carboxylic acid To a stirred solution of (3R,4R)-4-[1-methyl-5-(trifluoromethyl)pyrazol-3-yl]-2-oxo-pyrrolidine-3-carboxylic acid (0.57 g, 2.1 mmol, 0.57 g) in tetrahydrofuran (16 mL), at room temperature, under a nitrogen atmosphere was added potassium tertiary butoxide (1.0 M in THF) (4.5 mL, 4.5 mmol) giving a pale yellow fine suspension. To this suspension was added iodomethane (0.19 mL, 3.1 mmol), and stirring at room temp was continued for 20 h. The stirred reaction mixture was acidified to pH2 with dilute HCl and the mixture was diluted with water (10 mL) and extracted with EtOAc (3×30 mL). The combined organic extracts were washed with brine (15 mL), dried over magnesium sulfate, filtered and the filtrate concentrated giving a transparent amber gum, 0.63 g ((quantitative).

$^1$H NMR: (400 MHz, CDCl3) δ=6.68 (s, 1H), 3.97 (q, 1H), 3.94 (s, 3H), 3.76-3.68 (m, 3H), 2.99 (s, 3H).

Step 7 (3S,4R)—N-(2,3-difluorophenyl)-1-methyl-4-[1-methyl-5-(trifluoromethyl)pyrazol-3-yl]-2-oxo-pyrrolidine-3-carboxamide To a solution of (3R,4R)-1-methyl-4-[1-methyl-5-(trifluoromethyl)pyrazol-3-yl]-2-oxo-pyrrolidine-3-carboxylic acid (0.61 g, 2.1 mmol) in dichloromethane (15 mL) was added 2,3-difluoroaniline (0.21 mL, 2.1 mmol). Propylphosphonic anhydride (50 mass %) in ethyl acetate (2.3 g, 3.6 mmol, 2.1 mL) was then added, and the reaction mixture was then immersed in a room temp water bath. N,N-Diisopropylethylamine (1.1 mL, 6.3 mmol) was added drop-wise, and the reaction was stirred at room temperature for 2.5 hour. The reaction mixture was quenched by the addition of water (15 mL) and transferred to a phase sep cartridge. The aqueous was further extracted with DCM (2×10 mL) and the combined organic extracts were concentrated and purified by chromatography (EtOAc/hexanes gradient elution) to afford a pink oil. Trituration with iso-hexane afforded a pale pink solid 398 mg (47%). 1H NMR: (400 MHz, CDCl$_3$) δ=10.16 (br s, 1H), 8.08-8.01 (m, 1H), 7.02 (ddt, J=2.1, 5.9, 8.3 Hz, 1H), 6.93-6.84 (m, 1H), 6.69 (s, 1H), 4.09 (q, 1H), 3.94 (s, 3H), 3.78 (d, J=9.5 Hz, 1H), 3.76-3.65 (m, 2H), 2.98 (s, 3H).

Chiral HPLC analysis, by the methods stated above, confirmed an enantiomeric ratio of 97:3.

Further compounds of formula (II) were synthesized in an analogous manner using the above described two synthetic routes. These are shown in Tables 3 and 4 below.

TABLE 3

Compounds of formula (II) prepared using synthesis method (I) NMR data corresponds to that for the repective racemates

| Compound No. | Structure | 1HNMR (CDCl$_3$) |
| --- | --- | --- |
| 2.1 | 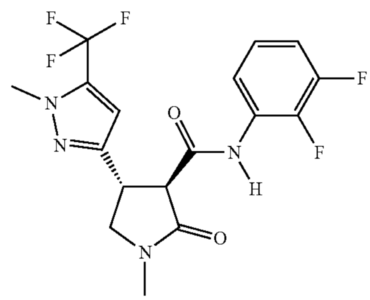 [SMILES: CN1C[C@H](c2cc(C(F)(F)F)n(C)n2)[C@@H](C(=O)Nc2cccc(F)c2F)C1=O] | δ = 10.15 (br s, 1H), 8.04 (tdd, J = 1.6, 6.6, 8.3 Hz, 1H), 7.02 (ddt, J = 2.1, 5.9, 8.3 Hz, 1H), 6.93-6.85 (m, 1H), 6.69 (s, 1H), 4.09 (q, 1H), 3.94 (s, 3H), 3.81-3.65 (m, 3H), 2.98 (d, 3H) |
| 2.2 | 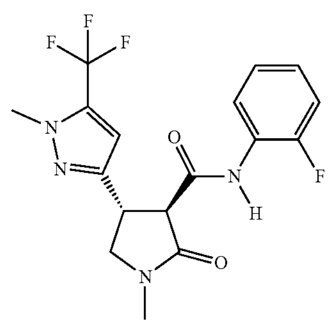 [SMILES: CN1C[C@H](c2cc(C(F)(F)F)n(C)n2)[C@@H](C(=O)Nc2ccccc2F)C1=O] | δ = 10.04 (br s, 1H), 8.31-8.25 (m, 1H), 7.13-7.00 (m, 3H), 6.69 (s, 1H), 4.11 (q, 1H), 3.94 (s, 3H), 3.80-3.65 (m, 3H), 2.98 (d, 3H) |
| 2.3 | 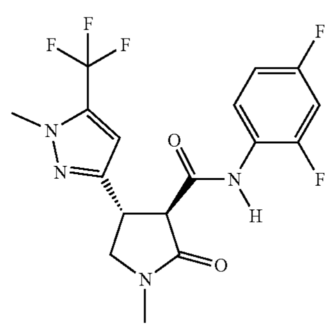 [SMILES: CN1C[C@H](c2cc(C(F)(F)F)n(C)n2)[C@@H](C(=O)Nc2ccc(F)cc2F)C1=O] | δ = 9.98 (br s, 1H), 8.22 (dt, J = 6.0, 8.9 Hz, 1H), 6.90-6.80 (m, 2H), 6.69 (s, 1H), 4.09 (q, 1H), 3.94 (d, 3H), 3.80-3.65 (m, 3H), 2.97 (d, J = 0.7 Hz, 3H) |

TABLE 3-continued

Compounds of formula (II) prepared using synthesis method (I) NMR data corresponds to that for the repective racemates

| Compound No. | Structure | 1HNMR (CDCl₃) |
|---|---|---|
| 2.4 | 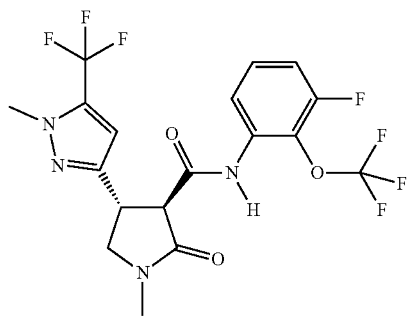 [SMILES: CN1C[C@H](c2cc(C(F)(F)F)n(C)n2)[C@@H](C(=O)Nc2cccc(F)c2OC(F)(F)F)C1=O] | δ = 10.40 (s, 1H), 8.17 (td, J = 1.5, 8.5 Hz, 1H), 7.26-7.19 (m, 1H), 6.92 (ddd, J = 1.4, 8.4, 9.7 Hz, 1H), 6.69 (s, 1H), 4.07 (q, J = 9.0 Hz, 1H), 3.94 (s, 3H), 3.77 (d, 1H), 3.74-3.64 (m, 2H), 2.98 (s, 3H) |
| 2.5 | 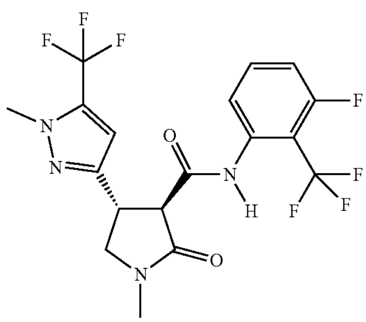 [SMILES: CN1C[C@H](c2cc(C(F)(F)F)n(C)n2)[C@@H](C(=O)Nc2cccc(F)c2C(F)(F)F)C1=O] | δ = 10.16 (br s, 1H), 7.99 (d, J = 8.3 Hz, 1H), 7.46 (dt, J = 6.0, 8.4 Hz, 1H), 7.00-6.92 (m, 1H), 6.68 (s, 1H), 4.09 (q, J = 8.9 Hz, 1H), 3.94 (s, 3H), 3.79-3.66 (m, 3H), 2.98 (d, 3H) |
| 2.6 | 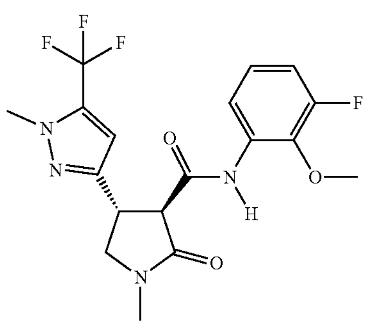 | δ = 10.21 (s, 1H), 8.13 (td, J = 1.3, 8.4 Hz, 1H), 6.96 (dt, J = 5.7, 8.3 Hz, 1H), 6.81 (ddd, J = 1.5, 8.4, 11.1 Hz, 1H), 6.68 (s, 1H), 4.13 (q, J = 9.0 Hz, 1H), 4.03 (d, J = 1.7 Hz, 3H), 3.94 (d, 3H), 3.78-3.63 (m, 3H), 2.97 (d, J = 0.7 Hz, 3H) |
| 2.7 | 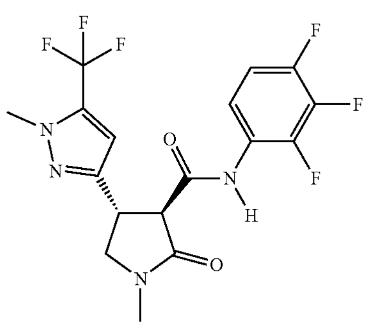 [SMILES: CN1C[C@H](c2cc(C(F)(F)F)n(C)n2)[C@@H](C(=O)Nc2ccc(F)c(F)c2F)C1=O] | δ = 10.08 (br s, 1H), 8.01-7.94 (m, 1H), 6.92 (ddt, J = 2.4, 7.7, 9.7 Hz, 1H), 6.68 (s, 1H), 4.07 (q, 1H), 3.94 (s, 3H), 3.77 (d, 1H), 3.75-3.65 (m, 2H), 2.98 (d, 3H) |

TABLE 3-continued

Compounds of formula (II) prepared using synthesis method (I) NMR data corresponds to that for the repective racemates

| Compound No. | Structure | 1HNMR (CDCl₃) |
|---|---|---|
| 2.8 | 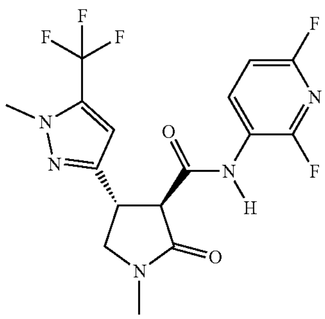 [SMILES: CN1C[C@H](c2cc(C(F)(F)F)n(C)n2)[C@@H](C(=O)Nc2ccc(F)nc2F)C1=O] | δ = 10.17 (br s, 1H), 8.83-8.76 (m, 1H), 6.80 (dd, J = 2.9, 8.6 Hz, 1H), 6.67 (s, 1H), 4.07 (q, J = 8.9 Hz, 1H), 3.95 (d, 3H), 3.83-3.65 (m, 3H), 2.98 (d, 3H) |
| 2.9 | 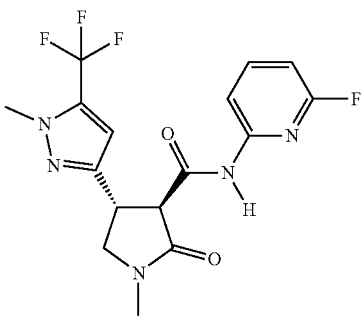 [SMILES: CN1C[C@H](c2cc(C(F)(F)F)n(C)n2)[C@@H](C(=O)Nc2cccc(F)n2)C1=O] | δ = 10.04 (s, 1H), 8.01 (dd, J = 1.8, 7.9 Hz, 1H), 7.75 (q, J = 8.1 Hz, 1H), 6.65 (s, 1H), 6.64 (dd, 1H), 4.12 (q, J = 9.0 Hz, 1H), 3.94 (s, 3H), 3.77-3.61 (m, 3H), 2.96 (s, 3H) |
| 2.10 | 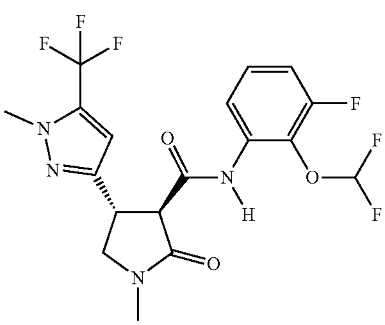 [SMILES: CN1C[C@H](c2cc(C(F)(F)F)n(C)n2)[C@@H](C(=O)Nc2cccc(F)c2OC(F)F)C1=O] | δ = 10.29 (s, 1H), 8.17 (td, J = 1.3, 8.4 Hz, 1H), 7.17 (dt, J = 5.9, 8.5 Hz, 1H), 6.89 (ddd, J = 1.3, 8.5, 10.0 Hz, 1H), 6.68 (s, 1H), 6.67 (t[large F coupling], 1H), 4.09 (q, J = 9.0 Hz, 1H), 3.94 (s, 3H), 3.78 (d, J = 9.5 Hz, 1H), 3.75-3.63 (m, 2H), 2.98 (m, 3H) |
| 2.11 | 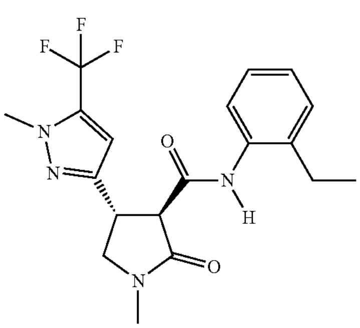 [SMILES: CCc1ccccc1NC(=O)[C@H]1C(=O)N(C)C[C@@H]1c1cc(C(F)(F)F)n(C)n1] | δ = 9.73 (s, 1H), 8.05 (d, 1H), 7.34-7.27 (m, 1H), 7.22-7.16 (m, 1H), 7.10-7.05 (m, 1H), 6.72 (s, 1H), 4.17-4.07 (m, 1H), 3.94 (s, 3H), 3.77-3.66 (m, 3H), 2.97 (d, 3H), 2.77-2.65 (m, 2H), 1.27 (t, 3H) |

TABLE 3-continued
Compounds of formula (II) prepared using synthesis method (I) NMR data corresponds to that for the repective racemates
| Compound No. | Structure | 1HNMR (CDCl$_3$) |
|---|---|---|
| 2.12 | 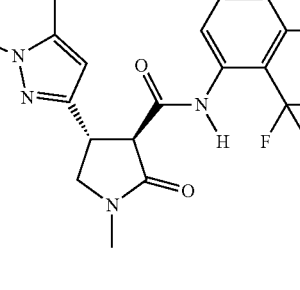 | δ = 9.75 (br s, 1H), 8.11 (dd, J = 5.1, 9.0 Hz, 1H), 7.21 (dd, J = 2.9, 9.2 Hz, 1H), 7.13-7.06 (m, 1H), 6.67 (s, 1H), 4.13 (q, J = 8.9 Hz, 1H), 3.94 (s, 3H), 3.76-3.64 (m, 3H), 2.97 (s, 3H), 1.98 (t, 3H) |
| 2.43 | 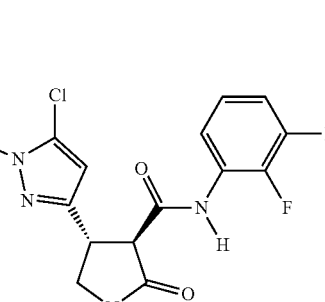 | δ = 10.14 (s, 1H), 8.09-7.97 (m, 1H), 7.08-6.97 (m, 1H), 6.92-6.82 (m, 1H), 6.27 (s, 1H), 4.10-3.97 (m, 1H), 3.88-3.75 (m, 1H), 3.80 (s, 3H), 3.74-3.60 (m, 2H), 2.95 (s, 3H). |
| 2.45 | 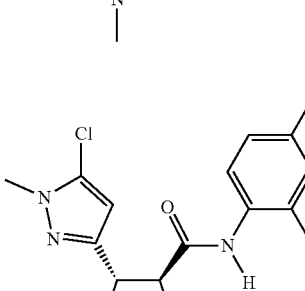 | δ = 9.96 (brs, 1H), 8.28-8.18 (m, 1H), 6.91-6.77 (m, 2H), 6.27 (s, 1H), 4.05 (q, J = 9.0 Hz, 1H), 3.83-3.60 (m, 3H), 3.79 (s, 3H), 2.96 (s, 3H) |
| 2.49 | 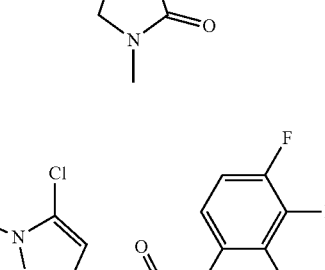 | δ = 10.06 (s, 1H), 8.03-7.93 (m, 1H), 6.98-6.85 (m, 1H), 6.27 (s, 1H), 4.03 (q, 1H), 3.83-3.60 (m, 3H), 3.80 (s, 3H), 2.97 (s, 3H). |

TABLE 4

Compounds of formula (II) prepared using synthesis method (II) NMR data corresponds to that for the single enantiomer as shown

| Compound No. | Structure | 1HNMR (CDCl$_3$) |
|---|---|---|
| 2.1 | (structure) | δ = 10.15 (br s, 1H), 8.04 (dd, J = 6.6, 8.3 Hz, 1H), 7.06-6.99 (m, 1H), 6.89 (br dd, J = 1.1, 8.6 Hz, 1H), 6.69 (s, 1H), 4.09 (q, 1H), 3.94 (s, 3H), 3.78 (d, J = 9.5 Hz, 1H), 3.76-3.65 (m, 2H), 2.98 (d, 3H) |
| 2.15 | (structure) | δ = 10.05 (br s, 1H), 8.04-7.97 (m, 1H), 7.46 (s, 1H), 7.01 (ddt, J = 2.1, 5.9, 8.3 Hz, 1H), 6.93-6.84 (m, 1H), 4.21 (q, J = 8.8 Hz, 1H), 4.00 (s, 3H), 3.75 (t, J = 9.5 Hz, 1H), 3.64 (d, J = 9.4 Hz, 1H), 3.27 (dd, J = 8.1, 9.9 Hz, 1H), 2.97 (s, 3H) |

BIOLOGICAL EXAMPLES

Herbicidal Efficacy of Compounds of Formula (II)

Seeds of a variety of test species [*Ipomoea hederacea* (IPOHE); *Zea mays* (ZEAMX); *Echinochloa crus-galli* (ECHCG); *Setaria faberi* (SETFA); *Abutilon theophrasti* (ABUTH); *Amaranthus retroflexus* (AMARE)] were sown in standard sterilised soil in pots. After cultivation for one day (pre-emergence) or after 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5), subsequently diluted in water, and sprayed to give the stated application rate.

The test plants were then grown under controlled conditions in a glasshouse (at 24/16° C., day/night; 14 hours light; 65% humidity) and watered twice daily.

After 13 days for pre and post-emergence, the test was evaluated visually for percentage phytotoxicity to the plant (where 100=total damage to plant; 0=no damage to plant). Results are shown in Tables B1 and B2.

TABLE B1

Application post-emergence

| Compound Number | Rate (g/ha) | AMARE | ABUTH | SETFA | ECHCG | ZEAMX | IPOHE |
|---|---|---|---|---|---|---|---|
| 2.1 | 250 | 20 | 0 | 90 | 90 | 80 | 0 |
| 2.3 | 250 | 10 | 60 | 70 | 70 | 60 | 10 |
| 2.2 | 250 | 0 | 0 | 90 | 90 | 50 | 0 |
| 2.4 | 250 | 0 | 0 | 70 | 70 | 0 | 0 |
| 2.7 | 250 | 50 | 0 | 80 | 80 | 80 | 0 |
| 2.6 | 250 | 0 | 0 | 70 | 70 | 80 | 50 |
| 2.5 | 250 | 30 | 0 | 80 | 80 | 10 | 0 |
| 2.11 | 250 | 20 | 0 | 80 | 80 | 0 | 0 |
| 2.8 | 250 | 0 | 0 | 80 | 80 | 80 | 30 |
| 2.10 | 250 | 0 | 0 | 80 | 80 | 80 | 30 |
| 2.9 | 250 | 0 | 0 | 80 | 80 | 40 | 50 |
| 2.12 | 250 | 0 | 0 | 90 | 90 | 80 | 50 |
| 2.15 | 250 | 0 | 0 | 80 | 80 | 30 | 40 |

TABLE B2

| | | Application pre-emergence | | | | | |
|---|---|---|---|---|---|---|---|
| Compound Number | Rate (g/ha) | AMARE | ABUTH | SETFA | ECHCG | ZEAMX | IPOHE |
| 2.1  | 250 | 70 | 10 | 90  | 100 | 90 | 30 |
| 2.3  | 250 | 50 | 70 | 90  | 90  | 60 | 10 |
| 2.2  | 250 | 20 | 0  | 90  | 90  | 20 | 0  |
| 2.4  | 250 | 0  | 0  | 90  | 90  | 30 | 50 |
| 2.7  | 250 | 20 | 10 | 90  | 100 | 90 | 20 |
| 2.6  | 250 | 0  | 0  | 90  | 90  | 80 | 20 |
| 2.5  | 250 | 0  | 0  | 90  | 90  | 20 | 10 |
| 2.11 | 250 | 70 | 0  | 90  | 90  | 20 | 0  |
| 2.8  | 250 | 20 | 0  | 90  | 90  | 40 | 0  |
| 2.10 | 250 | 0  | 0  | 90  | 90  | 40 | 20 |
| 2.9  | 250 | 0  | 0  | 90  | 100 | 80 | 40 |
| 2.12 | 250 | 0  | 0  | 90  | 90  | 90 | 70 |
| 2.15 | 250 | 0  | 40 | 100 | 100 | 40 | 20 |

The invention claimed is:
1. A compound of formula (II)

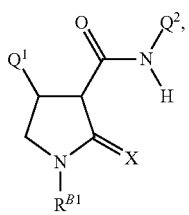

(II)

wherein:
$R^{B1}$ is methyl;
X is O or S;
$Q^1$ is selected from the group consisting of $Q^1$-2a or $Q^1$-2b

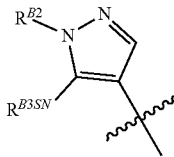

$Q^1$-2a

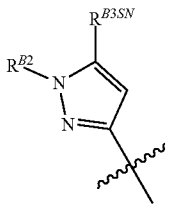

$Q^1$-2b $R^{B2}$ is $C_1$-$C_3$ alkyl and $R^{B3SN}$ is independently selected from halogen, $C_1$-$C_3$fluoroalkyl, $C_1$-$C_3$haloalkoxy, $C_1$-$C_3$alkoxy, and $C_1$-$C_3$alkyl and the jagged line denotes the point of attachment to the rest of the molecule;
$Q^2$ is a phenyl, pyridinyl, or thienyl ring system, optionally substituted by 1, 2, or 3 $R^{B5}$ substituents; and each $R^{B5}$ is independently halogen, $C_1$-$C_6$alkyl, $C_1$-$C_6$haloalkyl, $C_1$-$C_6$alkoxy, $C_1$-$C_6$haloalkoxy, cyano, nitro, $C_1$-$C_6$alkylthio, $C_1$-$C_6$alkylsulphinyl, or $C_1$-$C_6$alkylsulphonyl;

or an N-oxide, or a salt form thereof.

2. The compound of claim 1, wherein X is O.

3. The compound of claim 1, wherein $Q^2$ is selected from the group consisting of $Q^2$-1, $Q^2$-2, $Q^2$-3, $Q^2$-4, $Q^2$-5, and $Q^2$-6,

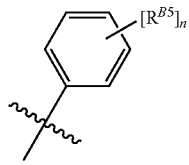

$Q^2$-1

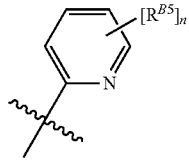

$Q^2$-2

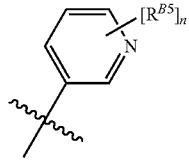

$Q^2$-3

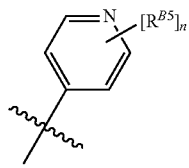

$Q^2$-4

Q²-5

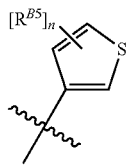

Q²-6

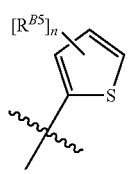

wherein n is an integer of 0, 1, 2, or 3, $R^{B5}$ is as defined in claim 1, and the jagged line represents the point of attachment to the rest of the molecule.

4. The compound of claim 1, wherein each $R^{B5}$ is independently halogen, $C_1$-$C_4$ alkyl, $C_1$-$C_3$ haloalkyl, $C_1$-$C_3$alkoxy, or $C_1$-$C_3$haloalkoxy.

5. The compound of claim 1, wherein $R^{B2}$ is selected from the group consisting of methyl, ethyl, and n-propyl.

6. The compound of claim 1, wherein $R^{B3SN}$ is halogen.

7. The compound of claim 1, wherein $R^{B3SN}$ is $C_1$-$C_3$fluoroalkyl.

8. The compound of claim 7, wherein $R^{B3SN}$ is trifluoromethyl.

9. A compound selected from:

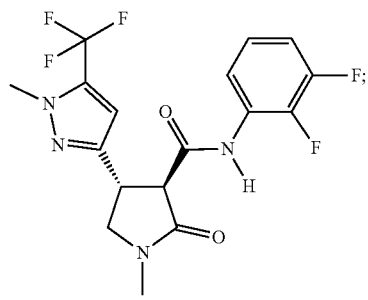

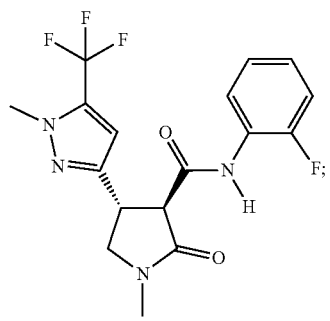

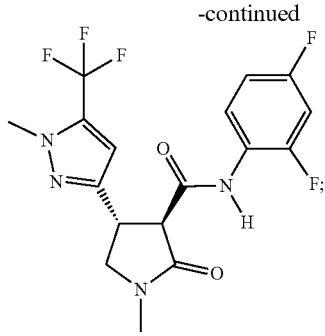

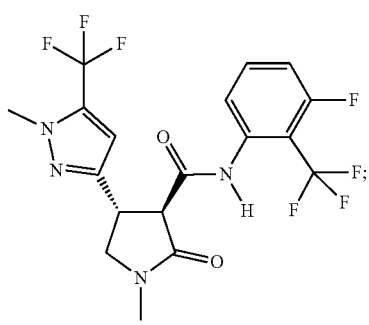

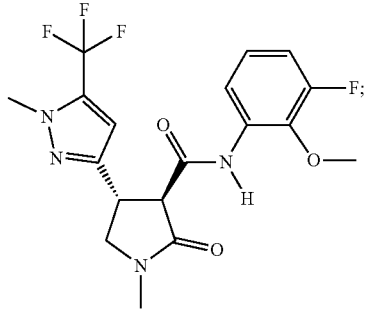

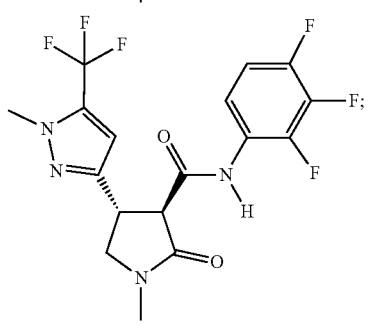

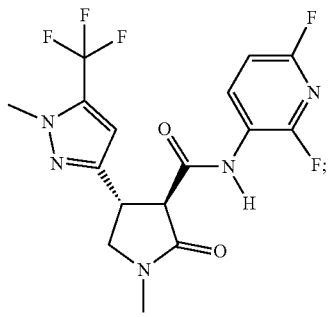

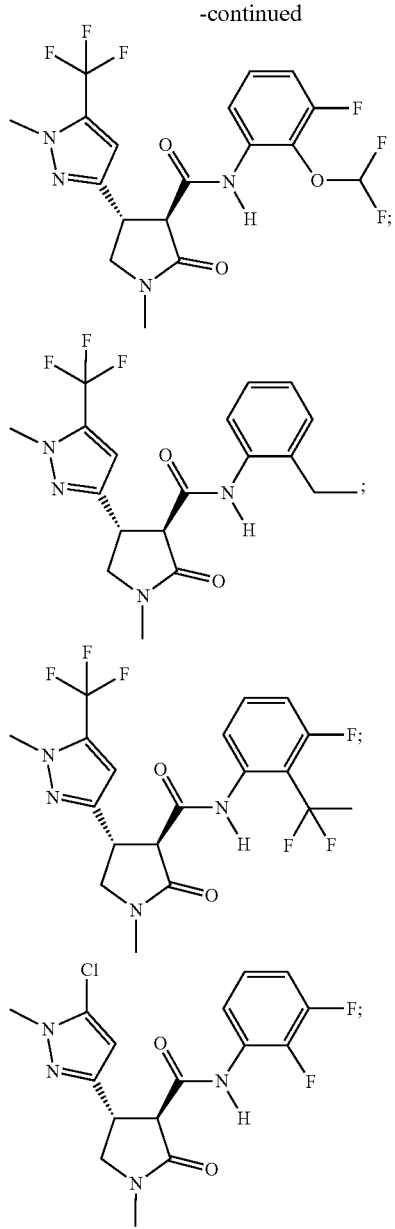
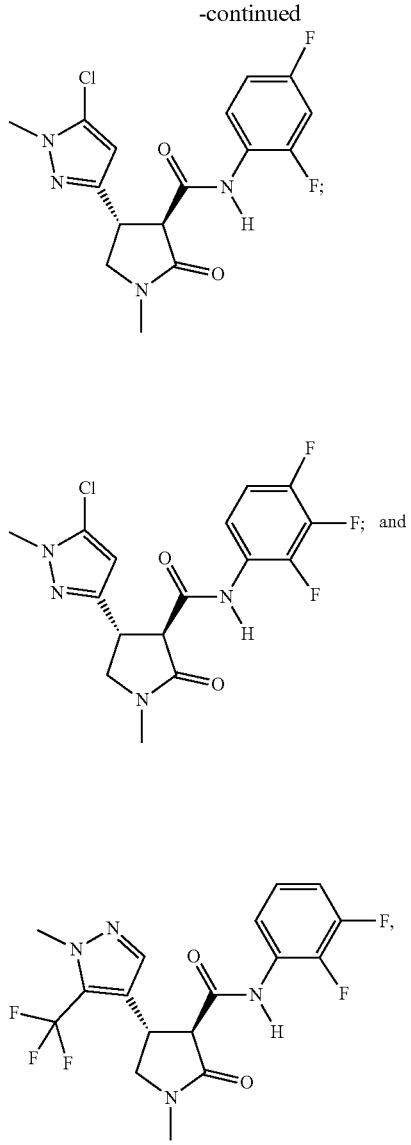
or an N-oxide, or a salt form thereof.
* * * * *